(12) United States Patent
McElroy et al.

(10) Patent No.: US 6,207,879 B1
(45) Date of Patent: *Mar. 27, 2001

(54) MAIZE RS81 PROMOTER AND METHODS FOR USE THEREOF

(75) Inventors: David McElroy, Palo Alto, CA (US); Emil M. Orozco, Jr., West Grove, PA (US); Lucille B. Laccetti, Groton, CT (US)

(73) Assignee: Dekalb Genetics Corporation, Mystic, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/312,266

(22) Filed: May 14, 1999

(51) Int. Cl.⁷ ............... C12N 15/05; C12N 15/29; C12N 15/63; C12N 15/82; A01H 5/00
(52) U.S. Cl. ............... 800/278; 800/279; 800/295; 800/298; 800/312; 800/314; 800/317; 800/320; 800/322; 800/281; 800/300; 800/301; 800/302; 800/303; 800/289; 800/290; 800/293; 800/284; 800/287; 800/294; 800/317.2; 800/317.3; 800/317.4; 800/306; 800/292; 435/69.1; 435/320.1; 435/418; 435/419; 435/468; 435/252.3; 536/23.1; 536/24.1; 536/23.6
(58) Field of Search ........ 800/278, 295, 800/287, 298, 320, 320.1, 320.2, 320.3, 317.2, 317.3, 317.4, 312, 314, 279, 281, 284, 289, 290, 300, 361, 302, 303, 306, 322, 292, 293, 294, 317; 435/69.1, 252.3, 320.1, 419, 468, 418, 413, 412, 414, 415, 416, 417; 536/23.1, 24.1, 23.6

(56) References Cited

U.S. PATENT DOCUMENTS

| | | | |
|---|---|---|---|
| 5,459,252 | 10/1795 | Conkling et al. | 536/24.1 |
| 5,489,520 | 2/1996 | Adams et al. | 435/172.3 |
| 5,641,876 | 6/1997 | McElroy et al. | 536/24.1 |

FOREIGN PATENT DOCUMENTS

| | | |
|---|---|---|
| 0 452 269 | 10/1991 | (GB) . |
| WO 91 09948 | 7/1991 | (WO) . |

OTHER PUBLICATIONS

Callis et al., "Introns increase gene expression in cultured maize cells," *Genes Dev.*, 1:1183–1200, 1987.

Cretin and Puigdomenech, "Glycine–rich RNA–binding proteins from *Sorghum vulgare*," *Plant Mol. Biol.*, 15(5):783–785, 1990.

Gomez et al., "A gene induced by the plant hormone abscisic acid in response to water stress encodes a glycine–rich protein," *Nature*, 334:262–264, 1988.

Kyozuka et al., "Light regulated and cell–specific expression of tomato rbcS–gusA and rice rbcS–gusA fusion genes in transgenic rice," *Plant Physiol.*, 102:991–1000, 1993.

McElroy et al., "Construction of expression vectors based on the rice actin 1 (Act 1) 5' region for use in monocot transformation," *Mol. Gen. Genet.*, 231:150–160, 1991.

McElroy et al., "Characterization of the rice (*Oryza sativa*) actin gene family," *Plant Mol. Biol.*, 15:257–268, 1990b.

McElroy et al., "Structural characterization of a rice (*Oryza sative*) actin gene," *Plant Mol. Biol.*, 14:163–171, 1990.

McElroy et al., "Isolation of an efficient actin promoter for use in rice transformation," *Plant Cell*, 2:163–171, 1990a.

Minobe and Sasaki, "Rice cDNA from root" DATABASE EMBL SEQUENCE LIBRARY Online!, XP002149661, 1993.

Schunmann and Ougham, "Identification of three cDNA clones expressed in the leaf extension zone and with altered patterns of expression in the slender mutant of barley: a tonoplast intrinsic protein, a putative structural protein and protochlorophyllide oxidoreductase" DATABASE EMBL SEQUENCE LIBRARY Online!, XP002149660, 1994.

Meagher, "Divergence and differential expression of actin gene families in higher plants," *Int. Rev. Cytol.*, 125:139–163, 1991.

Poulsen et al., "Characterization of an RBC–S gene from *Nicotiana plumbaginifolia* and expression of an RBC–S–CAT chimeric gene in homologous and heterologous nuclear background," *Mol. Gen. Genet.*, 205(2):193–200, 1986.

Reece et al., "Genomic nucleotide sequence of four rice (*Oryza sativa*) actin genes," *Plant Mol. Biol.*, 14:621–624, 1990.

Spencer et al., "Segregation of transgenes in maize," *Plant Molecular Biology*, 18:201–210, 1992.

Vasil et al., "Increased gene expression by the first intron of maize shrunken–1 locus in grass species", *Plant Physiol*, 91:1575–1579, 1989.

Wang et al., "Characterization of cis–acting elements regulation transcription from the promoter of a constitutively active rice actin gene," *Molecular and Cellular Biology*, 12(8):3399–3406, 1992.

(List continued on next page.)

Primary Examiner—David T. Fox
Assistant Examiner—Medina A. Ibrahim
(74) *Attorney, Agent, or Firm*—Fulbright & Jaworski LLP

(57) ABSTRACT

The current invention provides the maize RS81 promoter. Compositions comprising this sequence are described, as are plants transformed with such compositions. Further provided are methods for the expression of transgenes in plants comprising the use of these sequences. The methods of the invention include the direct creation of transgenic plants with the RS81 promoter by genetic transformation, as well as by plant breeding methods. The sequences of the invention represent a valuable new tool for the creation of transgenic plants, preferably having one or more added beneficial characteristics.

66 Claims, 5 Drawing Sheets

OTHER PUBLICATIONS

Zhang et al., "Analysis of rice Act1 5' region activity in transgenic rice plants," *Plant Cell,* 3(11):1155–1165, 1991.

"*O. sativa* RAc3 gene for actin.," www.ncbi.nlm.nih.gov, accession #X15863, Apr. 7, 1993.

"*O. sativa* RAc3 gene for actin.," www.ncbi.nlm.nih.gov, accession #X15862, Apr. 7, 1993.

"*O. sativa* RAc3 gene for actin.," www.ncbi.nlm.nih.gov, accession #X15865, Apr. 7, 1993.

"*O. sativa* RAc3 gene for actin.," www.ncbi.nlm.nih.gov, accession #X15864, Apr. 7, 1993.

McElroy et al., "Development of gusA reporter gene constructs for cereal transformation," *Mol. Breed.,* 1:27–37, 1995.

Reese, "The actin gene family of rice (*Oryza sativa L*)," Ph.D. thesis, Cornell University, Ithaca, NY, 1988.

```
GTCAACGGAT CACATAGCTA GCGTCTGATT CCATGTGAAA TACTTTTTTT      50
CCCGAACACA TGATATCCCC ATTTTCATTC ATTTCGGATC ATTTGAATTG     100
AATTACATTC TAATAATTAT AATTTAGACA CATATTAATT AAGCTAATAT     150
GATTCTATGC GGAATATATT TGTAAATGCT CGTAATATAT TTTAAGCACT     200
GTTTTAGATT TAAAAGTTCT CTTTCGACCT TCAGCGTTCT GTCATTTTGT     250
TAAGGCTAAG GTGGATCTAA AGTTTTGCAG GGAGCTAGTG TCAAGGAAGA     300
CCTAATACTT CCACTCACGA NGAGCAACTA GGCAAGCCAC ACCCTTATAA     350
AAAAAAGGCA AACCAGACAG TCANANAGAC AGGGGCTCTT CCGCCAACTG     400
GACCTTGATG TTGCCAGTCA TGCGCTGAAA GATTCCAAAT CCTCAATCGC     450
ANACTGCCTT GTCAATCATT TTTTGCATTA AGGNTAAAGC GATAAGGTAA     500
ACAACCATTG GARTNKTKGT TAACANCANC CTGGCACGGC CGGATGCNTN     550
NTNTGAATAA TANTNNGGGG NCAAGACAGG AANNCNTAAT NTTTGGAAAT     600
TTTAGTGGNT AGGAGTCACT GATCATGGAC NTAAGAGTGC TAACCCACTG     650
CATTANCAAA AANCGTGTGG GTGTTGCGGN TTCCAANTTG TCCGTTGTCA     700
CGGNATGGTA TGAATATGCC AAAGATTCTC GCTGTTTTGT GAAATTTAGA     750
TGAGCTGAGC ATGACAAAAG CGCAAACCTT AATTGCATTG CCTACTCCAT     800
ATATGGCAAG ATGGCTTGCA TGACAAAATT AGATGTTAAC AAAAAGAAAA     850
CAAGGAGAAG GTATAGAGGT GCTCGAAAGA CTCGTTGACA CTTTAAACTC     900
GGGTGTGCGT GTGTTATGTG TTTATCTGCT GTATTCAGAA CGGCTCGTCA     950
TAATAGCGTA CATATATATA TATATATGAT CCAATTTTGA AAGTACTAGA    1000
TAAATATAAG ATACTATGCA TTTAAACTAT ATTATAGTCT TATACTCTTA    1050
TCTTAGAACC GGAACCGTCC TATACATTAT CTCTTAATAG CCTCTCCCTC    1100
AATCTTAATC TTCTCTAGGT TTAGATTATG GTTAGATCGA ATTCTCTACT    1150
AATCTTACGA ATAAAGCTTT AGTAAATCAG CCAACCACNT CATTCTTTNG    1200
AATAAACAAA ATCAATCTCA AGCATTCTTA TAAAAACTCT TTCTCGAACA    1250
AATTGATAAC CAAATTCTAT ATGCTTTATT ATNGGCDTGG AACAAACGAA    1300
TTAGATNACA AATATNTTTT GCATATCATG CGCGCGCHAG TGATGTTTTA    1350
CTTTTACTCN TCGGTCACAG GGTTTHGCCT CCTTGAAWTC GAAAGGGGAA    1400
TACTGAMTGG CCAAATTGCT TATGGAGTTG TTAAAGAATA CAAAAATAGG    1450
TGCCGAAAGG GTTTGCTCTA ATGATTTGAT GAAGTCGTTG CCMCCGATGG    1500
TTACCATGCA GTACTACTAC TATCATAGTG TCATGGTTTT TTTATTTTCA    1550
ATTGCTGTAC TGATGCAGAC GTGACGCATG CGTTTACTAT CCTTGCAGCC    1600
ACCGACTCCA AAATGAAGAG AGCTAGCGCT CAATTCATTG GTCCACGTCA    1650
CCATCAACGT TCCGAACTGT CTCGCATGCA TCGTGCCGAG AAAAAGAGCA    1700
CCGATGACNA TGGATGCGAT CGADTTCCCA CCATTTGAGA GCAATATGCG    1750
TTTTACACTT TACAACAAGG TACAAGTGAA ACAATAAACC ATGCTAAATA    1800
AAAGCGCTAA GGGCTGATTT GGTGGCCCAG AATCACGGGA GGATTGGAGG    1850
GGATTGAGAG AGAAATTAGT TCATTTCCTC CTCAATCATC TACAATTCTC    1900
TCGTGATTCT ACTTATCACC AAATCAATCT AAAACTTACG TCTCTCCTGC    1950
TGCGCTCTCG CACCACACTG CAGGAACGTA CGCCCGGCCG AGGCTGCAAC    2000
TGAAATGGAA GTATGAAACC CTTCGGCTTT TGTTTCCTGA TTGACCAACT    2050
GTGACAAATC CCCTAGCATT TTGCAAGAAC AACTACATAG ACGTTGAGAT    2100
AACATATATA TCCTCCAAAC GAGACAGCCC ATCTGACAAC ACTTGCAGCC    2150
GTTCGAACGT TNCCATTACC AAAATATTTA AGCGTTACAC AAGAGATAGC    2200
GTACCTCCAA TGATTAGCGG CTTTGCCGTT TATTATTGTC ATTGGCGCAT    2250
TGCTTTGGTG TACCTCACAT GGACACGCCA TGAAAGATG  ACAATAGCGC    2300
AAACAGACAT CCGAACAAAG CTTGGTGCGC CTGCTCTCGG CCGGGCTAGC    2350
TAGTACCAAT CATGGAATAA TAAGCTAGTA TATATATACC GCCCCATTTA    2400
TAAAAATGTA AATAAAATGT TCTGTGGCGA TTATGCACAC CGTCCATAAT    2450
ACTCTAGTCG TCGGCAAGCT GAGGCCGCCC ATTAAGCCTT GAGCGTGTAT    2500
AAAAGGGGCA TAGACTCCCA GCATCAGCGA AGCAGCAACA TATCAAGCTC    2550
AGAGCCTCAG AGCGCCAGCC AAGTCTTGCG GTCG                     2584
```

FIG. 1

G GGC TGC GAG GAGTCT GGT GGC ACC TAA GCCGT CATCG TCATA TATG CCTCG
TTTAA T TGTTC ATCTC TGATT CGATG ATGTC TCCCA CCTTG TTTCG TGTGT
TCCCA GTTTG TTCAT CGTCT TT TGATT TTACC GGCCG TGCTC TGCTT TTGTT
TTTGT TTCAC CTGAT CTCTC TCTGA CTTGA TGTAA GA GTGGT ATCTG CTACG
ACTAT ATGTT GTTGG GTGAG GCATA TGTGA ATGAA ATMTA TGRAA GCTCC GG
CTATA TATAT TTATA CAAAG GGTAT GAGAT GGATG TGAAT CTAGA GCATA
TGTGT CCAAC AATCA AT TCG

FIG. 2

```
gaattcccgg acctccatgc ctacatcaac taatttgatt ccttgagttt      50
acgtttagtg atatgtctat ttttagagct tgttggggct tcggcctcag     100
ctctagccag ccaaacatgt tctaccaagt accctatgtt ggcatgatat     150
agtgatgcat tataacaata aatgagcgag ggattgctgg ctgaaaaagc     200
tatactagct gcatttggtt atagttaacc gaactattaa ttgcgtgtac     250
aacaaaataa aaaaaatgca tgttgcacat tctttcatta acattatgtt     300
ttggtagtgt gaattagaaa tttgattgac agtagatcga caaacatagt     350
ttcaatatgc ttaagttagt tatgacttta acatatcagt ctccttgata     400
ttttcgtttt agattcgtct ctctactagt gtgtatgtcc accttccata     450
gcagtgaagg gttccattcc atccctggta aaaaaaaatc aaccactact     500
atttatttcc taaaaagcaa aatgataaaa tatcattttt ttaataaaaa     550
taaaaaaatt ttggggtaca taattgatgt tgccccttgg gattaacctt     600
aaaaagggc gaatttcta gggtttggcc aagttttgca atgcaccaaa      650
ttattcccct tgggccggcc gccacccaa aaaaaccccc aacccccaac     700
tttccattga aggccgggcc cccttaaatc ctcatccccc caaTTTCCAC     750
CACCATCGCC ATTGCCACCA CCTCTCCTAT ATCTCGCCCT CCCCCTCCTC     800
CCTCCCACGC CATTCGCCTC CTTCTTGCTG CAGCCGCCAT CCCCGGTTCG     850
GTTCTCTCCT ctctttagg tgagcaactg cctctccatg tccaggccct      900
cccggccccy gsktgswtty tgktttaawg skkgakgttt ytkgcaaats     950
ggarrkgttt tmkwtttctg ttarrwgggk ggaaawackg aackgarttg    1000
ctgaaaktag gkgttggctg ggtkgctttt ggctkgtawg ttgtcaaakg    1050
ttggawccgt tggamtgtag gragttcagg grakssscsta aacnggtgtt   1100
gtttctgggg gatgctgatc cgatccgatg gcttttagtn gatggaagta    1150
tccgatcttg tttgtgctga ggtgacgagt attcttgcag tagatctttt    1200
tcgtgtttat gttgtgttgt gctaaggtct tgtagttccc aaaatttttt    1250
ccccaaaaat gtcaacatgg tatctttaga cacatgaata gagcattaaa    1300
tatagattaa aaaaaactaa ttgcacaatt tgcatggaaa atcgtgagac    1350
caatcttta agcctaatta gtccatgatt agacataagt gctacagtaa    1400
cccacgtgtg ctaatgatgg attaattagg cttaataaat tcgtctctca    1450
gttttctagg cgagctatga aattaatttt ttttattcgt gtccgaaaat    1500
cccttccgac atccggttaa acgtcggatg tgacaagaaa aattttcttt    1550
tcgcgaacta aacaaggcct aaggcgtgaa gttgggggta tgtttacttt    1600
gaattgtaga tcaactgaca gacttttgca tgctcatagc cggtttgttt    1650
gcggtactca agaaactgtc ttgattggtc attccgtagg gtggggactk    1700
gkgaaaaagc tgattccttt cttttcattt ccacggttgc tttcttggtt    1750
ggcgtgggaa aaaaacagtt ttcagtactg taccgatcga ctttcttttg    1800
agacttttt ctccttcaac aaaacatttc atagttcaca caaaaacaca     1850
agcataccaa cgatttcatt atgtgacatg gcttctaaaa tctgaattaa    1900
agaagcaagt tgcttaactg aaaactgcct agtttcagaa atcatggagt    1950
ttaaatttc caaagagaag ggtaacatat tatggagaac tagaattttg     2000
ttactaaaaa atgtatgctt atgggaccac tattctaaga tgcttcacat    2050
```

FIG. 3

```
cttgatgacg gctgtctgat cagaaaaaaa ataatgcttc agatcaacca      2100
atcagacaat ccaggatatg agcagatcat gttgcattca ttycatccac      2150
tgaagcangt cccnannttc ttccccctgaa gattggtcta aatcgattca     2200
taaaacacat tgcatgtatg cttcttagga gagagcacca ttcccttttgg    2250
agggttggtg attcagacca gcctcggttg attgatttga atttcttaac     2300
tacaagtcac ttgatctagt tataatttac gcatcatgga ccattcattt     2350
tgggagtttc ctatatacaa ctaaagtgtt atacttcttc ctatctgcgc     2400
cttccttttt gtttgaataa tcctccctct ttcacaattt gcaatactag     2450
ttagtcaatt aatagctttg aatgtgatat cttaaagaca tgtatttttgt   2500
cattcatgtt tgatgaagac tcgtgttttt gtaggatgaa tgtttagttc     2550
aagttacatt tttctgtatt aatctatagt ctttgtaaac actgttttga     2600
atgatttatt ttgtgttatg cagATCAGTT AGGTACCATG                2640
```

FIG. 3 (continued)

MAIZE RS81 PROMOTER AND METHODS FOR USE THEREOF

BACKGROUND OF THE INVENTION

1. Field of the Invention

The present invention relates generally to transgenic plants. More specifically, it relates to methods and compositions for transgene expression using the maize RS81 promoter.

2. Description of the Related Art

An important aspect in the production of genetically engineered crops is obtaining sufficient levels of transgene expression in the appropriate plant tissues. In this respect, the selection of promoters for directing expression of a given transgene is crucial. Promoters which are useful for plant transgene expression include those that are inducible, viral, synthetic, constitutive as described (Poszkowski et al., 1989; Odell et al., 1985), temporally regulated, spatially regulated, and spatio-temporally regulated (Chau et al., 1989).

A number of plant promoters have been described with various expression characteristics. Examples of some constitutive promoters which have been described include the rice actin 1 (Wang et al., 1992; U.S. Pat. No. 5,641,876), CaMV 35S (Odell et al., 1985), CaMV 19S (Lawton et al., 1987), nos (Ebert et al., 1987), Adh (Walker et al., 1987), sucrose synthase (Yang & Russell, 1990).

Examples of tissue specific promoters which have been described include the lectin (Vodkin et al., 1983; Lindstrom et al., 1990), corn alcohol dehydrogenase 1 (Vogel et al., 1989; Dennis et al., 1984), corn light harvesting complex (Simpson, 1986; Bansal et al., 1992), corn heat shock protein (Odell et al., 1985; Rochester et al., 1986), pea small subunit RuBP carboxylase (Poulsen et al., 1986; Cashmore et al., 1983), Ti plasmid mannopine synthase (Langridge et al., 1989), Ti plasmid nopaline synthase (Langridge et al., 1989), petunia chalcone isomerase (Van Tunen et al., 1988), bean glycine rich protein 1 (Keller et al., 1989), truncated CaMV 35s (Odell et al., 1985), potato patatin (Wenzler et al., 1989), root cell (Conkling et al., 1990), maize zein (Reina et al., 1990; Kriz et al., 1987; Wandelt and Feix, 1989; Langridge and Feix, 1983; Reina et al., 1990), globulin-1 (Belanger and Kriz et al., 1991), α-tubulin, cab (Sullivan et al., 1989), PEPCase (Hudspeth & Grula, 1989), R gene complex-associated promoters (Chandler et al., 1989), and chalcone synthase promoters (Franken et al., 1991).

Inducible promoters which have been described include ABA- and turgor-inducible promoters, the promoter of the auxin-binding protein gene (Schwob et al., 1993), the UDP glucose flavonoid glycosyl-transferase gene promoter (Ralston et al., 1988); the MPI proteinase inhibitor promoter (Cordero et al., 1994), and the glyceraldehyde-3-phosphate dehydrogenase gene promoter (Kohler et al., 1995; Quigley et al., 1989; Martinez et al., 1989).

A class of genes which are expressed in an inducible manner are glycine-rich proteins. Expression of glycine rich proteins is induced by the plant hormone abscibic acid (ABA). Genes encoding glycine rich proteins have been described, for example, from maize (Didierjean et al., 1992; Gomez et al., 1988; Baysdorfer, Genbank Accession No. AF034945) sorghum (Cretin and Puigdomenech, 1990), and rice (Lee et al., Genbank Accession No. AF009411).

In addition to the use of a particular promoter, expression of transgenes can be influenced by other types of elements. In particular, introns have demonstrated the potential for enhancing transgene expression. For example, Callis et al. (1987) described an intron from the corn alcohol dehydrogenase gene which is capable of enhancing the expression of transgenes in transgenic plant cells. Similarly, Vasil et al. (1989) described an intron from the corn sucrose synthase gene having similar enhancing activity. The rice actin 1 intron, in particular, has found wide use in the enhancement of transgene expression in a number of different transgenic crops (McElroy et al., 1991). This 5' intron was identified from the first coding exon of the rice actin 1 sequence (McElroy et al., 1990). Plant actin is encoded by a gene family present in all plant species studied to date (Meagher, 1991). In rice, there are at least eight actin-like sequences per haploid genome. Four of the rice actin coding sequences (rice actin 1, 2, 3 and 7) have been isolated and shown to differ from each other in the tissue and stage-specific abundance of their respective transcripts (Reece, 1988; McElroy et al., 1990a; Reece et al., 1990; U.S. Pat. No. 5,641,876; Genbank Accession numbers X15865, X15864, X15862, and X15863, respectively).

While the above studies have provided a number of useful tools for the generation of transgenic plants, there is still a great need in the art for novel promoter and enhancer sequences with beneficial expression characteristics. In particular, there is a need in the art for promoter-enhancer combinations which are capable of directing high-level expression of exogenous genes in transgenic crop plants. Many previously identified regulatory sequences fail to provide the levels of expression required to fully realize the benefits potentially conferred by expression of selected genes in transgenic plants. Additionally, many regulatory regions fail to demonstrate suitable or desirable expression profiles for transgene expression. There is, therefore, a great need in the art for the identification of novel sequences which can be used for the high-level expression of selected transgenes in economically important crop plants.

SUMMARY OF THE INVENTION

In one aspect, the invention provides an isolated nucleic acid comprising a maize RS81 promoter. Also provided by the invention is a maize RS81 promoter isolatable from the nucleic acid sequence of SEQ ID NO:1. The RS81 promoter may, in particular embodiments of the invention, comprise from about 50 to about 2584, from about 150 to about 2584, from about 250 to about 2584, from about 400 to about 2584, from about 750 to about 2584, from about 1000 to about 2584, from about 1500 to about 2584, or from about 2000 to about 2584, contiguous nucleotides of the nucleic acid sequence of SEQ ID NO:1. The maize RS81 promoter provided by the invention may further comprise the nucleic acid sequence of SEQ ID NO:1. In particular embodiments of the invention, the maize RS81 promoter may further comprise an enhancer, including an intron such as the rice actin 1 intron or the rice actin 2 intron. An RS81 promoter used in accordance with the invention may further include a terminator, for example, an rbcS terminator.

In another aspect, the invention provides an expression cassette comprising a maize RS81 promoter operably linked to a selected DNA. Potentially any selected DNA may be included with the expression cassette, including those encoding an insect resistance protein, a bacterial disease resistance protein, a fungal disease resistance protein, a viral disease resistance protein, a nematode disease resistance protein, a herbicide resistance protein, a protein affecting grain composition or quality, a nutrient utilization protein, a mycotoxin reduction protein, a male sterility protein, a selectable marker protein, a screenable marker protein, a negative selectable marker protein, an environment or stress resistance protein, or a protein affecting plant agronomic characteristics. The expression cassette may further include any suitable selectable marker protein. Examples of suitable selectable marker proteins include phosphinothricin acetyltransferase, glyphosate resistant EPSPS, aminoglycoside phosphotransferase, hygromycin phosphotransferase, dalapon dehalogenase, bromoxynil resistant nitrilase, anthranilate synthase and glyphosate oxidoreductase.

An expression cassette may further comprise an enhancer. In particular embodiments of the invention, the enhancer is selected from the group consisting of the rice actin 1 intron and the rice actin 2 intron. The expression cassette may still further comprise a transit peptide coding sequence, for example, a transit peptide selected from the group consisting of chlorophyll a/b binding protein transit peptide, small subunit of ribulose bisphosphate carboxylase transit peptide, EPSPS transit peptide and dihydrodipocolinic acid synthase transit peptide. In the expression cassette, the selected coding sequence may be operably linked to potentially any terminator, for example, a rice or other type of rbcS terminator.

In yet another aspect, the invention provides an expression vector comprising a maize RS81 promoter operably linked to a selected coding region. In one embodiment of the invention, the expression vector may be further defined as a plasmid vector. In another embodiment of the invention, the plasmid vector may be located within a bacterial cell.

In still yet another aspect, the invention provides a fertile transgenic plant which is stably transformed with a selected DNA comprising a maize RS81 promoter. In particular embodiments of the invention, the fertile transgenic plant comprises a maize RS81 promoter which is isolatable from the nucleic acid sequence of SEQ ID NO:1. In other embodiments of the invention, the fertile transgenic plant has a maize RS81 promoter comprising from about 50 to about 2584, from about 100 to about 2584, from about 200 to about 2584, from about 400 to about 2584, from about 750 to about 2584, from about 1000 to about 2584, from about 1500 to about 2584, or from about 2000 to about 2584, contiguous nucleotides of the nucleic acid sequence of SEQ ID NO:1. The fertile transgenic plant may also comprise the nucleic acid sequence of SEQ ID NO:1. In the fertile transgenic plant, the selected DNA may further comprise a selected coding region operably linked to said maize RS81 promoter.

The selected coding region may be potentially any protein, for example, an insect resistance protein, a bacterial disease resistance protein, a fungal disease resistance protein, a viral disease resistance protein, a nematode disease resistance protein, a herbicide resistance protein, a protein affecting grain composition or quality, a nutrient utilization protein, an environment or stress resistance protein, a mycotoxin reduction protein, a male sterility protein, a selectable marker protein, a screenable marker protein, a negative selectable marker protein, or a protein affecting plant agronomic characteristics.

Where a selected protein used in accordance with the invention is a selectable marker protein, it may be preferable to utilize a protein selected from the group consisting of phosphinothricin acetyltransferase, glyphosate resistant EPSPS, aminoglycoside phosphotransferase, hygromycin phosphotransferase, neomycin phosphotransferase, dalapon dehalogenase, bromoxynil resistant nitrilase, anthranilate synthase and glyophosate oxidoreductase. In further embodiments of the invention, the selected coding region is operably linked to a terminator, for example, a rice or other rbcS terminator. The selected DNA may also comprise an enhancer, such as a rice actin 1 intron or rice actin 2 intron. The selected DNA may comprise plasmid DNA and/or a transit peptide. In particular embodiments of the invention, the transit peptide is selected from the group consisting of chlorophyll a/b binding protein transit peptide, small subunit of ribulose bisphosphate carboxylase transit peptide, EPSPS transit peptide and dihydrodipocolinic acid synthase transit peptide.

In one embodiment of the invention, a fertile transgenic plant prepared in accordance with the invention is further defined as a monocotyledonous plant, for example, a monocot selected from the group consisting of wheat, maize, rye, rice, oat, barley, turfgrass, sorghum, millet and sugarcane. The fertile transgenic plant also may be a dicotyledonous plant, for example, a tobacco, tomato, potato, soybean, cotton, canola, alfalfa or sunflower plant. In one embodiment of the invention, the plant is a soybean plant.

In still yet another aspect, the invention provides a fertile $R_0$ transgenic plant comprising a transgenic RS81 promoter. Also provided are seeds of the $R_0$ transgenic plant, wherein the seeds comprise a selected DNA including the RS81 promoter. Further provided are progeny plants of any generation of the $R_0$ transgenic plant, wherein said $R_0$ transgenic plant comprises said selected DNA, as well as seeds of the progeny plants, wherein said seed comprises said selected DNA.

In still yet another aspect, the invention provides a crossed fertile transgenic plant prepared according to the method comprising the steps of: (i) obtaining a fertile transgenic plant comprising a selected DNA comprising a maize RS81 promoter; (ii) crossing said fertile transgenic plant with itself or with a second plant lacking said selected DNA to prepare the seed of a crossed fertile transgenic plant, wherein said seed comprises said selected DNA; and (iii) planting said seed to obtain a crossed fertile transgenic plant. The invention also provides a seed of the crossed fertile transgenic plant, wherein said seed comprises said selected DNA. In one embodiment of the invention the crossed fertile transgenic plant is a monocotyledonous plant, including a wheat, oat, barley, maize, rye, rice, turfgrass, sorghum, millet or sugarcane plant. The crossed fertile transgenic plant may also be a dicotyledonous plant, including a tobacco, tomato, potato, soybean, canola, alfalfa, sunflower or cotton plant. The selected DNA may be inherited through a male or female parent. In one embodiment of the invention, the second plant is an inbred plant, and the crossed fertile transgenic plant is a hybrid. In particular embodiments of the invention, said maize RS81 promoter is isolatable from the nucleic acid sequence of SEQ ID NO:1. In further embodiments of the invention, the maize RS81 promoter comprises from about 50 to about 2584, from about 100 to about 2584, from about 200 to about 2584, from about 400 to about 2584, from about 750 to about 2584, from about 1000 to about 2584, from about 1500 to about 2584, or from about 2000 to about 2584 contiguous nucleotides of the nucleic acid sequence of SEQ ID NO:1. The maize RS81 promoter may also comprise the nucleic acid sequence of SEQ ID NO:1.

The crossed fertile transgenic plant may comprise a selected DNA comprising a selected coding region operably linked to the aforementioned maize RS81 promoter. In particular embodiments of the invention, the selected protein is selected from the group consisting of insect resistance protein, a bacterial disease resistance protein, a fungal disease resistance protein, a viral disease resistance protein, a nematode disease resistance protein, a herbicide resistance protein, a protein affecting grain composition or quality, a nutrient utilization protein, a mycotoxin reduction protein, a male sterility protein, a selectable marker protein, a screenable marker protein, a negative selectable marker protein, a protein affecting plant agronomic characteristics, and an environment or stress resistance protein. The selected DNA may also comprise an enhancer, such as a rice actin 1 intron or rice actin 2 intron. The selected protein may be operably linked to a terminator, for example, a rice or other rbcS terminator.

In still yet another aspect, the invention provides a method of expressing a selected protein in a transgenic plant comprising the steps of: (i) obtaining a construct comprising a selected coding region operably linked to a maize RS81 promoter; (ii) transforming a recipient plant cell with said construct; and (iii) regenerating a transgenic plant expressing said selected protein from said recipient plant cell. In one embodiment of the invention, the step of transforming comprises a method selected from the group consisting of microprojectile bombardment, PEG mediated transformation of protoplasts, electroporation, silicon carbide fiber mediated transformation, or Agrobacterium-mediated transformation. In another embodiment the recipient plant cell is from a monocotyledonous plant, including a wheat, maize, rye, rice, turfgrass, oat, barley, sorghum, millet, or sugarcane plant. In further embodiments, the recipient plant cell is from a dicotyledonous plant, including a tobacco, tomato, potato, soybean, canola, sunflower, alfalfa or cotton plant. The selected protein can be any protein, for example, an insect resistance protein, a bacterial disease resistance protein, a fungal disease resistance protein, a viral disease resistance protein, a nematode disease resistance protein, a herbicide resistance protein, a protein affecting grain composition or quality, a nutrient utilization gene, a mycotoxin reduction protein, a male sterility protein, a selectable marker protein, a screenable marker protein, a negative selectable marker gene, a gene affecting plant agronomic characteristics, or an environment or stress resistance protein. The construct also may comprise an enhancer, for example, a rice actin 1 intron or rice actin 2 intron. The selected coding region also may be operably linked to a terminator, for example, a rice or other rbcS terminator.

In still yet another aspect, the invention provides a method of plant breeding comprising the steps of: (i) obtaining a transgenic plant comprising a selected DNA comprising a maize RS81 promoter; and (ii) crossing said transgenic plant with itself or a second plant. In one embodiment of the invention, the transgenic plant is a monocotyledonous plant, for example, a wheat, maize, oat, barley, rye, rice, turfgrass, sorghum, millet or sugarcane plant. In another embodiment of the invention, the transgenic plant is a dicotyledonous plant, for example, a tobacco, tomato, potato, soybean, canola, sunflower, alfalfa or cotton plant. In still another embodiment of the invention, the maize RS81 promoter is isolatable from the nucleic acid sequence of SEQ ID NO:1. The maize RS81 promoter may also comprise from about 100 to about 2584, from about 150 to about 2584, from about 250 to about 2584, from about 400 to about 2584, from about 600 to about 2584, from about 800 to about 2584, from about 1000 to about 2584, from about 1500 to about 2584, or from about 2000 to about 2584 contiguous nucleotides of the nucleic acid sequence of SEQ ID NO: 1. The maize RS81 promoter may also comprise the nucleic acid sequence of SEQ ID NO:1.

In the method of plant breeding, the transgenic plant may be crossed with said second plant, and said second plant may be an inbred plant. The method may also further comprise the steps of: (iii) collecting seeds resulting from said crossing; (iv) growing said seeds to produce progeny plants; (v) identifying a progeny plant comprising said selected DNA; and (vi) crossing said progeny plant with itself or a third plant. In the method, said progeny plant may inherit the selected DNA through a male or female parent. In one embodiment of the invention, the second plant and said third plant are of the same genotype, and may be inbred plants.

The selected DNA may further comprise potentially any protein, including an insect resistance protein, a bacterial disease resistance protein, a fungal disease resistance protein, a viral disease resistance protein, a nematode disease resistance protein, a herbicide resistance protein, a protein affecting grain composition or quality, a nutrient utilization protein, a mycotoxin reduction protein, an environment or stress resistance protein, a male sterility protein, a selectable marker protein, a screenable marker protein, a negative selectable marker protein, or a protein affecting plant agronomic characteristics. The selected DNA may further comprise a genetic element which enhances the expression of said protein in said transgenic plant, for example, a rice actin 1 intron or rice actin 2 intron.

BRIEF DESCRIPTION OF THE DRAWINGS

FIG. 1: Sequence of the 5' region of the maize RS81 gene. (SEQ ID NO:1)

FIG. 2: Sequence of the 3' end of the rice rbcS sequence (SEQ ID NO:2). Transcribed nucleotides are underlined. The polyadenylation signal is given by bold nucleotides.

FIG. 3: Sequence of the 5' region of the rice actin 2 gene (SEQ ID NO:3). The actin 2 intron (SEQ ID NO:4) is indicated by lowercase italicized nucleotides, uppercase nucleotides indicate the actin 2 exon 1, lower case nucleotides indicate the actin 2 promoter, upper case italics indicate the actin 2 exon 2, and upper case bold italics indicate the actin 2 translation initiation codon.

FIG. 4A: Safranin O counterstaining of root tissue; FIG. 4B: Histological detection of GUS expression.

DETAILED DESCRIPTION OF THE INVENTION

Figures 4A, 4B:
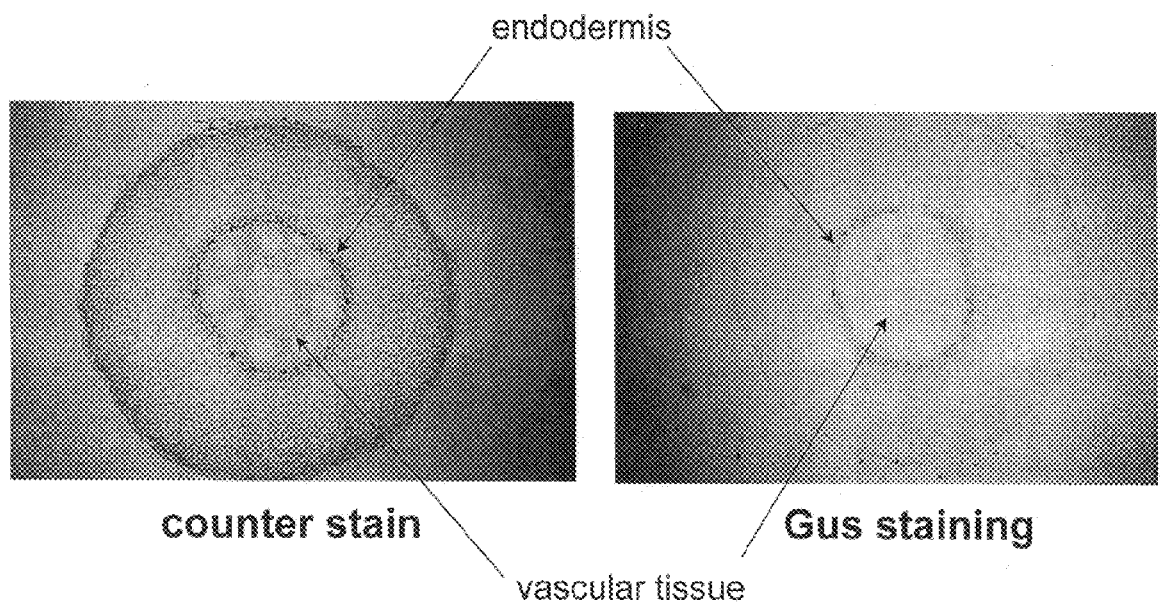
FIG. 4A, 4B: Histological detection of RS81-directed GUS expression in root endodermis.

The current invention overcomes deficiencies in the prior art by providing novel methods and compositions for the efficient expression of transgenes in plants. In particular, the current invention provides the RS81 promoter. The RS81 promoter described herein represents a root-specific promoter which may find wide utility in directing the expression of potentially any gene which one desires to have expressed in a plant. This promoter represents a significant advance in that it is capable of directing high-level expression of transgenes in plants.

The RS81 promoter sequence of the invention is exemplified by the nucleic acid sequence given in SEQ ID NO:1. However, in addition to the unmodified RS81 promoter sequence of SEQ ID NO:1, the current invention includes derivatives of this sequence and compositions made therefrom. In particular, the present disclosure provides the teaching for one of skill in the art to make and use derivatives of the RS81 promoter. For example, the disclosure provides the teaching for one of skill in the art to delimit the functional elements within the RS81 promoter and to delete any non-essential elements. Functional elements also could be modified to increase the utility of the sequences of the invention for any particular application. For example, a functional region within the RS81 promoter of the invention could be modified to cause or increase tissue-specific expression. Such changes could be made by site-specific mutagenesis, techniques, for example, as described below.

One important application of the RS81 promoter will be in the construction of vectors designed for introduction into plants by genetic transformation. By including an actin 1 intron or actin 2 intron with such transformation constructs comprising an RS81 promoter, one may increase the level of expression of coding regions operably linked to the RS81 promoter. It is also believed that benefit will be obtained by including a transcriptional terminator with transgenes operably linked to the RS81 promoter. More particularly, benefit may be realized by including a terminator from a gene encoding the small subunit of a ribulose-1,5-bisphosphate carboxylase-oxygenase (Rubisco), and more specifically, from a rice Rubisco gene.

I. Derivatives of the Sequences of the Invention

An important aspect of the invention provides derivatives of the maize RS81 promoter. In particular, the current invention includes sequences which have been derived from the maize RS81 promoter disclosed herein. One efficient means for preparing such derivatives comprises introducing mutations into the sequences of the invention, for example, the sequence given in SEQ ID NO:1. Such mutants may potentially have enhanced or altered function relative to the native sequence or alternatively, may be silent with regard to function.

Mutagenesis may be carried out at random and the mutagenized sequences screened for function in a trial-by-error procedure. Alternatively, particular sequences which provide the RS81 promoter with desirable expression characteristics could be identified and these or similar sequences introduced into other related or non-related sequences via mutation. Similarly, non-essential elements may be deleted without significantly altering the function of the elements. It further is contemplated that one could mutagenize these sequences in order to enhance their utility in expressing transgenes in a particular species, for example, in maize.

The means for mutagenizing a DNA segment encoding an RS81 promoter sequence of the current invention are well-known to those of skill in the art. Mutagenesis may be performed in accordance with any of the techniques known in the art, such as, and not limited to, synthesizing an oligonucleotide having one or more mutations within the sequence of a particular regulatory region. In particular, site-specific mutagenesis is a technique useful in the preparation of promoter mutants, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids also are routinely employed in site directed mutagenesis which eliminates the step of transferring the gene of interest from a plasmid to a phage.

Site-directed mutagenesis in accordance herewith typically is performed by first obtaining a single-stranded vector or melting apart of two strands of a double stranded vector which includes within its sequence a DNA sequence which encodes the maize RS81 promoter. An oligonucleotide primer bearing the desired mutated sequence is prepared, generally synthetically. This primer is then annealed with the single-stranded vector, and subjected to DNA polymerizing enzymes such as the *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as *E. coli* cells, and cells are selected which include recombinant vectors bearing the mutated sequence arrangement. Vector DNA can then be isolated from these cells and used for plant transformation. A genetic selection scheme was devised by Kunkel et al. (1987) to enrich for clones incorporating mutagenic oligonucleotides. Alternatively, the use of PCR™ with commercially available thermostable enzymes such as Taq polymerase may be used to incorporate a mutagenic oligonucleotide primer into an amplified DNA fragment that can then be cloned into an appropriate cloning or expression vector. The PCR™-mediated mutagenesis procedures of Tomic et al. (1990) and Upender et al. (1995) provide two examples of such protocols. A PCR™ employing a thermostable ligase in addition to a thermostable polymerase also may be used to incorporate a phosphorylated mutagenic oligonucleotide into an amplified DNA fragment that may then be cloned into an appropriate cloning or expression vector.

The preparation of sequence variants of the selected promoter or intron-encoding DNA segments using site-directed mutagenesis is provided as a means of producing potentially useful species and is not meant to be limiting as there are other ways in which sequence variants of DNA sequences may be obtained. For example, recombinant vectors encoding the desired promoter sequence may be treated with mutagenic agents, such as hydroxylamine, to obtain sequence variants.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" also is intended to refer to a process that involves the template-dependent extension of a primer molecule. The term template-dependent process refers to nucleic acid synthesis of an RNA or a DNA molecule wherein the sequence of the newly synthesized strand of nucleic acid is dictated by the well-known rules of complementary base pairing (see, for example, Watson and Ramstad, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety. A number of template dependent processes are available to amplify the target sequences of interest present in a sample, such methods being well known in the art and specifically disclosed herein below.

One efficient, targeted means for preparing mutagenized promoters or enhancers relies upon the identification of putative regulatory elements within the target sequence. This can be initiated by comparison with, for example, promoter sequences known to be expressed in a similar manner. Sequences which are shared among elements with similar functions or expression patterns are likely candidates for the binding of transcription factors and are thus likely elements which confer expression patterns. Confirmation of these putative regulatory elements can be achieved by deletion analysis of each putative regulatory region followed by functional analysis of each deletion construct by assay of a reporter gene which is functionally attached to each construct. As such, once a starting promoter or intron sequence is provided, any of a number of different functional deletion mutants of the starting sequence could be readily prepared.

As indicated above, deletion mutants of the RS81 promoter also could be randomly prepared and then assayed. With this strategy, a series of constructs are prepared, each containing a different portion of the clone (a subclone), and these constructs are then screened for activity. A suitable means for screening for activity is to attach a deleted promoter construct to a selectable or screenable marker, and to isolate only those cells expressing the marker protein. In this way, a number of different, deleted promoter constructs are identified which still retain the desired, or even enhanced, activity. The smallest segment which is required for activity is thereby identified through comparison of the selected constructs. This segment may then be used for the construction of vectors for the expression of exogenous protein.

II. Plant Transformation Constructs

The construction of vectors which may be employed in conjunction with plant transformation techniques according to the invention will be known to those of skill of the art in light of the present disclosure (see for example, Sambrook et al., 1989; Gelvin et al., 1990). The techniques of the current invention are thus not limited to any particular DNA sequences in conjunction with the RS81 promoter of the invention. For example, the RS81 promoter alone could be transformed into a plant with the goal of enhancing or altering the expression of one or more genes in the host genome.

One important use of the sequences of the invention will be in directing the expression of a selected coding region which encodes a particular protein or polypeptide product. However, the selected coding regions also may be non-expressible DNA segments, e.g., transposons such as Ds that do not direct their own transposition. The inventors also contemplate that, where both an expressible gene that is not necessarily a marker gene is employed in combination with a marker gene, one may employ the separate genes on either the same or different DNA segments for transformation. In the latter case, the different vectors are delivered concurrently to recipient cells to maximize cotransformation.

The choice of the particular selected coding regions used in accordance with the RS81 promoter for transformation of recipient cells will often depend on the purpose of the transformation. One of the major purposes of transformation of crop plants is to add commercially desirable, agronomically important traits to the plant. Such traits include, but are not limited to, herbicide resistance or tolerance; insect resistance or tolerance; disease resistance or tolerance (viral, bacterial, fungal, nematode); stress tolerance and/or resistance, as exemplified by resistance or tolerance to drought, heat, chilling, freezing, excessive moisture, salt stress, or oxidative stress; increased yields; food content and makeup; physical appearance, male sterility; drydown; standability; prolificacy; starch properties; oil quantity and quality, and the like.

In certain embodiments, the present inventors contemplate the transformation of a recipient cell with more than transformation construct. Two or more transgenes can be created in a single transformation event using either distinct selected-protein encoding vectors, or using a single vector incorporating two or more gene coding sequences. Of course, any two or more transgenes of any description, such as those conferring, for example, herbicide, insect, disease (viral, bacterial, fungal, nematode) or drought resistance, male sterility, drydown, standability, prolificacy, starch properties, oil quantity and quality, or those increasing yield or nutritional quality may be employed as desired.

In other embodiments of the invention, it is contemplated that one may wish to employ replication-competent viral vectors for plant transformation. Such vectors include, for example, wheat dwarf virus (WDV) "shuttle" vectors, such as pW1-11 and PW1-GUS (Ugaki et al., 1991). These vectors are capable of autonomous replication in maize cells as well as E. coli, and as such may provide increased sensitivity for detecting DNA delivered to transgenic cells. A replicating vector also may be useful for delivery of genes flanked by DNA sequences from transposable elements such as Ac, Ds, or Mu. It has been proposed that transposition of these elements within the maize genome requires DNA replication (Laufs et al., 1990). It also is contemplated that transposable elements would be useful for introducing DNA fragments lacking elements necessary for selection and maintenance of the plasmid vector in bacteria, e.g., antibiotic resistance genes and origins of DNA replication. It also is proposed that use of a transposable element such as Ac, Ds, or Mu would actively promote integration of the desired DNA and hence increase the frequency of stably transformed cells.

It further is contemplated that one may wish to co-transform plants or plant cells with 2 or more vectors. Co-transformation may be achieved using a vector containing the marker and another gene or genes of interest. Alternatively, different vectors, e.g., plasmids, may contain the different genes of interest, and the plasmids may be concurrently delivered to the recipient cells. Using this method, the assumption is made that a certain percentage of cells in which the marker has been introduced, also have received the other gene(s) of interest. Thus, not all cells selected by means of the marker, will express the other proteins of interest which had been presented to the cells concurrently.

Vectors used for plant transformation may include, for example, plasmids, cosmids, YACs (yeast artificial chromosomes), BACs (bacterial artificial chromosomes) or any other suitable cloning system. It is contemplated that utilization of cloning systems with large insert capacities will allow introduction of large DNA sequences comprising more than one selected gene. Introduction of such sequences may be facilitated by use of bacterial or yeast artificial chromosomes (BACs or YACs, respectively), or even plant artificial chromosomes. For example, the use of BACs for Agrobacterium-mediated transformation was disclosed by Hamilton et al. (1996).

Particularly useful for transformation are expression cassettes which have been isolated from such vectors. DNA segments used for transforming plant cells will, of course, generally comprise the cDNA, gene or genes which one desires to introduced into and have expressed in the host cells. These DNA segments can further include, in addition to an RS81 promoter, structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. However, this may not always be the case, and the present invention also encompasses transgenic plants incorporating non-expressed transgenes. Preferred components likely to be included with vectors used in the current invention are as follows.

(i) Regulatory Elements

Constructs prepared in accordance with the current invention will include an RS81 promoter or a derivative thereof. However, these sequences may be used in the preparation of transformation constructs which comprise a wide variety of other elements. One such application in accordance with the instant invention will be the preparation of transformation constructs comprising the RS81 promoter operably linked to a selected coding region. By including an enhancer sequence with such constructs, the expression of the selected protein may be enhanced. These enhancers often are found 5' to the start of transcription in a promoter that functions in eukaryotic cells, but can often be inserted in the forward or reverse orientation 5' or 3' to the coding sequence. In some instances these 5' enhancing elements are introns. Deemed to be particularly useful as enhancers are the 5' introns of the rice actin 1 and rice actin 2 genes. Examples of other enhancers which could be used in accordance with the invention include elements from the CaMV 35S promoter, octopine synthase genes (Ellis et al., 1987), the maize alcohol dehydrogenase gene, the maize shrunken 1 gene and promoters from non-plant eukaryotes (e.g., yeast; Ma et al., 1988).

Where an enhancer is used in conjunction with an RS81 promoter for the expression of a selected protein, it is believed that it will be preferred to place the enhancer between the promoter and the start codon of the selected coding region. However, one also could use a different arrangement of the enhancer relative to other sequences and still realize the beneficial properties conferred by the enhancer. For example, the enhancer could be placed 5' of the promoter region, within the promoter region, within the coding sequence (including within any other intron sequences which may be present), or 3' of the coding region.

In addition to introns with enhancing activity, other types of elements can influence gene expression. For example, untranslated leader sequences have been made to predict optimum or sub-optimum sequences and generate "consensus" and preferred leader sequences (Joshi, 1987). Preferred leader sequences are contemplated to include those which have sequences predicted to direct optimum expression of the attached coding region, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants, and in maize in particular, will be most preferred.

Specifically contemplated for use in accordance with the present invention are vectors which include the ocs enhancer element. This element was first identified as a 16 bp palindromic enhancer from the octopine synthase (ocs) gene of Agrobacterium (Ellis et al., 1987), and is present in at least 10 other promoters (Bouchez et al., 1989). It is proposed that the use of an enhancer element, such as the ocs element and particularly multiple copies of the element, may be used to increase the level of transcription from adjacent promoters when applied in the context of monocot transformation.

Ultimately, the most desirable DNA segments for introduction into a plant genome may be homologous genes or gene families which encode a desired trait, and which are introduced under the control of the maize RS81 promoter. The tissue-specific expression profile of the RS81 promoter will be of particular benefit in the expression of transgenes in plants. For example, it is envisioned that a particular use of the present invention may be the production of transformants comprising a transgene which is expressed in a tissue-specific manner, whereby the expression is enhanced by an actin 1 or actin 2 intron. For example, insect resistant protein may be expressed specifically in the roots which are targets for a number of pests including nematodes and the corn root worm.

It also is contemplated that expression of one or more transgenes may be obtained in all tissues but roots by introducing a constitutively expressed gene (all tissues) in combination with an antisense gene that is expressed only by the RS81 promoter. Therefore, expression of an antisense transcript encoded by the constitutive promoter would prevent accumulation of the respective protein encoded by the sense transcript. Similarly, antisense technology could be used to achieve temporally-specific or inducible expression of a transgene encoded by an RS81 promoter.

It also is contemplated that it may be useful to target DNA within a cell. For example, it may be useful to target introduced DNA to the nucleus as this may increase the frequency of transformation. Within the nucleus itself, it would be useful to target a gene in order to achieve site specific integration. For example, it would be useful to have a gene introduced through transformation replace an existing gene in the cell.

(ii) Terminators

Transformation constructs prepared in accordance with the invention will typically include a 3' end DNA sequence that acts as a signal to terminate transcription and allow for the poly-adenylation of the mRNA produced by coding sequences operably linked to the maize RS81 promoter. Terminators which are deemed to be particularly usefull in conjunction with the RS81 promoter are those from a gene encoding the small subunit of a ribulose-1,5-bisphosphate carboxylase-oxygenase (rbcS), and more specifically, from a rice rbcS gene. An exemplary rbcS terminator for use with the maize RS81 promoter comprises the nucleic acid sequence of SEQ ID NO:2.

Where a 3' end other than an rbcS terminator is used in accordance with the invention, the most preferred 3' ends are contemplated to be those from the nopaline synthase gene of *Agrobacterium tumefaciens* (nos 3' end) (Bevan et al., 1983), the terminator for the T7 transcript from the octopine synthase gene of *Agrobacterium tumefaciens,* and the 3' end of the protease inhibitor I or II genes from potato or tomato. Regulatory elements such as Adh intron (Callis et al., 1987), sucrose synthase intron (Vasil et al., 1989) or TMV omega element (Gallie, et al., 1989), may further be included where desired. Alternatively, one also could use a gamma coixin, oleosin 3 or other terminator from the genus Coix.

(iii) Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

A particular example of such a use concerns the direction of a protein conferring herbicide resistance, such as a mutant EPSPS protein, to a particular organelle such as the chloroplast rather than to the cytoplasm. This is exemplified by the use of the rbcS transit peptide, the chloroplast transit peptide described in U.S. Pat. No. 5,728,925, or the optimized transit peptide described in U.S. Pat. No. 5,510,471, which confers plastid-specific targeting of proteins. In addition, it may be desirable to target certain genes responsible for male sterility to the mitochondria, or to target certain genes for resistance to phytopathogenic organisms to the extracellular spaces, or to target proteins to the vacuole. A further use concerns the direction of enzymes involved in amino acid biosynthesis or oil synthesis to the plastid. Such enzymes include dihydrodipicolinic acid synthase which may contribute to increasing lysine content of a feed.

(iv) Marker Genes

One application of the maize RS81 promoter of the current invention will be in the expression of marker proteins. By employing a selectable or screenable marker gene as, or in addition to, the gene of interest, one can provide or enhance the ability to identify transformants. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker genes are known to the art and can be employed in the practice of the invention.

Included within the terms selectable or screenable marker genes also are genes which encode a "secretable marker" whose secretion can be detected as a means of identifying or selecting for transformed cells. Examples include marker genes which encode a secretable antigen that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

One example of a protein suitable for modification in this manner is extensin, or hydroxyproline rich glycoprotein (HPRG). The use of maize HPRG (Steifel et al., 1990) is preferred, as this molecule is well characterized in terms of molecular biology, expression and protein structure. However, any one of a variety of extensins and/or glycine-rich wall proteins (Keller et al., 1989) could be modified by the addition of an antigenic site to create a screenable marker.

One exemplary embodiment of a secretable screenable marker concerns the use of a maize sequence encoding the wall protein HPRG, modified to include a 15 residue epitope from the pro-region of murine interleukin-1-β(IL-1-β). However, virtually any detectable epitope may be employed in such embodiments, as selected from the extremely wide variety of antigen:antibody combinations known to those of skill in the art. The unique extracellular epitope, whether derived from IL-1β or any other protein or epitopic substance, can then be straightforwardly detected using antibody labeling in conjunction with chromogenic or fluorescent adjuncts.

1. Selectable Markers

Many selectable marker coding regions may be used in connection with the RS81 promoter of the present invention including, but not limited to, neo (Potrykus et al., 1985) which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154,204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan. Where a mutant EPSP synthase is employed, additional benefit may be realized through the incorporation of a suitable chloroplast transit peptide, CTP (U.S. Pat. No. 5,188,642) or OTP (U.S. Pat. No. 5,633,448) and use of a modified maize EPSPS (PCT Application WO 97/04103).

An illustrative embodiment of selectable markers capable of being used in systems to select transformants are the enzyme phosphinothricin acetyltransferase, such as bar from *Streptomyces hygroscopicus* or pat from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death.

Where one desires to employ bialaphos resistance in the practice of the invention, the inventor has discovered that particularly useful genes for this purpose are the bar or pat genes obtainable from species of Streptomyces (e.g., ATCC No. 21,705). The cloning of the bar gene has been described (Murakami et al., 1986; Thompson et al., 1987) as has the use of the bar gene in the context of plants (De Block et al., 1987; De Block et al., 1989; U.S. Pat. No. 5,550,318).

2. Screenable Markers

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; an aequorin gene (Prasher et al., 1985) which may be employed in calcium-sensitive bioluminescence detection; or a gene encoding for green fluorescent protein (Sheen et al., 1995; Haseloff et al., 1997; Reichel et al, 1996; Tian et al., 1997; WO 97/41228).

Genes from the maize R gene complex are contemplated to be particularly useful as screenable markers. The R gene complex in maize encodes a protein that acts to regulate the production of anthocyanin pigments in most seed and plant tissue. Maize strains can have one, or as many as four, R alleles which combine to regulate pigmentation in a developmental and tissue specific manner. Thus, an R gene introduced into such cells will cause the expression of a red pigment and, if stably incorporated, can be visually scored as a red sector. If a maize line carries dominant alleles for genes encoding for the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 which contains the rg-Stadler allele and TR112, a K55 derivative which is r-g, b, P1. Alternatively, any genotype of maize can be utilized if the C1 and R alleles are introduced together.

It further is proposed that R gene regulatory regions may be employed in chimeric constructs in order to provide mechanisms for controlling the expression of chimeric genes. More diversity of phenotypic expression is known at the R locus than at any other locus (Coe et al., 1988). It is contemplated that regulatory regions obtained from regions 5' to the structural R gene would be valuable in directing the expression of genes for, e.g., insect resistance, herbicide tolerance or other protein coding regions. For the purposes of the present invention, it is believed that any of the various R gene family members may be successfully employed (e.g., P, S, Lc, etc.). However, the most preferred will generally be Sn (particularly Sn:bol3). Sn is a dominant member of the R gene complex and is functionally similar to the R and B loci in that Sn controls the tissue specific deposition of anthocyanin pigments in certain seedling and plant cells, therefore, its phenotype is similar to R.

Another screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It also is envisioned that this system may be developed for populational screening for bioluminescence, such as on tissue culture plates, or even for whole plant screening. The gene which encodes green fluorescent protein (GFP) is contemplated as a particularly useful reporter gene (Sheen et al., 1995; Haseloff et al., 1997; Reichel et al., 1996; Tian et al., 1997; WO 97/41228). Expression of green fluorescent protein may be visualized in a cell or plant as fluorescence following illumination by particular wavelengths of light. Where use of a screenable marker gene such as lux or GFP is desired, the inventors contemplated that benefit may be realized by creating a gene fusion between the screenable marker gene and a selectable marker gene, for example, a GFP-NPTII gene fusion. This could allow, for example, selection of transformed cells followed by screening of transgenic plants or seeds.

III. Exogenous Genes for Modification of Plant Phenotypes

A particularly important advance of the present invention is that it provides methods and compositions for the efficient expression of selected proteins in plant cells. In particular, the current invention provides an RS81 promoter for the expression of selected proteins in plants. By including an enhancer with transformation constructs comprising the RS81 promoter, increased expression of selected proteins can be realized following introduction of the transformation construct into a host plant cell.

The choice of a selected protein for expression in a plant host cell in accordance with the invention will depend on the purpose of the transformation. One of the major purposes of transformation of crop plants is to add commercially desirable, agronomically important traits to the plant. Such traits include, but are not limited to, herbicide resistance or tolerance; insect resistance or tolerance; disease resistance or tolerance (viral, bacterial, fungal, nematode); stress tolerance and/or resistance, as exemplified by resistance or tolerance to drought, heat, chilling, freezing, excessive moisture, salt stress and oxidative stress; increased yields; food content and makeup; physical appearance; male sterility; drydown; standability; prolificacy; starch quantity and quality; oil quantity and quality; protein quality and quantity; amino acid composition; and the like.

In certain embodiments of the invention, transformation of a recipient cell may be carried out with more than one exogenous (selected) gene. As used herein, an "exogenous coding region" or "selected coding region" is a coding region not normally found in the host genome in an identical context. By this, it is meant that the coding region may be isolated from a different species than that of the host genome, or alternatively, isolated from the host genome, but is operably linked to one or more regulatory regions which differ from those found in the unaltered, native gene. Two or more exogenous coding regions also can be supplied in a single transformation event using either distinct transgene-encoding vectors, or using a single vector incorporating two or more coding sequences. For example, plasmids bearing the bar and aroA expression units in either convergent, divergent, or colinear orientation, are considered to be particularly useful. Further preferred combinations are those of an insect resistance gene, such as a Bt gene, along with a protease inhibitor gene such as pinII, or the use of bar in combination with either of the above genes. Of course, any two or more transgenes of any description, such as those conferring herbicide, insect, disease (viral, bacterial, fungal, nematode) or drought resistance, male sterility, drydown, standability, prolificacy, starch properties, oil quantity and quality, or those increasing yield or nutritional quality may be employed as desired.

(i) Herbicide Resistance

The DNA segments encoding phosphinothricin acetyltransferase (bar and pat), EPSP synthase encoding genes conferring resistance to glyphosate, the glyphosate degradative enzyme gene gox encoding glyphosate oxidoreductase, deh (encoding a dehalogenase enzyme that inactivates dalapon), herbicide resistant (e.g., sulfonylurea and imidazolinone) acetolactate synthase, and bxn genes (encoding a nitrilase enzyme that degrades bromoxynil) are examples of herbicide resistant genes for use in transformation. The bar and pat genes code for an enzyme, phosphinothricin acetyltransferase (PAT), which inactivates the herbicide phosphinothricin and prevents this compound from inhibiting glutamine synthetase enzymes. The enzyme 5-enolpyruvylshikimate 3-phosphate synthase (EPSP Synthase), is normally inhibited by the herbicide N-(phosphonomethyl)glycine (glyphosate). However, genes are known that encode glyphosate-resistant EPSP synthase enzymes. These genes are particularly contemplated for use in plant transformation. The deh gene encodes the enzyme dalapon dehalogenase and confers resistance to the herbicide dalapon. The bxn gene codes for a specific nitrilase enzyme that converts bromoxynil to a non-herbicidal degradation product.

(ii) Insect Resistance

Potential insect resistance genes that can be introduced include *Bacillus thuringiensis* crystal toxin genes or Bt genes (Watrud et al., 1985). Bt genes may provide resistance to lepidopteran or coleopteran pests such as European Corn Borer (ECB). Preferred Bt or other types of insect resistance genes for use with the current invention will have activity against pests capable of infesting the root systems of crop plants, for example, the northern corn rootworm (*Diabrotica barberi*), southern corn rootworm (*Diabrotica undecimpunctata*), Western corn rootworm (*Diabrotica virgifera*), black cutworm (*Agrotis ipsilon*), glassy cutworm (*Crymodes devastator*), dingy cutworm (*Feltia ducens*), claybacked cutworm (*Agrotis gladiaria*), wireworm (Melanotus spp., *Aeolus mellillus*), wheat wireworm (*Aeolus mancus*), sand wireworm (*Horistonotus uhlerii*), maize billbug (*Sphenophorus maidis*), timothy billbug (*Sphenophorus zeae*), bluegrass billbug (*Sphenophorus parvulus*), southern corn billbug (*Sphenophorus callosus*), white grubs (Phyllogphaga spp.), corn root aphid (*Anuraphis maidiradicis*), seedcorn maggot (*Delia platura*), grape colaspis (*Colaspis brunnea*), seedcorn beetle (*Stenolophus lecontei*), and slender seedcorn beetle (*Clivinia impressifrons*).

It is contemplated that preferred Bt genes for use in the transformation protocols disclosed herein will be those in which the coding sequence has been modified to effect increased expression in plants, and more particularly, in maize. Means for preparing synthetic genes are well known in the art and are disclosed in, for example, U.S. Pat. No. 5,500,365 and U.S. Pat. Number No. 5,689,052, each of the disclosures of which are specifically incorporated herein by reference in their entirety. Examples of such modified Bt toxin genes include a synthetic Bt CryIA(b) gene (Perlak et al., 1991), and the synthetic CryIA(c) gene termed 1800b (PCT Application WO 95/06128). Some examples of other Bt toxin genes known to those of skill in the art are given in Table 1 below.

TABLE 1

*Bacillus thuringiensis* δ-Endotoxin Genes[a]

| New Nomenclature | Old Nomenclature | GenBank Accession |
| --- | --- | --- |
| Cry1Aa | CryIA(a) | M11250 |
| Cry1Ab | CryIA(b) | M13898 |
| Cry1Ac | CryIA(c) | M11068 |
| Cry1Ad | CryIA(d) | M73250 |
| Cry1Ae | CryIA(e) | M65252 |
| Cry1Ba | CryIB | X06711 |
| Cry1Bb | ET5 | L32020 |
| Cry1Bc | PEG5 | Z46442 |
| Cry1Bd | CryE1 | U70726 |
| Cry1Ca | CryIC | X07518 |
| Cry1Cb | CryIC(b) | M97880 |
| Cry1Da | CryID | X54160 |
| Cry1Db | PrtB | Z22511 |
| Cry1Ea | CryIE | X53985 |
| Cry1Eb | CryIE(b) | M73253 |
| Cry1Fa | CryIF | M63897 |
| Cry1Fb | PrtD | Z22512 |
| Cry1Ga | PrtA | Z22510 |
| Cry1Gb | CryH2 | U70725 |
| Cry1Na | PrtC | Z22513 |
| Cry1Hb |  | U35780 |
| Cry1Ia | CryV | X62821 |
| Cry1Ib | CryV | U07642 |
| Cry1Ja | ET4 | L32019 |
| Cry1Jb | ET1 | U31527 |
| Cry1K |  | U28801 |
| Cry2Aa | CryIIA | M31738 |
| Cry2Ab | CryIIB | M23724 |
| Cry2Ac | CryIIC | X57252 |
| Cry3A | CryIIIA | M22472 |
| Cry3Ba | CryIIIB | X17123 |
| Cry3Bb | CryIIIB2 | M89794 |
| Cry3C | CryIIID | X59797 |
| Cry4A | CryIVA | Y00423 |
| Cry4B | CryIVB | X07423 |
| Cry5Aa | CryVA(a) | L07025 |
| Cry5Ab | CryVA(b) | L07026 |
| Cry6A | CryVIA | L07022 |
| Cry6B | CryVIB | L07024 |
| Cry7Aa | CryIIIC | M64478 |
| Cry7Ab | CryIIICb | U04367 |
| Cry8A | CryIIIE | U04364 |
| Cry8B | CryIIIG | U04365 |
| Cry8C | CryIIIF | U04366 |
| Cry9A | CryIG | X58120 |
| Cry9B | CryIX | X75019 |
| Cry9C | CryIH | Z37527 |
| Cry10A | CryIVC | M12662 |
| Cry11A | CryIVD | M31737 |
| Cry11B | Jeg80 | X86902 |
| Cry12A | CryVB | L07027 |

TABLE 1-continued

Bacillus thuringiensis δ-Endotoxin Genes[a]

| New Nomenclature | Old Nomenclature | GenBank Accession |
|---|---|---|
| Cry13A | CryVC | L07023 |
| Cry14A | CryVD | U13955 |
| Cry15A | 34kDa | M76442 |
| Cry16A | cbm71 | X94146 |
| Cry17A | cbm71 | X99478 |
| Cry18A | CryBP1 | X99049 |
| Cry19A | Jeg65 | Y08920 |
| Cyt1Aa | CytA | X03182 |
| Cyt1Ab | CytM | X98793 |
| Cyt2A | CytB | Z14147 |
| Cyt2B | CytB | U52043 |

[a]Adapted from: http://epunix.biols.susx.ac.uk/Home/Neil_Crickmore/Bt/index.html Protease inhibitors also may provide insect resistance (Johnson et al., 1989), and thus will have utility in plant transformation. The use of a protease inhibitor II gene, pinII, from tomato or potato is envisioned to be particularly useful. Even more advantageous is the use of a pinII gene in combination with a Bt toxin gene, the combined effect of which has been discovered to produce synergistic insecticidal activity. Other genes which encode inhibitors of the insect's digestive system, or those that encode enzymes or co-factors that facilitate the production of inhibitors, also may be useful. This group may be exemplified by oryzacystatin and amylase inhibitors such as those from wheat and barley.

Also, genes encoding lectins may confer additional or alternative insecticide properties. Lectins (originally termed phytohemagglutinins) are multivalent carbohydrate-binding proteins which have the ability to agglutinate red blood cells from a range of species. Lectins have been identified recently as insecticidal agents with activity against weevils, ECB and rootworm (Murdock et al., 1990; Czapla & Lang, 1990). Lectin genes contemplated to be useful include, for example, barley and wheat germ agglutinin (WGA) and rice lectins (Gatehouse et al., 1984), with WGA being preferred.

Genes controlling the production of large or small polypeptides active against insects when introduced into the insect pests, such as, e.g., lytic peptides, peptide hormones and toxins and venoms, form another aspect of the invention. For example, it is contemplated that the expression of juvenile hormone esterase, directed towards specific insect pests, also may result in insecticidal activity, or perhaps cause cessation of metamorphosis (Hammock et al., 1990).

Transgenic plants expressing genes which encode enzymes that affect the integrity of the insect cuticle form yet another aspect of the invention. Such genes include those encoding, e.g., chitinase, proteases, lipases and also genes for the production of nikkomycin, a compound that inhibits chitin synthesis, the introduction of any of which is contemplated to produce insect resistant plants. Genes that code for activities that affect insect molting, such as those affecting the production of ecdysteroid UDP-glucosyl transferase, also fall within the scope of the useful transgenes of the present invention.

Genes that code for enzymes that facilitate the production of compounds that reduce the nutritional quality of the host plant to insect pests also are encompassed by the present invention. It may be possible, for instance, to confer insecticidal activity on a plant by altering its sterol composition. Sterols are obtained by insects from their diet and are used for hormone synthesis and membrane stability. Therefore, alterations in plant sterol composition by expression of novel genes, e.g., those that directly promote the production of undesirable sterols or those that convert desirable sterols into undesirable forms, could have a negative effect on insect growth and/or development and hence endow the plant with insecticidal activity. Lipoxygenases are naturally occurring plant enzymes that have been shown to exhibit anti-nutritional effects on insects and to reduce the nutritional quality of their diet. Therefore, further embodiments of the invention concern transgenic plants with enhanced lipoxygenase activity which may be resistant to insect feeding.

*Tripsacum dactyloides* is a species of grass that is resistant to certain insects, including corn root worm. It is anticipated that genes encoding proteins that are toxic to insects or are involved in the biosynthesis of compounds toxic to insects will be isolated from Tripsacum and that these novel genes will be useful in conferring resistance to insects. It is known that the basis of insect resistance in Tripsacum is genetic, because said resistance has been transferred to *Zea mays* via sexual crosses (Branson and Guss, 1972). It further is anticipated that other cereal, monocot or dicot plant species may have genes encoding proteins that are toxic to insects which would be useful for producing insect resistant corn plants.

Further genes encoding proteins characterized as having potential insecticidal activity also may be used as transgenes in accordance herewith. Such genes include, for example, the cowpea trypsin inhibitor (CpTI; Hilder et al., 1987) which may be used as a rootworm deterrent; genes encoding avermectin (Avermectin and Abamectin., Campbell, W. C., Ed., 1989; Ikeda et al., 1987) which may prove particularly useful as a corn rootworm deterrent; ribosome inactivating protein genes; and even genes that regulate plant structures. Transgenic maize including anti-insect antibody genes and genes that code for enzymes that can convert a non-toxic insecticide (pro-insecticide) applied to the outside of the plant into an insecticide inside the plant also are contemplated.

(iii) Environment or Stress Resistance

Improvement of a plants ability to tolerate various environmental stresses such as, but not limited to, drought, excess moisture, chilling, freezing, high temperature, salt, and oxidative stress, also can be effected through expression of novel genes. It is proposed that benefits may be realized in terms of increased resistance to freezing temperatures through the introduction of an "antifreeze" protein such as that of the Winter Flounder (Cutler et al, 1989) or synthetic gene derivatives thereof. Improved chilling tolerance also may be conferred through increased expression of glycerol-3-phosphate acetyltransferase in chloroplasts (Wolter et al., 1992). Resistance to oxidative stress (often exacerbated by conditions such as chilling temperatures in combination with high light intensities) can be conferred by expression of superoxide dismutase (Gupta et al., 1993), and may be improved by glutathione reductase (Bowler et al., 1992). Such strategies may allow for tolerance to freezing in newly emerged fields as well as extending later maturity higher yielding varieties to earlier relative maturity zones.

It is contemplated that the expression of novel genes that favorably effect plant water content, total water potential, osmotic potential, and turgor will enhance the ability of the plant to tolerate drought. As used herein, the terms "drought resistance" and "drought tolerance" are used to refer to a plants increased resistance or tolerance to stress induced by a reduction in water availability, as compared to normal circumstances, and the ability of the plant to function and survive in lower-water environments. In this aspect of the invention it is proposed, for example, that the expression of genes encoding for the biosynthesis of osmotically-active solutes, such as polyol compounds, may impart protection against drought. Within this class are genes encoding for mannitol-L-phosphate dehydrogenase (Lee and Saier, 1982) and trehalose-6-phosphate synthase (Kaasen et al., 1992). Through the subsequent action of native phosphatases in the cell or by the introduction and coexpression of a specific phosphatase, these introduced genes will result in the accumulation of either mannitol or trehalose, respectively, both of which have been well documented as protective compounds able to mitigate the effects of stress. Mannitol accumulation in transgenic tobacco has been verified and preliminary results indicate that plants expressing high levels of this metabolite are able to tolerate an applied osmotic stress (Tarczynski et al., 1992, 1993). Altered water utilization in transgenic corn producing mannitol also has been demonstrated (U.S. Pat. No. 5,780,709).

Similarly, the efficacy of other metabolites in protecting either enzyme function (e.g., alanopine or propionic acid) or membrane integrity (e.g., alanopine) has been documented (Loomis et al., 1989), and therefore expression of genes encoding for the biosynthesis of these compounds might confer drought resistance in a manner similar to or complimentary to mannitol. Other examples of naturally occurring metabolites that are osmotically active and/or provide some direct protective effect during drought and/or desiccation include fructose, erythritol (Coxson et al., 1992), sorbitol, dulcitol (Karsten et al., 1992), glucosylglycerol (Reed et al., 1984; Erdmann et al., 1992), sucrose, stachyose (Koster and Leopold, 1988; Blackman et al., 1992), raffinose (Bernal-Lugo and Leopold, 1992), proline (Rensburg et al., 1993), glycine betaine, ononitol and pinitol (Vernon and Bohnert, 1992). Continued canopy growth and increased reproductive fitness during times of stress will be augmented by introduction and expression of genes such as those controlling the osmotically active compounds discussed above and other such compounds. Currently preferred genes which promote the synthesis of an osmotically active polyol compound are genes which encode the enzymes mannitol-1-phosphate dehydrogenase, trehalose-6-phosphate synthase and myo-inositol 0-methyltransferase.

It is contemplated that the expression of specific proteins also may increase drought tolerance. Three classes of Late Embryogenic Proteins have been assigned based on structural similarities (see Dure et al., 1989). All three classes of LEAs have been demonstrated in maturing (ie., desiccating) seeds. Within these 3 types of LEA proteins, the Type-II (dehydrin-type) have generally been implicated in drought and/or desiccation tolerance in vegetative plant parts (i.e., Mundy and Chua, 1988; Piatkowski et al., 1990; Yamaguchi-Shinozaki et al., 1992). Recently, expression of a Type-III LEA (HVA-1) in tobacco was found to influence plant height, maturity and drought tolerance (Fitzpatrick, 1993). In rice, expression of the HVA-1 gene influenced tolerance to water deficit and salinity (Xu et al., 1996). Expression of structural genes from all three LEA groups may therefore confer drought tolerance. Other types of proteins induced during water stress include thiol proteases, aldolases and transmembrane transporters (Guerrero et al., 1990), which may confer various protective and/or repair-type functions during drought stress. It also is contemplated that genes that effect lipid biosynthesis and hence membrane composition might also be useful in conferring drought resistance on the plant.

Many of these genes for improving drought resistance have complementary modes of action. Thus, it is envisaged that combinations of these genes might have additive and/or synergistic effects in improving drought resistance in crop plants such as, for example, corn. Many of these genes also improve freezing tolerance (or resistance); the physical stresses incurred during freezing and drought are similar in nature and may be mitigated in similar fashion. Benefit may be conferred via constitutive expression of these genes, but the preferred means of expressing these novel genes may be through the use of a turgor-induced promoter (such as the promoters for the turgor-induced genes described in Guerrero et al., 1990 and Shagan et al., 1993 which are incorporated herein by reference). Spatial and temporal expression patterns of these genes may enable plants to better withstand stress.

It is proposed that expression of genes that are involved with specific morphological traits that allow for increased water extractions from drying soil would be of benefit. For example, introduction and expression of genes that alter root characteristics may enhance water uptake. It also is contemplated that expression of genes that enhance reproductive fitness during times of stress would be of significant value. For example, expression of genes that improve the synchrony of pollen shed and receptiveness of the female flower parts, i.e., silks, would be of benefit. In addition it is proposed that expression of genes that minimize kernel abortion during times of stress would increase the amount of grain to be harvested and hence be of value.

Given the overall role of water in determining yield, it is contemplated that enabling corn and other crop plants to utilize water more efficiently, through the introduction and expression of novel genes, will improve overall performance even when soil water availability is not limiting. By introducing genes that improve the ability of plants to maximize water usage across a full range of stresses relating to water availability, yield stability or consistency of yield performance may be realized.

(iv) Disease Resistance

It is proposed that increased resistance to diseases may be realized through introduction of genes into plants, for example, into monocotyledonous plants such as maize. It is possible to produce resistance to diseases caused by viruses, bacteria, fungi and nematodes. It also is contemplated that control of mycotoxin producing organisms may be realized through expression of introduced genes.

Resistance to viruses may be produced through expression of novel genes. For example, it has been demonstrated that expression of a viral coat protein in a transgenic plant can impart resistance to infection of the plant by that virus and perhaps other closely related viruses (Cuozzo et al., 1988, Hemenway et al., 1988, Abel et al., 1986). It is contemplated that expression of antisense genes targeted at essential viral functions also may impart resistance to viruses. For example, an antisense gene targeted at the gene responsible for replication of viral nucleic acid may inhibit replication and lead to resistance to the virus. It is believed that interference with other viral functions through the use of antisense genes also may increase resistance to viruses. Similarly, ribozymes could be used in this context. Further, it is proposed that it may be possible to achieve resistance to viruses through other approaches, including, but not limited to the use of satellite viruses. Examples of viral and viral-like diseases, for which one could introduce resistance to in a transgenic plant in accordance with the instant invention, are listed below, in Table 2.

TABLE 2

Plant Virus and Virus-like Diseases

| DISEASE | CAUSATIVE AGENT |
|---|---|
| American wheat striate (wheat striate mosaic) | American wheat striate mosaic virus mosaic (AWSMV) |
| Barley stripe mosaic | Barley stripe mosaic virus (BSMV) |
| Barley yellow dwarf | Barley yellow dwarf virus (BYDV) |
| Brome mosaic | Brome mosaic virus (BMV) |
| Cereal chlorotic mottle* | Cereal chlorotic mottle virus (CCMV) |
| Corn chlorotic vein banding (Braizilian maize mosaic)[1] mosaic) | Corn chlorotic vein banding virus (CCVBV) |
| Corn lethal necrosis | Virus complex (Maize chlorotic mottle virus(MCMV) and Maize dwarf mosaic virus (MDMV) A or B or Wheat streak mosaic virus(WSMV)) |
| Cucumber mosaic | Cucumber mosaic virus (CMV) |
| Cynodon chlorotic streak*,[1] | Cynodon chlorotic streak virus (CCSV) |
| Johnsongrass mosaic | Johnsongrass mosaic virus (JGMV) |
| Maize bushy stunt | Mycoplasma-like organism (MLO) associated |
| Maize chlorotic dwarf | Maize chlorotic dwarf virus (MCDV) |
| Maize chlorotic mottle | Maize chlorotic mottle virus (MCMV) |
| Maize dwarf mosaic | Maize dwarf mosaic virus (MDMV) strains A, D, E and F |
| Maize leaf fleck | Maize leaf fleck virus (MLFV) |
| Maize line* | Maize line virus (MLV) |
| Maize mosaic (corn leaf stripe, enanismo rayado) | Maize mosaic virus (MMV) |
| Maize mottle and chlorotic stunt[1] | Maize mottle and chlorotic stunt virus* |
| Maize pellucid ringspot* | Maize pellucid ringspot virus (MPRV) |
| Maize raya gruesa*,[1] | Maize raya gruesa virus (MRGV) |
| maize rayado fino* (fine striping disease) | Maize rayado fino virus (MRFV) |
| Maize red leaf and red stripe* | Mollicute |
| Maize red stripe* | Maize red stripe virus (MRSV) |
| Maize ring mottle* | Maize ring mottle virus (MRMV) |
| Maize rio IV* | Maize rio cuarto virus (MRCV) |
| Maize rough dwarf* (nanismo ruvido) | Maize rough dwarf virus (MRDV) (= Cereal tillering disease virus*) |
| Maize sterile stunt* | Maize sterile stunt virus (strains of barley yellow striate virus) |
| Maize streak* | Maize streak virus (MSV) |
| Maize stripe (maize chlorotic stripe, maize hoja blanca) | Maize stripe virus |
| Maize stunting*,[1] | Maize stunting virus |
| Maize tassel abortion* | Maize tassel abortion virus (MTAV) |
| Maize vein enation* | Maize vein enation virus (MVEV) |
| Maize wallaby ear* | Maize wallaby ear virus (MWEV) |
| Maize white leaf* | Maize white leaf virus |
| Maize white line mosaic | Maize white line mosaic virus (MWLMV) |
| Millet red leaf* | Millet red leaf virus (MRLV) |
| Northern cereal mosaic* | Northern cereal mosaic virus (NCMV) |
| Oat pseudorosette* (zakuklivanie) | Oat pseudorosette virus |
| Oat sterile dwarf* | Oat sterile dwarf virus (OSDV) |
| Rice black-streaked dwarf* | Rice black-streaked dwarf virus (RBSDV) |
| Rice stripe* | Rice stripe virus (RSV) |
| Sorghum mosaic | Sorghum mosaic virus (SrMV), formerly sugarcane mosaic virus (SCMV) strains H, I and M |
| Sugarcane Fiji disease* | Sugarcane Fiji disease virus (FDV) |
| Sugarcane mosaic | Sugarcane mosaic virus (SCMV) strains A, B, D, E, SC, BC, Sabi and MB (formerly MDMV-B) |
| Vein enation*,[1] | Virus |
| Wheat spot mosaic[1] | Wheat spot mosaic virus (WSMV) |

*Not known to occur naturally on corn in the United States.
[1]Minor viral disease.

It is proposed that increased resistance to diseases caused by bacteria and fungi also may be realized through introduction of novel genes. It is contemplated that genes encoding so-called "peptide antibiotics," pathogenesis related (PR) proteins, toxin resistance, and proteins affecting host-pathogen interactions such as morphological characteristics will be useful. Peptide antibiotics are polypeptide sequences which are inhibitory to growth of bacteria and other microorganisms. For example, the classes of peptides referred to as cecropins and magainins inhibit growth of many species of bacteria and fungi. It is proposed that expression of PR proteins in monocotyledonous plants such as maize may be useful in conferring resistance to bacterial disease. These genes are induced following pathogen attack on a host plant and have been divided into at least five classes of proteins (Bol, Linthorst, and Cornelissen, 1990). Included amongst the PR proteins are $\beta$-1, 3-glucanases, chitinases, and osmotin and other proteins that are believed to function in plant resistance to disease organisms. Other genes have been identified that have antifungal properties, e.g., UDA (stinging nettle lectin) and hevein (Broakaert et al., 1989; Barkai-Golan et al., 1978). It is known that certain plant diseases are caused by the production of phytotoxins. It is proposed that resistance to these diseases would be achieved through expression of a novel gene that encodes an enzyme capable of degrading or otherwise inactivating the phytotoxin. It also is contemplated that expression of novel genes that alter the interactions between the host plant and pathogen may be useful in reducing the ability of the disease organism to invade the tissues of the host plant, e.g., an increase in the waxiness of the leaf cuticle or other morphological characteristics. Examples of bacterial and fungal diseases, including downy mildews, for which one could introduce resistance to in a transgenic plant in accordance with the instant invention, are listed below, in Tables 3, 4 and 5.

TABLE 3

Plant Bacterial Diseases

| DISEASE | CAUSATIVE AGENT |
|---|---|
| Bacterial leaf blight and stalk rot | Pseudomonas avenae subsp. avenae |
| Bacterial leaf spot | Xanthomonas campestris pv. holcicola |
| Bacterial stalk rot | Enterobacter dissolvens = Erwinia dissolvens |
| Bacterial stalk and top rot | Erwinia carotovora subsp. carotovora, Erwinia chrysanthemi pv. zeae |
| Bacterial stripe | Pseudomonas andropogonis |
| Chocolate spot | Pseudomonas syringae pv. coronafaciens |
| Goss's bacterial wilt and blight (leaf freckles and wilt) | Clavibacter michiganensis subsp. nebraskensis = Corynebacterium michiganense pv. nebraskense |
| Holcus spot | Pseudomonas syringae pv. syringae |
| Purple leaf sheath | Hemiparasitic bacteria + (See under Fungi) |
| Seed rot-seedling blight | Bacillus subtilis |
| Stewart's disease (bacterial wilt) | Pantoea stewartii = Erwinia stewartii |
| Corn stunt (achapparramiento, maize stunt, Mesa Central or Rio Grande maize stunt) | Spiroplasma kunkelii |

TABLE 4

Plant Fungal Diseases

| DISEASE | PATHOGEN |
|---|---|
| Anthrocnose leaf blight and anthracnose stalk rot | Colletotrichum graminicola (teleomorph: Glomerella graminicola Politis), Glomerella tucumanensis (anamorph: Glomerella falcatum |

TABLE 4-continued

Plant Fungal Diseases

| DISEASE | PATHOGEN |
|---|---|
| Aspergillus ear and kernel rot | Aspergillus flavus Link: Fr. Went) |
| Banded leaf and sheath spot* | Rhizoctonia solani Kühn = Rhizoctonia microsclerotia J. Matz (telomorph: Thanatephorus cucumeris) |
| Black bundle disease | Acremonium strictum W. Gams = Cephalosporium acremonium Auct. non Corda |
| Black kernel rot* | Lasiodiplodia theobromae = Botryodiplodia theobromae |
| Borde blanco* | Marasmiellus sp. |
| Brown spot (black spot, stalk rot) | Physoderma maydis |
| Cephalosporium kernel rot | Acremonium strictum = Cephalosporium acremonium |
| Charcoal rot | Macrophomina phaseolina |
| Corticium ear rot* | Thanatephorus cucumeris = Corticium sasakii |
| Curvularia leaf spot | Curvularia clavata, C. eragrostidis, = C. maculans (teleomorph: Cochliobolus eragrostidis), Curvularia inaequalis, C. intermedia (teleomorph: Cochliobolus intermedius), Curvularia lunata (teleomorph: Cochliobolus lunatus), Curvularia pallescens (teleomorph: Cochliobolus pallescens), Curvularia senegalensis, C. tuberculata (teleomoph: Cochliobolus tuberculatus) |
| Didymella leaf spot* | Didymella exitalis |
| Diplodia ear rot and stalk rot | Diplodia frumenti (teleomorph: Botryosphaeria festucae) |
| Diplodia ear rot, stalk rot, seed rot and seedling blight | Diplodia maydis = Stenocarpella maydis |
| Diplodia leaf spot or leaf streak | Stenocarpella macrospora = Diplodia macrospora |

*Not known to occur naturally on corn in the United States.

TABLE 5

Plant Downy Mildews

| DISEASE | CAUSATIVE AGENT |
|---|---|
| Brown stripe downy mildew* | Sclerophthora rayssiae var. zeae |
| Crazy top downy mildew | Sclerophthora macrospora = Sclerospora macrospora |
| Green ear downy mildew (graminicola downy mildew) | Sclerospora graminicola |
| Java downy mildew* | Peronosclerospora maydis = Sclerospora maydis |
| Philippine downy mildew* | Peronosclerospora philippinensis = Sclerospora philippinensis |
| Sorghum downy mildew | Peronosclerospora sorghi = Sclerospora sorghi |
| Spontaneum downy mildew* | Peronosclerospora spontanea = Sclerospora spontanea |
| Sugarcane downy mildew* | Peronosclerospora sacchari = Sclerospora sacchari |
| Dry ear rot (cob, kernel and stalk rot) | Nigrospora oryzae (teleomorph: Khuskia oryzae) |
| Ear rots, minor | Alternaria alternata = A. tenuis, Aspergillus glaucus, A. niger, Aspergillus spp., Botrytis cinerea (teleomorph: Botryotinia fuckeliana), Cunninghamella sp., Curvularia pallescens, Doratomyces stemonitis = Cephalotrichum stemonitis, Fusarium culmorum, Gonatobotrys simplex, Pithomyces maydicus, Rhizopus microsporus Tiegh., R. stolonifer = R. nigricans, Scopulariopsis brumptii. |
| Ergot* (horse's tooth, diente de caballo) | Claviceps gigantea (anamorph: Sphacelia sp.) |

TABLE 5-continued

Plant Downy Mildews

| DISEASE | CAUSATIVE AGENT |
|---|---|
| Eyespot | Aureobasidium zeae = Kabatiella zeae |
| Fusarium ear and stalk rot | Fusarium subglutinans = F. moniliforme var. subglutinans |
| Fusarium kernel, root and stalk rot, seed rot and seedling blight | Fusarium moniliforme (teleomorph: Gibberella fujikuroi) |
| Fusarium stalk rot, seedling root rot | Fusarium avenaceum (teleomorph: Gibberlla avenacea) |
| Gibberella ear and stalk rot | Gibberella zeae (anamorph: Fusarium graminearum) |
| Gray ear rot | Botryosphaeria zeae = Physalospora zeae (anamorph: Macrophoma zeae) |
| Gray leaf spot (Cercospora leaf spot) | Cercospora sorghi = C. sorghi var. maydis, C. zeae-maydis |
| Helminthosporium root rot | Exserohilum pedicellatum = Helminthosporium pedicellatum (teleomorph: Setosphaeria pedicellata) |
| Hormodendrum ear rot (Cladosporium rot) | Cladosporium cladosporioides = Hormodendrum cladosporioides, C. herbarum (teleomorph: Mycosphaerella tassiana) |
| Hyalothyridium leaf spot* | Hyalothyridium maydis |
| Late wilt* | Cephalosporium maydis |
| Leaf spots, minor | Alternaria alternata, Ascochyta maydis, A. tritici, A. zeicola, Bipolaris victoriae = Helminthosporium victoriae (teleomorph: Cochliobolus victoriae), C. sativus (anamorph: Bipolaris sorokiniana = H. sorokinianum = H. sativum), Epicoccum nigrum, Exserohilum prolatum = Drechslera prolata (teleomorph: Setosphaeria prolata) Graphium penicillioides, Leptosphaeria maydis, Leptothyrium zeae, Ophiosphaerella herpotricha, (anamorph: Scolecosporiella sp.), Paraphaeosphaeria michotii, Phoma sp., Septoria zeae, S. zeicola, S. zeina |
| Northern corn leaf blight (white blast, crown stalk rot, stripe) | Setosphaeria turcica (anarnorph: Exserohilum turcicum = Helminthosporium turcicum) |
| Northern corn leaf spot Helminthosporium ear rot (race 1) | Cochliobolus carbonum (anamorph: Bipolaris zeicola = Helminthosporium carbonum) |
| Penicillium ear rot (blue eye, blue mold) | Penicillium spp., P. chrysogenum, P. expansum, P. oxalicum |
| Phaeocytostroma stalk rot and root rot | Phaeocytostroma ambiguum, = Phaeocytosporella zeae |
| Phaeosphaeria leaf spot* | Phaeosphaeria maydis = Sphaerulina maydis |
| Physalospora ear rot (Botryosphaeria ear rot) | Botryosphaeria festucae = Physalospora zeicola (anamorph: Diplodia frumenti) |
| Purple leaf sheath | Hemiparasitic bacteria and fungi |
| Pyrenochaeta stalk rot and root rot | Phoma terrestris = Pyrenochaeta terrestris |
| Pythium root rot | Pythium spp., P. arrhenomanes, P. graminicola |
| Pythium stalk rot | Pythium aphanidermatum = P. butleri L. |
| Red kernel disease (ear mold, leaf and seed rot) | Epicoccum nigrum |
| Rhizoctonia ear rot (sclerotial rot) | Rhizoctonia zeae (teleomorph: Waitea circinata) |
| Rhizoctonia root rot and stalk rot | Rhizoctonia solani, Rhizoctonia zeae |
| Root rots, minor | Alternaria alternata, Cercospora sorghi, Dictochaeta fertilis, Fusarium acuminatum (teleomorph: Gibberella acuminata), F. equiseti (teleomorph: G. intricans), F. oxysporum, F. pallidoroseum, F. poae, F. roseum, G. cyanogena, (anamorph: F. sulphureum), Microdochium bolleyi, Mucor sp., Periconia circinata, Phytophthora cactorum, P. drechsleri, P. nicotianae var. parasitica, Rhizopus arrhizus |
| Rostratum leaf spot (Helminthosporium leaf disease, ear and stalk rot) | Setosphaeria rostrata, (anamorph: Exserohilum rostratum = He/minthosporium rostratum) |
| Rust, common corn | Puccinia sorghi |

TABLE 5-continued

Plant Downy Mildews

| DISEASE | CAUSATIVE AGENT |
| --- | --- |
| Rust, southern corn | *Puccinia polysora* |
| Rust, tropical corn | *Physopella pallescens, P. zeae = Angiopsora zeae* |
| Sclerotium ear rot* (southern blight) | *Sclerotium rolfsii* Sacc. (teleomorph: *Athelia rolfsii*) |
| Seed rot-seedling blight | *Bipolaris sorokiniana, B. zeicola = Helminthosporium carbonum, Diplodia maydis, Exserohilum pedicillatum, Exserohilum turcicum = Helminthosporium turcicum, Fusarium avenaceum, F. culmorum, F. moniliforme, Gibberella zeae* (anamorph: *F. graminearum*), *Macrophomina phaseolina, Penicillium* spp., *Phomopsis* sp., *Pythium* spp., *Rhizoctonia solani, R. zeae, Sclerotium rolfsii, Spicaria* sp. |
| Selenophoma leaf spot* | *Selenophoma* sp. |
| Sheath rot | *Gaeumannomyces graminis* |
| Shuck rot | *Myrothecium gramineum* |
| Silage mold | *Monascus purpureus, M ruber* |
| Smut, common | *Ustilago zeae = U. maydis*) |
| Smut, false | *Ustilaginoidea virens* |
| Smut, head | *Sphacelotheca reiliana = Sporisorium holcisorghi* |
| Southern corn leaf blight and stalk rot | *Cochliobolus heterostrophus* (anamorph: *Bipolaris maydis = Helminthosporium maydis*) |
| Southern leaf spot | *Stenocarpella macrospora = Diplodia macrospora* |
| Stalk rots, minor | *Cercospora sorghi, Fusarium episphaeria, F. merismoides, F. oxysporum* Schlechtend, *F. poae, F. roseum, F. solani* (teleomorph: *Nectria haematococca*), *F. tricinctum, Mariannaea elegans,* Mucor sp., *Rhopographus zeae, Spicaria* sp. |
| Storage rots | *Aspergillus* spp., *Penicillium* spp. and other fungi |
| Tar spot* | *Phyllachora maydis* |
| Trichoderma ear rot and root rot | *Trichoderma viride = T. lignorum* teleomorph: *Hypocrea* sp. |
| White ear rot, root and stalk rot | *Stenocarpella maydis = Diplodia zeae* |
| Yellow leaf blight | *Ascochyta ischaemi, Phyllosticta maydis* (teleomorph: *Mycosphaerella zeae-maydis*) |
| Zonate leaf spot | *Gloeocercospora sorghi* |

*Not known to occur naturally on corn in the United States.

Plant parasitic nematodes are a cause of disease in many plants, including maize. It is proposed that it would be possible to make plants resistant to these organisms through the expression of novel gene products. It is anticipated that control of nematode infestations would be accomplished by altering the ability of the nematode to recognize or attach to a host plant and/or enabling the plant to produce nematicidal compounds, including but not limited to proteins. Examples of nematode-associated plant diseases, for which one could introduce resistance to in a transgenic plant in accordance with the invention are given below, in Table 6.

TABLE 6

Parasitic Nematodes

| DISEASE | PATHOGEN |
| --- | --- |
| Awl | *Dolichodorus* spp., *D. heterocephalus* |
| Bulb and stem (Europe) | *Ditylenchus dipsaci* |
| Burrowing | *Radopholus similis* |
| Cyst | *Heterodera avenae, H. zeae, Punctodera chalcoensis* |
| Dagger | *Xiphinema* spp., *X. americanum, X. mediterraneum* |
| False root-knot | *Nacobbus dorsalis* |
| Lance, Columbia | *Hoplolaimus columbus* |
| Lance | *Hoplolaimus* spp., *H. galeatus* |
| Lesion | *Pratylenchus* spp., *P. brachyurus, P. crenatus, P. hexincisus, P. neglectus, P. penetrans, P. scribneri, P. thornei, P. zeae* |
| Needle | *Longidorus* spp., *L. breviannulatus* |
| Ring | *Criconemella* spp., *C. ornata* |
| Root-knot | *Meloidogyne* spp., *M. chitwoodi, M. incognita, M. javanica* |
| Spiral | *Helicotylenchus* spp. |
| Sting | *Belonolaimus* spp., *B. longicaudatus* |
| Stubby-root | *Paratrichodorus* spp., *P. christiei, P. minor, Quinisulcius acutus, Trichodorus* spp. |
| Stunt | *Tylenchorhynchus dubius* |

(v) Mycotoxin Reduction/Elimination

Production of mycotoxins, including aflatoxin and fumonisin, by fungi associated with monocotyledonous plants such as maize is a significant factor in rendering the grain not useful. These fungal organisms do not cause disease symptoms and/or interfere with the growth of the plant, but they produce chemicals (mycotoxins) that are toxic to animals. It is contemplated that inhibition of the growth of these fungi would reduce the synthesis of these toxic substances and therefore reduce grain losses due to mycotoxin contamination. It also is proposed that it may be possible to introduce novel genes into monocotyledonous plants such as maize that would inhibit synthesis of the mycotoxin. Further, it is contemplated that expression of a novel gene which encodes an enzyme capable of rendering the mycotoxin nontoxic would be useful in order to achieve reduced mycotoxin contamination of grain. The result of any of the above mechanisms would be a reduced presence of mycotoxins on grain.

(vi) Grain Composition or Quality

Genes may be introduced into monocotyledonous plants, particularly commercially important cereals such as maize, to improve the grain for which the cereal is primarily grown. A wide range of novel transgenic plants produced in this manner may be envisioned depending on the particular end use of the grain.

The largest use of maize grain is for feed or food. Introduction of genes that alter the composition of the grain may greatly enhance the feed or food value. The primary components of maize grain are starch, protein, and oil. Each of these primary components of maize grain may be improved by altering its level or composition. Several examples may be mentioned for illustrative purposes, but in no way provide an exhaustive list of possibilities.

The protein of cereal grains including maize is suboptimal for feed and food purposes especially when fed to pigs, poultry, and humans. The protein is deficient in several amino acids that are essential in the diet of these species, requiring the addition of supplements to the grain. Limiting essential amino acids may include lysine, methionine, tryptophan, threonine, valine, arginine, and histidine. Some amino acids become limiting only after corn is supplemented with other inputs for feed formulations. For example, when corn is supplemented with soybean meal to meet lysine requirements methionine becomes limiting. The levels of these essential amino acids in seeds and grain may be elevated by mechanisms which include, but are not limited to, the introduction of genes to increase the biosynthesis of the amino acids, decrease the degradation of the amino acids, increase the storage of the amino acids in proteins, or increase transport of the amino acids to the seeds or grain.

One mechanism for increasing the biosynthesis of the amino acids is to introduce genes that deregulate the amino acid biosynthetic pathways such that the plant can no longer adequately control the levels that are produced. This may be done by deregulating or bypassing steps in the amino acid biosynthetic pathway which are normally regulated by levels of the amino acid end product of the pathway. Examples include the introduction of genes that encode deregulated versions of the enzymes aspartokinase or dihydrodipicolinic acid (DHDP)-synthase for increasing lysine and threonine production, and anthranilate synthase for increasing tryptophan production. Reduction of the catabolism of the amino acids may be accomplished by introduction of DNA sequences that reduce or eliminate the expression of genes encoding enzymes that catalyze steps in the catabolic pathways such as the enzyme lysine-ketoglutarate reductase. It is anticipated that it may be desirable to target expression of genes relating to amino acid biosynthesis to the endosperm or embryo of the seed. More preferably, the gene will be targeted to the embryo. It will also be preferable for genes encoding proteins involved in amino acid biosynthesis to target the protein to a plastid using a plastid transit peptide sequence.

The protein composition of the grain may be altered to improve the balance of amino acids in a variety of ways including elevating expression of native proteins, decreasing expression of those with poor composition, changing the composition of native proteins, or introducing genes encoding entirely new proteins possessing superior composition. Examples may include the introduction of DNA that decreases the expression of members of the zein family of storage proteins. This DNA may encode ribozymes or antisense sequences directed to impairing expression of zein proteins or expression of regulators of zein expression such as the opaque-2 gene product. It also is proposed that the protein composition of the grain may be modified through the phenomenon of co-suppression, i.e., inhibition of expression of an endogenous gene through the expression of an identical structural gene or gene fragment introduced through transformation (Goring et al., 1991). Additionally, the introduced DNA may encode enzymes which degrade zeins. The decreases in zein expression that are achieved may be accompanied by increases in proteins with more desirable amino acid composition or increases in other major seed constituents such as starch. Alternatively, a chimeric gene may be introduced that comprises a coding sequence for a native protein of adequate amino acid composition such as for one of the globulin proteins or 10 kD delta zein or 20 kD delta zein or 27 kD gamma zein of maize and a promoter or other regulatory sequence designed to elevate expression of said protein. The coding sequence of the gene may include additional or replacement codons for essential amino acids. Further, a coding sequence obtained from another species, or, a partially or completely synthetic sequence encoding a completely unique peptide sequence designed to enhance the amino acid composition of the seed may be employed. It is anticipated that it may be preferable to target expression of these transgenes encoding proteins with superior composition to the endosperm of the seed.

The introduction of genes that alter the oil content of the grain may be of value. Increases in oil content may result in increases in metabolizable-energy-content and density of the seeds for use in feed and food. The introduced genes may encode enzymes that remove or reduce rate-limitations or regulated steps in fatty acid or lipid biosynthesis. Such genes may include, but are not limited to, those that encode acetyl-CoA carboxylase, ACP-acyltransferase, β-ketoacyl-ACP synthase, plus other well known fatty acid biosynthetic activities. Other possibilities are genes that encode proteins that do not possess enzymatic activity such as acyl carrier protein. Genes may be introduced that alter the balance of fatty acids present in the oil providing a more healthful or nutritive feedstuff. The introduced DNA also may encode sequences that block expression of enzymes involved in fatty acid biosynthesis, altering the proportions of fatty acids present in the grain such as described below. Some other examples of genes specifically contemplated by the inventors for use in creating transgenic plants with altered oil composition traits include 2-acetyltransferase, oleosin, pyruvate dehydrogenase complex, acetyl CoA synthetase, ATP citrate lyase, ADP-glucose pyrophosphorylase and genes of the carnitine-CoA-acetyl-CoA shuttles. It is anticipated that expression of genes related to oil biosynthesis will be targeted to the plastid, using a plastid transit peptide sequence and preferably expressed in the seed embryo.

Genes may be introduced that enhance the nutritive value of the starch component of the grain, for example by increasing the degree of branching, resulting in improved utilization of the starch in cows by delaying its metabolism. It is anticipated that expression of genes related to starch biosynthesis will preferably be targeted to the endosperm of the seed.

Besides affecting the major constituents of the grain, genes may be introduced that affect a variety of other nutritive, processing, or other quality aspects of the grain as used for feed or food. For example, pigmentation of the grain may be increased or decreased. Enhancement and stability of yellow pigmentation is desirable in some animal feeds and may be achieved by introduction of genes that result in enhanced production of xanthophylls and carotenes by eliminating rate-limiting steps in their production. Such genes may encode altered forms of the enzymes phytoene synthase, phytoene desaturase, or lycopene synthase. Alternatively, unpigmented white corn is desirable for production of many food products and may be produced by the introduction of DNA which blocks or eliminates steps in pigment production pathways.

Most of the phosphorous content of the grain is in the form of phytate, a form of phosphate storage that is not metabolized by monogastric animals. Therefore, in order to increase the availability of seed phosphate, it is anticipated that one will desire to decrease the amount of phytate in seed and increase the amount of free phosphorous. It is anticipated that one can decrease the expression or activity of one of the enzymes involved in the synthesis of phytate. For example, suppression of expression of the gene encoding inositol phosphate synthetase (INOPS) may lead to an overall reduction in phytate accumulation. It is anticipated that antisense or sense suppression of gene expression may be used. Alternatively, one may express a gene in corn seed which will be activated, e.g., by pH, in the gastric system of a monogastric animal and will release phosphate from phytate. e.g., phytase.

Feed or food comprising primarily maize or other cereal grains possesses insufficient quantities of vitamins and must be supplemented to provide adequate nutritive value. Introduction of genes that enhance vitamin biosynthesis in seeds may be envisioned including, for example, vitamins A, E, $B_{12}$, choline, and the like. Maize grain also does not possess sufficient mineral content for optimal nutritive value. Genes that affect the accumulation or availability of compounds containing phosphorus, sulfur, calcium, manganese, zinc, and iron among others would be valuable. An example may be the introduction of a gene that reduced phytic acid production or encoded the enzyme phytase which enhances phytic acid breakdown. These genes would increase levels of available phosphate in the diet, reducing the need for supplementation with mineral phosphate.

Numerous other examples of improvement of maize or other cereals for feed and food purposes might be described. The improvements may not even necessarily involve the grain, but may, for example, improve the value of the corn for silage. Introduction of DNA to accomplish this might include sequences that alter lignin production such as those that result in the "brown midrib" phenotype associated with superior feed value for cattle.

In addition to direct improvements in feed or food value, genes also may be introduced which improve the processing of corn and improve the value of the products resulting from the processing. The primary method of processing corn is via wetmilling. Maize may be improved though the expression of novel genes that increase the efficiency and reduce the cost of processing such as by decreasing steeping time.

Improving the value of wetmilling products may include altering the quantity or quality of starch, oil, corn gluten meal, or the components of corn gluten feed. Elevation of starch may be achieved through the identification and elimination of rate limiting steps in starch biosynthesis or by decreasing levels of the other components of the grain resulting in proportional increases in starch. An example of the former may be the introduction of genes encoding ADP-glucose pyrophosphorylase enzymes with altered regulatory activity or which are expressed at higher level. Examples of the latter may include selective inhibitors of, for example, protein or oil biosynthesis expressed during later stages of kernel development.

The properties of starch may be beneficially altered by changing the ratio of amylose to amylopectin, the size of the starch molecules, or their branching pattern. Through these changes a broad range of properties may be modified which include, but are not limited to, changes in gelatinization temperature, heat of gelatinization, clarity of films and pastes, rheological properties, and the like. To accomplish these changes in properties, genes that encode granule-bound or soluble starch synthase activity or branching enzyme activity may be introduced alone or combination. DNA such as antisense constructs also may be used to decrease levels of endogenous activity of these enzymes. The introduced genes or constructs may possess regulatory sequences that time their expression to specific intervals in starch biosynthesis and starch granule development. Furthermore, it may be worthwhile to introduce and express genes that result in the in vivo derivatization, or other modification, of the glucose moieties of the starch molecule. The covalent attachment of any molecule may be envisioned, limited only by the existence of enzymes that catalyze the derivatizations and the accessibility of appropriate substrates in the starch granule. Examples of important derivations may include the addition of functional groups such as amines, carboxyls, or phosphate groups which provide sites for subsequent in vitro derivatizations or affect starch properties through the introduction of ionic charges. Examples of other modifications may include direct changes of the glucose units such as loss of hydroxyl groups or their oxidation to aldehyde or carboxyl groups.

Oil is another product of wetmilling of corn, the value of which may be improved by introduction and expression of genes. The quantity of oil that can be extracted by wetmilling may be elevated by approaches as described for feed and food above. Oil properties also may be altered to improve its performance in the production and use of cooking oil, shortenings, lubricants or other oil-derived products or improvement of its health attributes when used in the food-related applications. Novel fatty acids also may be synthesized which upon extraction can serve as starting materials for chemical syntheses. The changes in oil properties may be achieved by altering the type, level, or lipid arrangement of the fatty acids present in the oil. This in turn may be accomplished by the addition of genes that encode enzymes that catalyze the synthesis of novel fatty acids and the lipids possessing them or by increasing levels of native fatty acids while possibly reducing levels of precursors. Alternatively, DNA sequences may be introduced which slow or block steps in fatty acid biosynthesis resulting in the increase in precursor fatty acid intermediates. Genes that might be added include desaturases, epoxidases, hydratases, dehydratases, and other enzymes that catalyze reactions involving fatty acid intermediates. Representative examples of catalytic steps that might be blocked include the desaturations from stearic to oleic acid and oleic to linolenic acid resulting in the respective accumulations of stearic and oleic acids. Another example is the blockage of elongation steps resulting in the accumulation of $C_8$ to $C_{12}$ saturated fatty acids.

Improvements in the other major corn wetmilling products, corn gluten meal and corn gluten feed, also may be achieved by the introduction of genes to obtain novel corn plants. Representative possibilities include but are not limited to those described above for improvement of food and feed value.

In addition, it may further be considered that the corn plant be used for the production or manufacturing of useful biological compounds that were either not produced at all, or not produced at the same level, in the corn plant previously. The novel corn plants producing these compounds are made possible by the introduction and expression of genes by corn transformation methods. The vast array of possibilities include but are not limited to any biological compound which is presently produced by any organism such as proteins, nucleic acids, primary and intermediary metabolites, carbohydrate polymers, etc. The compounds may be produced by the plant, extracted upon harvest and/or processing, and used for any presently recognized useful purpose such as pharmaceuticals, fragrances, and industrial enzymes to name a few.

Further possibilities to exemplify the range of grain traits or properties potentially encoded by introduced genes in transgenic plants include grain with less breakage susceptibility for export purposes or larger grit size when processed by dry milling through introduction of genes that enhance γ-zein synthesis, popcorn with improved popping quality and expansion volume through genes that increase pericarp thickness, corn with whiter grain for food uses though introduction of genes that effectively block expression of enzymes involved in pigment production pathways, and improved quality of alcoholic beverages or sweet corn through introduction of genes which affect flavor such as the shrunken 1 gene (encoding sucrose synthase) or shrunken 2 gene (encoding ADPG pyrophosphorylase) for sweet corn.

(vii) Plant Agronomic Characteristics

Two of the factors determining where crop plants can be grown are the average daily temperature during the growing season and the length of time between frosts. Within the areas where it is possible to grow a particular crop, there are varying limitations on the maximal time it is allowed to grow to maturity and be harvested. For example, maize to be grown in a particular area is selected for its ability to mature and dry down to harvestable moisture content within the required period of time with maximum possible yield. Therefore, corn of varying maturities is developed for different growing locations. Apart from the need to dry down sufficiently to permit harvest, it is desirable to have maximal drying take place in the field to minimize the amount of energy required for additional drying post-harvest. Also, the more readily the grain can dry down, the more time there is available for growth and kernel fill. It is considered that genes that influence maturity and/or dry down can be identified and introduced into corn or other plants using transformation techniques to create new varieties adapted to different growing locations or the same growing location, but having improved yield to moisture ratio at harvest. Expression of genes that are involved in regulation of plant development may be especially useful, e.g., the liguleless and rough sheath genes that have been identified in corn.

It is contemplated that genes may be introduced into plants that would improve standability and other plant growth characteristics. Expression of novel genes in maize which confer stronger stalks, improved root systems, or prevent or reduce ear droppage would be of great value to the farmer. It is proposed that introduction and expression of genes that increase the total amount of photoassimilate available by, for example, increasing light distribution and/or interception would be advantageous. In addition, the expression of genes that increase the efficiency of photosynthesis and/or the leaf canopy would further increase gains in productivity. It is contemplated that expression of a phytochrome gene in corn may be advantageous. Expression of such a gene may reduce apical dominance, confer semi-dwarfism on a plant, and increase shade tolerance (U.S. Pat. No. 5,268,526). Such approaches would allow for increased plant populations in the field.

Delay of late season vegetative senescence would increase the flow of assimilate into the grain and thus increase yield. It is proposed that overexpression of genes within corn that are associated with "stay green" or the expression of any gene that delays senescence would be advantageous. For example, a nonyellowing mutant has been identified in *Festuca pratensis* (Davies et al., 1990). Expression of this gene as well as others may prevent premature breakdown of chlorophyll and thus maintain canopy function.

(viii) Nutrient Utilization

The ability to utilize available nutrients may be a limiting factor in growth of monocotyledonous plants such as maize. It is proposed that it would be possible to alter nutrient uptake, tolerate pH extremes, mobilization through the plant, storage pools, and availability for metabolic activities by the introduction of novel genes. These modifications would allow a plant such as maize to more efficiently utilize available nutrients. It is contemplated that an increase in the activity of, for example, an enzyme that is normally present in the plant and involved in nutrient utilization would increase the availability of a nutrient. An example of such an enzyme would be phytase. It further is contemplated that enhanced nitrogen utilization by a plant is desirable. Expression of a glutamate dehydrogenase gene in corn, e.g., *E. coli* gdhA genes, may lead to increased fixation of nitrogen in organic compounds. Furthermore, expression of gdhA in corn may lead to enhanced resistance to the herbicide glufosinate by incorporation of excess ammonia into glutamate, thereby detoxifying the ammonia. It also is contemplated that expression of a novel gene may make a nutrient source available that was previously not accessible, e.g., an enzyme that releases a component of nutrient value from a more complex molecule, perhaps a macromolecule.

(ix) Male Sterility

Male sterility is useful in the production of hybrid seed. It is proposed that male sterility may be produced through expression of novel genes. For example, it has been shown that expression of genes that encode proteins that interfere with development of the male inflorescence and/or gametophyte result in male sterility. Chimeric ribonuclease genes that express in the anthers of transgenic tobacco and oilseed rape have been demonstrated to lead to male sterility (Mariani et al., 1990).

A number of mutations were discovered in maize that confer cytoplasmic male sterility. One mutation in particular, referred to as T cytoplasm, also correlates with sensitivity to Southern corn leaf blight. A DNA sequence, designated TURF-13 (Levings, 1990), was identified that correlates with T cytoplasm. It is proposed that it would be possible through the introduction of TURF-13 via transformation, to separate male sterility from disease sensitivity. As it is necessary to be able to restore male fertility for breeding purposes and for grain production, it is proposed that genes encoding restoration of male fertility also may be introduced.

(x) Negative Selectable Markers

Introduction of genes encoding traits that can be selected against may be useful for eliminating undesirable linked genes. It is contemplated that when two or more genes are introduced together by cotransformation that the genes will be linked together on the host chromosome. For example, a gene encoding Bt that confers insect resistance on the plant may be introduced into a plant together with a bar gene that is useful as a selectable marker and confers resistance to the herbicide Liberty® on the plant. However, it may not be desirable to have an insect resistant plant that also is resistant to the herbicide Liberty®. It is proposed that one also could introduce an antisense bar coding region that is expressed in those tissues where one does not want expression of the bar gene product, e.g., in whole plant parts. Hence, although the bar gene is expressed and is useful as a selectable marker, it is not useful to confer herbicide resistance on the whole plant. The bar antisense gene is a negative selectable marker.

It also is contemplated that negative selection is necessary in order to screen a population of transformants for rare homologous recombinants generated through gene targeting. For example, a homologous recombinant may be identified through the inactivation of a gene that was previously expressed in that cell. The antisense construct for neomycin phosphotransferase II (NPT II) has been investigated as a negative selectable marker in tobacco (*Nicotiana tabacum*) and *Arabidopsis thaliana* (Xiang. and Guerra, 1993). In this example, both sense and antisense NPT II genes are introduced into a plant through transformation and the resultant plants are sensitive to the antibiotic kanamycin. An introduced gene that integrates into the host cell chromosome at the site of the antisense NPT II gene, and inactivates the antisense gene, will make the plant resistant to kanamycin and other aminoglycoside antibiotics. Therefore, rare, site-specific recombinants may be identified by screening for antibiotic resistance. Similarly, any gene, native to the plant or introduced through transformation, that when inactivated confers resistance to a compound, may be useful as a negative selectable marker.

It is contemplated that negative selectable markers also may be useful in other ways. One application is to construct transgenic lines in which one could select for transposition to unlinked sites. In the process of tagging it is most common for the transposable element to move to a genetically linked site on the same chromosome. A selectable marker for recovery of rare plants in which transposition has occurred to an unlinked locus would be useful. For example, the enzyme cytosine deaminase may be useful for this purpose (Stouggard, 1993). In the presence of this enzyme the compound 5-fluorocytosine is converted to 5-fluorouracil which is toxic to plant and animal cells. If a transposable element is linked to the gene for the enzyme cytosine deaminase, one may select for transposition to unlinked sites by selecting for transposition events in which the resultant plant is now resistant to 5-fluorocytosine. The parental plants and plants containing transpositions to linked sites will remain sensitive to 5-fluorocytosine. Resistance to 5-fluorocytosine is due to loss of the cytosine deaminase gene through genetic segregation of the transposable element and the cytosine deaminase gene. Other genes that encode proteins that render the plant sensitive to a certain compound will also be useful in this context. For example, T-DNA gene 2 from *Agrobacterium tumefaciens* encodes a protein that catalyzes the conversion of α-naphthalene acetamide (NAM) to α-naphthalene acetic acid (NAA) renders plant cells sensitive to high concentrations of NAM (Depicker et al., 1988).

It also is contemplated that negative selectable markers may be useful in the construction of transposon tagging lines. For example, by marking an autonomous transposable element such as Ac, Master Mu, or En/Spn with a negative selectable marker, one could select for transformants in which the autonomous element is not stably integrated into the genome. It is proposed that this would be desirable, for example, when transient expression of the autonomous element is desired to activate in trans the transposition of a defective transposable element, such as Ds, but stable integration of the autonomous element is not desired. The presence of the autonomous element may not be desired in order to stabilize the defective element, i.e., prevent it from further transposing. However, it is proposed that if stable integration of an autonomous transposable element is desired in a plant the presence of a negative selectable marker may make it possible to eliminate the autonomous element during the breeding process.

(xi) Non-Protein-Expressing Sequences

DNA may be introduced into plants for the purpose of expressing RNA transcripts that function to affect plant phenotype yet are not translated into protein. Two examples are antisense RNA and RNA with ribozyme activity. Both may serve possible functions in reducing or eliminating expression of native or introduced plant genes. However, as detailed below, DNA need not be expressed to effect the phenotype of a plant.

1. Antisense RNA

Genes may be constructed or isolated, which when transcribed, produce antisense RNA that is complementary to all or part(s) of a targeted messenger RNA(s). The antisense RNA reduces production of the polypeptide product of the messenger RNA. The polypeptide product may be any protein encoded by the plant genome. The aforementioned genes will be referred to as antisense genes. An antisense gene may thus be introduced into a plant by transformation methods to produce a novel transgenic plant with reduced expression of a selected protein of interest. For example, the protein may be an enzyme that catalyzes a reaction in the plant. Reduction of the enzyme activity may reduce or eliminate products of the reaction which include any enzymatically synthesized compound in the plant such as fatty acids, amino acids, carbohydrates, nucleic acids and the like. Alternatively, the protein may be a storage protein, such as a zein, or a structural protein, the decreased expression of which may lead to changes in seed amino acid composition or plant morphological changes respectively. The possibilities cited above are provided only by way of example and do not represent the full range of applications.

2. Ribozymes

Genes also may be constructed or isolated, which when transcribed, produce RNA enzymes (ribozymes) which can act as endoribonucleases and catalyze the cleavage of RNA molecules with selected sequences. The cleavage of selected messenger RNAs can result in the reduced production of their encoded polypeptide products. These genes may be used to prepare novel transgenic plants which possess them. The transgenic plants may possess reduced levels of polypeptides including, but not limited to, the polypeptides cited above.

Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cech et al., 1981). For example, U.S. Pat. No. 5,354,855 reports that certain ribozymes can act as endonucleases with a sequence specificity greater than that of known ribonucleases and approaching that of the DNA restriction enzymes.

Several different ribozyme motifs have been described with RNA cleavage activity (Symons, 1992). Examples include sequences from the Group I self splicing introns including Tobacco Ringspot Virus (Prody et al., 1986), Avocado Sunblotch Viroid (Palukaitis et al., 1979; Symons, 1981), and Lucerne Transient Streak Virus (Forster and Symons, 1987). Sequences from these and related viruses are referred to as hammerhead ribozyme based on a predicted folded secondary structure.

Other suitable ribozymes include sequences from RNase P with RNA cleavage activity (Yuan et al., 1992, Yuan and Altman, 1994, U.S. Pat. Nos. 5,168,053 and 5,624,824), hairpin ribozyme structures (Berzal-Herranz et al., 1992; Chowrira et al., 1993) and Hepatitis Delta virus based ribozymes (U.S. Pat. No. 5,625,047). The general design and optimization of ribozyme directed RNA cleavage activity has been discussed in detail (Haseloff and Gerlach, 1988, Symons, 1992, Chowrira et al., 1994; Thompson et al., 1995).

The other variable on ribozyme design is the selection of a cleavage site on a given target RNA. Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozyme, the cleavage site is a dinucleotide sequence on the target RNA is a uracil (U) followed by either an adenine, cytosine or uracil (A,C or U) (Perriman et al., 1992; Thompson et al., 1995). The frequency of this dinucleotide occurring in any given RNA is statistically 3 out of 16. Therefore, for a given target messenger RNA of 1000 bases, 187 dinucleotide cleavage sites are statistically possible.

Designing and testing ribozymes for efficient cleavage of a target RNA is a process well known to those skilled in the art. Examples of scientific methods for designing and testing ribozymes are described by Chowrira et al., (1994) and Lieber and Strauss (1995), each incorporated by reference. The identification of operative and preferred sequences for use in down regulating a given gene is simply a matter of preparing and testing a given sequence, and is a routinely practiced "screening" method known to those of skill in the art.

3. Induction of Gene Silencing

It also is possible that genes may be introduced to produce novel transgenic plants which have reduced expression of a native gene product by the mechanism of co-suppression. It has been demonstrated in tobacco, tomato, and petunia (Goring et al., 1991; Smith et al., 1990; Napoli et al., 1990; van der Krol et al., 1990) that expression of the sense transcript of a native gene will reduce or eliminate expression of the native gene in a manner similar to that observed for antisense genes. The introduced gene may encode all or part of the targeted native protein but its translation may not be required for reduction of levels of that native protein.

4. Non-RNA-Expressing Sequences

DNA elements including those of transposable elements such as Ds, Ac, or Mu, may be inserted into a gene to cause mutations. These DNA elements may be inserted in order to inactivate (or activate) a gene and thereby "tag" a particular trait. In this instance the transposable element does not cause instability of the tagged mutation, because the utility of the element does not depend on its ability to move in the genome. Once a desired trait is tagged, the introduced DNA sequence may be used to clone the corresponding gene, e.g., using the introduced DNA sequence as a PCR primer together with PCR gene cloning techniques (Shapiro, 1983; Dellaporta et al., 1988). Once identified, the entire gene(s) for the particular trait, including control or regulatory regions where desired, may be isolated, cloned and manipulated as desired. The utility of DNA elements introduced into an organism for purposes of gene tagging is independent of the DNA sequence and does not depend on any biological activity of the DNA sequence, i.e., transcription into RNA or translation into protein. The sole function of the DNA element is to disrupt the DNA sequence of a gene.

It is contemplated that unexpressed DNA sequences, including novel synthetic sequences, could be introduced into cells as proprietary "labels" of those cells and plants and seeds thereof. It would not be necessary for a label DNA element to disrupt the function of a gene endogenous to the host organism, as the sole function of this DNA would be to identify the origin of the organism. For example, one could introduce a unique DNA sequence into a plant and this DNA element would identify all cells, plants, and progeny of these cells as having arisen from that labeled source. It is proposed that inclusion of label DNAs would enable one to distinguish proprietary germplasm or germplasm derived from such, from unlabelled germplasm.

Another possible element which may be introduced is a matrix attachment region element (MAR), such as the chicken lysozyme A element (Stief, 1989), which can be positioned around an expressible gene of interest to effect an increase in overall expression of the gene and diminish position dependent effects upon incorporation into the plant genome (Stief et al., 1989; Phi-Van et al., 1990).

IV. Assays of Transgene Expression

Assays may be employed with the instant invention for determination of the relative efficiency of transgene expression. For example, assays may be used to determine the efficacy of deletion mutants of the RS81 promoter in directing expression of exogenous proteins. Similarly, one could produce random or site-specific mutants of the RS81 promoter of the invention and assay the efficacy of the mutants in the expression of a given transgene. Alternatively, assays could be used to determine the efficacy of the RS81 promoter in directing protein expression when used in conjunction with various different enhancers, terminators or other types of elements potentially used in the preparation of transformation constructs.

For plants, expression assays may comprise a system utilizing embryogenic or non-embryogenic cells, or alternatively, whole plants. An advantage of using cellular assays is that regeneration of large numbers of plants is not required. However, the systems are limited in that promoter activity in the non-regenerated cells may not directly correlate with expression in a plant. Additionally, assays of tissue or developmental specific promoters are generally not feasible.

The biological sample to be assayed may comprise nucleic acids isolated from the cells of any plant material according to standard methodologies (Sambrook et al., 1989). The nucleic acid may be genomic DNA or fractionated or whole cell RNA. Where RNA is used, it may be desired to convert the RNA to a complementary DNA. In one embodiment of the invention, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Following detection, one may compare the results seen in a given plant with a statistically significant reference group of non-transformed control plants. Typically, the non-transformed control plants will be of a genetic background similar to the transformed plants. In this way, it is possible to detect differences in the amount or kind of protein detected in various transformed plants. Alternatively, clonal cultures of cells, for example, callus or an immature embryo, may be compared to other cells samples.

As indicated, a variety of different assays are contemplated in the screening of cells or plants of the current invention and associated promoters. These techniques may in cases be used to detect for both the presence and expression of the particular genes as well as rearrangements that may have occurred in the gene construct. The techniques include but are not limited to, fluorescent in situ hybridization (FISH), direct DNA sequencing, pulsed field gel electrophoresis (PFGE) analysis, Southern or Northern blotting, single-stranded conformation analysis (SSCA), RNAse protection assay, allele-specific oligonucleotide (ASO), dot blot analysis, denaturing gradient gel electrophoresis, RFLP and PCR™-SSCP.

(i) Quantitation of Gene Expression with Relative Quantitative RT-PCR™

Reverse transcription (RT) of RNA to cDNA followed by relative quantitative PCR™ (RT-PCR™) can be used to determine the relative concentrations of specific mRNA species isolated from plants. By determining that the concentration of a specific mRNA species varies, it is shown that the gene encoding the specific mRNA species is differentially expressed. In this way, a promoters expression profile can be rapidly identified, as can the efficacy with which the promoter directs transgene expression.

In PCR™, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR™ amplification is directly proportional to the starting concentration of the target before the reaction began. By determining the concentration of the amplified products of the target DNA in PCR™ reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR™ products and the relative mRNA abundances is only true in the linear range of the PCR™ reaction.

The final concentration of the target DNA in the plateau portion of the curve is determined by the availability of reagents in the reaction mix and is independent of the original concentration of target DNA. Therefore, the first condition that must be met before the relative abundances of a mRNA species can be determined by RT-PCR™ for a collection of RNA populations is that the concentrations of the amplified PCR™ products must be sampled when the PCR™ reactions are in the linear portion of their curves.

The second condition that must be met for an RT-PCR™ study to successfully determine the relative abundances of a particular mRNA species is that relative concentrations of the amplifiable cDNAs must be normalized to some independent standard. The goal of an RT-PCR™ study is to determine the abundance of a particular mRNA species relative to the average abundance of all mRNA species in the sample.

Most protocols for competitive PCR™ utilize internal PCR™ standards that are approximately as abundant as the target. These strategies are effective if the products of the PCR™ amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR™ assay for plant tissue. The problems inherent in plant tissue samples are that they are of variable quantity (making normalization problematic), and that they are of variable quality (necessitating the co-amplification of a reliable internal control, preferably of larger size than the target). Both of these problems are overcome if the RT-PCR™ is performed as a relative quantitative RT-PCR™ with an internal standard in which the internal standard is an amplifiable cDNA fragment that is larger than the target cDNA fragment and in which the abundance of the mRNA encoding the internal standard is roughly 5–100 fold higher than the mRNA encoding the target. This assay measures relative abundance, not absolute abundance of the respective mRNA species.

Other studies may be performed using a more conventional relative quantitative RT-PCR™ assay with an external standard protocol. These assays sample the PCR™ products in the linear portion of their amplification curves. The number of PCR™ cycles that are optimal for sampling must be empirically determined for each target cDNA fragment. In addition, the reverse transcriptase products of each RNA population isolated from the various tissue samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR™ assays can be superior to those derived from the relative quantitative RT-PCR™ assay with an internal standard.

One reason for this advantage is that without the internal standard/competitor, all of the reagents can be converted into a single PCR™ product in the linear range of the amplification curve, thus increasing the sensitivity of the assay. Another reason is that with only one PCR™ product, display of the product on an electrophoretic gel or another display method becomes less complex, has less background and is easier to interpret.

(ii) Marker Gene Expression

Marker genes represent an efficient means for assaying the expression of transgenes. Using, for example, a selectable marker gene, one could quantitatively determine the resistance conferred upon a plant or plant cell by a construct comprising the selectable marker coding region operably linked to the promoter to be assayed, e.g., an RS81 promoter. Alternatively, various plant parts could be exposed to a selective agent and the relative resistance provided in these parts quantified, thereby providing an estimate of the tissue specific expression of the promoter.

Screenable markers constitute another efficient means for quantifying the expression of a given transgene. Potentially any screenable marker could be expressed and the marker gene product quantified, thereby providing an estimate of the efficiency with which the promoter directs expression of the transgene. Quantification can readily be carried out using either visual means, or, for example, a photon counting device.

A preferred screenable marker gene assay for use with the current invention constitutes the use of the screenable marker gene β-glucuronidase (GUS). Detection of GUS activity can be performed histochemically using 5-bromo-4-chloro-3-indolyl glucuronide (X-gluc) as the substrate for the GUS enzyme, yielding a blue precipitate inside of cells containing GUS activity. This assay has been described in detail (Jefferson, 1987). The blue coloration can then be visually scored, and estimates of expression efficiency thereby provided. GUS activity also can be determined by immunoblot analysis or a fluorometric GUS specific activity assay (Jefferson, 1987).

(iii) Purification and Assays of Proteins

One means for determining the efficiency with which a particular transgene is expressed is to purify and quantify a polypeptide expressed by the transgene. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; and isoelectric focusing. A particularly efficient method of purifying peptides is fast protein liquid chromatography or even HPLC.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide being assayed always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

V. Methods for Plant Transformation

Suitable methods for plant transformation for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by Agrobacterium-mediated transformation (U.S. Pat. No. 5,591,616 and U.S. Pat. No. 5,563,055; both specifically incorporated herein by reference) and by acceleration of DNA coated particles (U.S. Pat. No. 5,550,318; U.S. Pat. No. 5,538,877; and U.S. Pat. No. 5,538,880; each specifically incorporated herein by reference in its entirety), etc. Through the application of techniques such as these, maize cells as well as those of virtually any other plant species may be stably transformed, and these cells developed into transgenic plants. In certain embodiments, acceleration methods are preferred and include, for example, microprojectile bombardment and the like.

(i) Electroporation

Where one wishes to introduce DNA by means of electroporation, it is contemplated that the method of Krzyzek et al. (U.S. Pat. No. 5,384,253, incorporated herein by reference in its entirety) will be particularly advantageous. In this method, certain cell wall-degrading enzymes, such as pectin-degrading enzymes, are employed to render the target recipient cells more susceptible to transformation by electroporation than untreated cells. Alternatively, recipient cells are made more susceptible to transformation by mechanical wounding.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

(ii) Microprojectile Bombardment

A preferred method for delivering transforming DNA segments to plant cells in accordance with the invention is microprojectile bombardment (U.S. Pat. No. 5,550,318; U.S. Pat. No. 5,538,880; U.S. Pat. No. 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al. 1994), peanut (Singsit et al., 1997), cotton (McCabe and Martinell, 1993), tomato (VanEck et al. 1995), and legumes in general (U.S. Pat. No. 5,563,055, specifically incorporated herein by reference in its entirety).

(iii) Agrobacterium-mediated Transformation

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

Agrobacterium-mediated transformation is most efficient in dicotyledonous plants and is the preferable method for transformation of dicots, including Arabidopsis, tobacco, tomato, and potato. Indeed, while Agrobacterium-mediated transformation has been routinely used with dicotyledonous plants for a number of years, it has only recently become applicable to monocotyledonous plants. Advances in Agrobacterium-mediated transformation techniques have now made the technique applicable to nearly all monocotyledonous plants. For example, Agrobacterium-mediated transformation techniques have now been applied to rice (Hiei et al., 1997; Zhang et al., 1997; U.S. Pat No. 5,591, 616, specifically incorporated herein by reference in its entirety), wheat (McCormac et al., 1998), barley (Tingay et al., 1997; McCormac et al., 1998), and maize (Ishidia et al., 1996).

Modern Agrobacterium transformation vectors are capable of replication in *E. coli* as well as Agrobacterium, allowing for convenient manipulations as described (Klee et al., 1985). Moreover, recent technological advances in vectors for Agrobacterium-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, Agrobacterium containing both armed and disarmed Ti genes can be used for the transformations. In those plant strains where Agrobacterium-mediated transformation is efficient, it is the method of choice because of the facile and defined nature of the gene transfer.

(iv) Other Transformation Methods

Transformation of plant protoplasts can be achieved using methods based on calcium phosphate precipitation, polyethylene glycol treatment, electroporation, and combinations of these treatments (see, e.g, Potrykus et al., 1985; Lorz et al., 1985; Omirulleh et al., 1993; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts have been described (Fujimara et al., 1985; Toriyama et al., 1986; Yamada et al, 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

To transform plant strains that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055, specifically incorporated herein by reference in its entirety). Transformation with this technique is accomplished by agitating silicon carbide fibers together with cells in a DNA solution. DNA passively enters as the cell are punctured. This technique has been used successfully with, for example, the monocot cereals maize (PCT Application WO 95/06128, specifically incorporated herein by reference in its entirety; Thompson, 1995) and rice (Nagatani, 1997).

VI. Optimization of Microprojectile Bombardment

For microprojectile bombardment transformation in accordance with the current invention, both physical and biological parameters may be optimized. Physical factors are those that involve manipulating the DNA/microprojectile precipitate or those that affect the flight and velocity of either the macro- or microprojectiles. Biological factors include all steps involved in manipulation of cells before and immediately after bombardment, such as the osmotic adjustment of target cells to help alleviate the trauma associated with bombardment, the orientation of an immature embryo or other target tissue relative to the particle trajectory, and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust various of the bombardment parameters in small scale studies to fully optimize the conditions. One may particularly wish to adjust physical parameters such as DNA concentration, gap distance, flight distance, tissue distance, and helium pressure. It further is contemplated that the grade of helium may effect transformation efficiency. For example, differences in transformation efficiencies may be witnessed between bombardments using industrial grade (99.99% pure) or ultra pure helium (99.999% pure), although it is not currently clear which is more advantageous for use in bombardment. One also may optimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation.

(i) Physical Parameters

1. Gap Distance

The variable nest (macro holder) can be adjusted to vary the distance between the rupture disk and the macroprojectile, i.e., the gap distance. This distance can be varied from 0 to 2 cm. The predicted effects of a shorter gap are an increase of velocity of both the macro- and microprojectiles, an increased shock wave (which leads to tissue splattering and increased tissue trauma), and deeper penetration of microprojectiles. Longer gap distances would have the opposite effects but may increase viability and therefore the total number of recovered stable transformants.

2. Flight Distance

The fixed nest (contained within the variable nest) can be varied between 0.5 and 2.25 cm in predetermined 0.5 cm increments by the placement of spacer rings to adjust the flight path traversed by the macroprojectile. Short flight paths allow for greater stability of the macroprojectile in flight but reduce the overall velocity of the microprojectiles. Increased stability in flight increases, for example, the number of centered GUS foci. Greater flight distances (up to some point) increase velocity but also increase instability in flight. Based on observations, it is recommended that bombardments typically be done with a flight path length of about 1.0 cm to 1.5 cm.

3. Tissue Distance

Placement of tissue within the gun chamber can have significant effects on microprojectile penetration. Increasing the flight path of the microprojectiles will decrease velocity and trauma associated with the shock wave. A decrease in velocity also will result in shallower penetration of the microprojectiles.

4. Helium Pressure

By manipulation of the type and number of rupture disks, pressure can be varied between 400 and 2000 psi within the gas acceleration tube. Optimum pressure for stable transformation has been determined to be between 1000 and 1200 psi.

5. Coating of Microprojectiles.

For microprojectile bombardment, one will attach (i.e. "coat") DNA to the microprojectiles such that it is delivered to recipient cells in a form suitable for transformation thereof. In this respect, at least some of the transforming DNA must be available to the target cell for transformation to occur, while at the same time during delivery the DNA must be attached to the microprojectile. Therefore, availability of the transforming DNA from the microprojectile may comprise the physical reversal of bonds between transforming DNA and the microprojectile following delivery of the microprojectile to the target cell. This need not be the case, however, as availability to a target cell may occur as a result of breakage of unbound segments of DNA or of other molecules which comprise the physical attachment to the microprojectile. Availability may further occur as a result of breakage of bonds between the transforming DNA and other molecules, which are either directly or indirectly attached to the microprojectile. It further is contemplated that transformation of a target cell may occur by way of direct recombination between the transforming DNA and the genomic DNA of the recipient cell. Therefore, as used herein, a "coated" microprojectile will be one which is capable of being used to transform a target cell, in that the transforming DNA will be delivered to the target cell, yet will be accessible to the target cell such that transformation may occur.

Any technique for coating microprojectiles which allows for delivery of transforming DNA to the target cells may be used. Methods for coating microprojectiles which have been demonstrated to work well with the current invention have been specifically disclosed herein. DNA may be bound to microprojectile particles using alternative techniques, however. For example, particles may be coated with streptavidin and DNA end labeled with long chain thiol cleavable biotinylated nucleotide chains. The DNA adheres to the particles due to the streptavidin-biotin interaction, but is released in the cell by reduction of the thiol linkage through reducing agents present in the cell.

Alternatively, particles may be prepared by functionalizing the surface of a gold oxide particle, providing free amine groups. DNA, having a strong negative charge, binds to the functionalized particles. Furthermore, charged particles may be deposited in controlled arrays on the surface of mylar flyer disks used in the PDS-1000 Biolistics device, thereby facilitating controlled distribution of particles delivered to target tissue.

As disclosed above, it further is proposed, that the concentration of DNA used to coat microprojectiles may influence the recovery of transformants containing a single copy of the transgene. For example, a lower concentration of DNA may not necessarily change the efficiency of the transformation, but may instead increase the proportion of single copy insertion events. In this regard, approximately 1 ng to 2000 ng of transforming DNA may be used per each 1.8 mg of starting microprojectiles. In other embodiments of the invention, approximately 2.5 ng to 1000 ng, 2.5 ng to 750 ng, 2.5 ng to 500 ng, 2.5 ng to 250 ng, 2.5 ng to 100 ng, or 2.5 ng to 50 ng of transforming DNA may be used per each 1.8 mg of starting microprojectiles.

Various other methods also may be used to increase transformation efficiency and/or increase the relative proportion of low-copy transformation events. For example, the inventors contemplate end-modifying transforming DNA with alkaline phosphatase or an agent which will blunt DNA ends prior to transformation. Still further, an inert carrier DNA may be included with the transforming DNA, thereby lowering the effective transforming DNA concentration without lowering the overall amount of DNA used. These techniques are further described in U.S. patent application Ser. No. 08/995,451, filed Dec. 22, 1997, the disclosure of which is specifically incorporated herein by reference in its entirety.

(ii) Biological Parameters

Culturing conditions and other factors can influence the physiological state of the target cells and may have profound effects on transformation and integration efficiencies. First, the act of bombardment could stimulate the production of ethylene which could lead to senescence of the tissue. The addition of antiethylene compounds could increase transformation efficiencies. Second, it is proposed that certain points in the cell cycle may be more appropriate for integration of introduced DNA. Hence synchronization of cell cultures may enhance the frequency of production of transformants. For example, synchronization may be achieved using cold treatment, amino acid starvation, or other cell cycle-arresting agents. Third, the degree of tissue hydration also may contribute to the amount of trauma associated with bombardment as well as the ability of the microprojectiles to penetrate cell walls.

The position and orientation of an embryo or other target tissue relative to the particle trajectory also may be important. For example, the PDS-1000 biolistics device does not produce a uniform spread of particles over the surface of a target petri dish. The velocity of particles in the center of the plate is higher than the particle velocity at further distances from the center of the petri dish. Therefore, it is advantageous to situate target tissue on the petri dish such as to avoid the center of the dish, referred to by some as the "zone of death." Furthermore, orientation of the target tissue with regard to the trajectory of targets also can be important. It is contemplated that it is desirable to orient the tissue most likely to regenerate a plant toward the particle stream. For example, the scutellum of an immature embryo comprises the cells of greatest embryogenic potential and therefore should be oriented toward the particle stream.

It also has been reported that slightly plasmolyzed yeast cells allow increased transformation efficiencies (Armaleo et al., 1990). It was hypothesized that the altered osmotic state of the cells helped to reduce trauma associated with the penetration of the microprojectile. Additionally, the growth and cell cycle stage may be important with respect to transformation.

1. Osmotic Adjustment

It has been suggested that osmotic pre-treatment could potentially reduce bombardment associated injury as a result of the decreased turgor pressure of the plasmolyzed cell. In a previous study, the number of cells transiently expressing GUS increased following subculture into both fresh medium and osmotically adjusted medium (PCT Application WO 95/06128, specifically incorporated herein by reference in its entirety). Pretreatment times of 90 minutes showed higher numbers of GUS expressing foci than shorter times. Cells incubated in 500 mOSM/kg medium for 90 minutes showed an approximately 3.5 fold increase in transient GUS foci than the control. Preferably, immature embryos are precultured for 4–5 hours prior to bombardment on culture medium containing 12% sucrose. A second culture on 12% sucrose is performed for 16–24 hours following bombardment. Alternatively, type II cells are pretreated on 0.2M mannitol for 3–4 hours prior to bombardment. It is contemplated that pretreatment of cells with other osmotically active solutes for a period of 1–6 hours also may be desirable.

2. Plasmid Configuration

In some instances, it will be desirable to deliver DNA to maize cells that does not contain DNA sequences necessary for maintenance of the plasmid vector in the bacterial host, e.g., E. coli, such as antibiotic resistance genes, including but not limited to ampicillin, kanamycin, and tetracycline resistance, and prokaryotic origins of DNA replication. In such case, a DNA fragment containing the transforming DNA may be purified prior to transformation. An exemplary method of purification is gel electrophoresis on a 1.2% low melting temperature agarose gel, followed by recovery from the agarose gel by melting gel slices in a 6–10 fold excess of Tris-EDTA buffer (10 mM Tris-HCl pH 8.0, 1 mM EDTA, 70° C.–72° C.); frozen and thawed (37° C.); and the agarose pelleted by centrifugation. A Qiagen Q-100 column then may be used for purification of DNA. For efficient recovery of DNA, the flow rate of the column may be adjusted to 40 ml/hr.

Isolated DNA fragments can be recovered from agarose gels using a variety of electroelution techniques, enzyme digestion of the agarose, or binding of DNA to glass beads (e.g., Gene Clean). In addition, HPLC and/or use of magnetic particles may be used to isolate DNA fragments. As an alternative to isolation of DNA fragments, a plasmid vector can be digested with a restriction enzyme and this DNA delivered to maize cells without prior purification of the expression cassette fragment.

VII. Recipient Cells for Transformation

Tissue culture requires media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Nutrient media is prepared as a liquid, but this may be solidified by adding the liquid to materials capable of providing a solid support. Agar is most commonly used for this purpose. Bactoagar, Hazelton agar, Gelrite, and Gelgro are specific types of solid support that are suitable for growth of plant cells in tissue culture.

Some cell types will grow and divide either in liquid suspension or on solid media. As disclosed herein, plant cells will grow in suspension or on solid medium, but regeneration of plants from suspension cultures typically requires transfer from liquid to solid media at some point in development. The type and extent of differentiation of cells in culture will be affected not only by the type of media used and by the environment, for example, pH, but also by whether media is solid or liquid. Table 7 illustrates the composition of various media useful for creation of recipient cells and for plant regeneration.

Recipient cell targets include, but are not limited to, meristem cells, Type I, Type II, and Type III callus, immature embryos and gametic cells such as microspores, pollen, sperm and egg cells. It is contemplated that any cell from which a fertile plant may be regenerated is useful as a recipient cell. Type I, Type II, and Type III callus may be initiated from tissue sources including, but not limited to, immature embryos, seedling apical meristems, microspores and the like. Those cells which are capable of proliferating as callus also are recipient cells for genetic transformation. The present invention provides techniques for transforming immature embryos and subsequent regeneration of fertile transgenic plants. Transformation of immature embryos obviates the need for long term development of recipient cell cultures. Pollen, as well as its precursor cells, microspores, may be capable of functioning as recipient cells for genetic transformation, or as vectors to carry foreign DNA for incorporation during fertilization Direct pollen transformation would obviate the need for cell culture. Meristematic cells (i e., plant cells capable of continual cell division and characterized by an undifferentiated cytological appearance, normally found at growing points or tissues in plants such as root tips, stem apices, lateral buds, etc.) may represent another type of recipient plant cell. Because of their undifferentiated growth and capacity for organ differentiation and totipotency, a single transformed meristematic cell could be recovered as a whole transformed plant. In fact, it is proposed that embryogenic suspension cultures may be an in vitro meristematic cell system, retaining an ability for continued cell division in an undifferentiated state, controlled by the media environment.

Cultured plant cells that can serve as recipient cells for transforming with desired DNA segments may be any plant cells including corn cells, and more specifically, cells from Zea mays L. Somatic cells are of various types. Embryogenic cells are one example of somatic cells which may be induced to regenerate a plant through embryo formation. Non-embryogenic cells are those which typically will not respond in such a fashion. An example of non-embryogenic cells are certain Black Mexican Sweet (BMS) corn cells.

The development of embryogenic maize calli and suspension cultures useful in the context of the present invention, e.g., as recipient cells for transformation, has been described in U.S. Pat. No. 5,134,074; and U.S. Pat. No. 5,489,520; each of which is incorporated herein by reference in its entirety.

Certain techniques may be used that enrich recipient cells within a cell population. For example, Type II callus development, followed by manual selection and culture of friable, embryogenic tissue, generally results in an enrichment of recipient cells for use in, microprojectile transformation. Suspension culturing, particularly using the media disclosed herein, may improve the ratio of recipient to non-recipient cells in any given population. Manual selection techniques which can be employed to select recipient cells may include, e.g., assessing cell morphology and differentiation, or may use various physical or biological means. Cryopreservation also is a possible method of selecting for recipient cells.

Manual selection of recipient cells, e.g., by selecting embryogenic cells from the surface of a Type II callus, is one means that may be used in an attempt to enrich for recipient cells prior to culturing (whether cultured on solid media or in suspension). The preferred cells may be those located at the surface of a cell cluster, and may further be identifiable by their lack of differentiation, their size and dense cytoplasm. The preferred cells will generally be those cells which are less differentiated, or not yet committed to differentiation. Thus, one may wish to identify and select those cells which are cytoplasmically dense, relatively unvacuolated with a high nucleus to cytoplasm ratio (e.g., determined by cytological observations), small in size (e.g., 10–20 $\mu$m), and capable of sustained divisions and somatic proembryo formation.

It is proposed that other means for identifying such cells also may be employed. For example, through the use of dyes, such as Evan's blue, which are excluded by cells with relatively non-permeable membranes, such as embryogenic cells, and taken up by relatively differentiated cells such as root-like cells and snake cells (so-called due to their snake-like appearance).

Other possible means of identifying recipient cells include the use of isozyme markers of embryogenic cells, such as glutamate dehydrogenase, which can be detected by cytochemical stains (Fransz et al., 1989). However, it is cautioned that the use of isozyme markers including glutamate dehydrogenase may lead to some degree of false positives from non-embryogenic cells such as rooty cells which nonetheless have a relatively high metabolic activity.

(i) Culturing Cells to be Recipients for Transformation

The ability to prepare and cryopreserve cultures of plant cells is important to certain aspects of the present invention, in that it provides a means for reproducibly and successfully preparing cells for transformation. A variety of different types of media have been previously developed and may be employed in carrying out various aspects of the invention. The following table, Table 7, sets forth the composition of the media preferred by the inventor for carrying out these aspects of the invention.

TABLE 7

Tissue Culture Media Which are Used for Type II Callus Development, Development of Suspension Cultures and Regeneration of Plant Cells (Particularly Maize Cells)

| MEDIA NO. | BASAL MEDIUM | SUCROSE | pH | OTHER COMPONENTS** (Amount/L) |
|---|---|---|---|---|
| 7 | MS* | 2% | 6.0 | .25 mg thiamine<br>.5 mg BAP<br>.5 mg NAA<br>Bactoagar |
| 10 | MS | 2% | 6.0 | .25 mg thiamine<br>1 mg BAP<br>1 mg 2,4-D<br>400 mg L-proline<br>Bactoagar |
| 19 | MS | 2% | 6.0 | .25 mg thiamine<br>.25 mg BAP<br>.25 mg NAA<br>Bactoagar |
| 20 | MS | 3% | 6.0 | .25 mg thiamine<br>1 mg BAP<br>1 mg NAA<br>Bactoagar |
| 52 | MS | 2% | 6.0 | .25 mg thiamine<br>1 mg 2,4-D<br>$10^{-7}$M ABA |
| 101 | MS | 3% | 6.0 | BACTOAGAR<br>MS vitamins<br>100 mg myo-inositol<br>Bactoagar |
| 105 | MS | — | 3.5 | 0.04 mg NAA<br>3 mg BAP<br>1 mg thiamine.HCl<br>0.5 mg niacin<br>0.91 mg L-asparagine monohydrate<br>100 mg myo-inositol<br>100 mg casein hydrolysate<br>1.4 g L-proline<br>20 g sorbitol<br>2.0 g Gelgro |
| 110 | MS | 6% | 5.8 | 1 mg thiamine.HCl<br>1 mg niacin<br>3.6 g Gelgro |
| 142 | MS | 6% | 6.0 | MS vitamins<br>5 mg BAP<br>0.186 mg NAA<br>0.175 mg IAA<br>0.403 mg 2IP<br>Bactoagar |
| 157 | MS | 6% | 6.0 | MS vitamins<br>100 mg myo-inositol<br>Bactoagar |
| 163 | MS | 3% | 6.0 | MS vitamins<br>3.3 mg dicamba<br>100 mg myo-inositol<br>Bactoagar |
| 171 | MS | 3% | 6.0 | MS vitamins<br>.25 mg 2,4-D<br>10 mg BAP<br>100 mg myo-inositol<br>Bactoagar |
| 173 | MS | 6% | 6.0 | MS vitamins<br>5 mg BAP<br>.186 mg NAA<br>.175 mg IAA<br>.403 mg 2IP<br>$10^{-7}$M ABA<br>200 mg myo-inositol<br>Bactoagar |
| 177 | MS | 3% | 6.0 | MS vitamins<br>.25 mg 2,4-D<br>10 mg BAP<br>$10^{-7}$M ABA<br>100 mg myo-inositol<br>Bactoagar |
| 185 | MS | — | 5.8 | 3 mg BAP<br>.04 mg NAA<br>RT vitamins<br>1.65 mg thiamine<br>1.38 g L-proline<br>20 g sorbitol<br>Bactoagar |
| 189 | MS | — | 5.8 | 3 mg BAP<br>.04 mg NAA<br>.5 mg niacin<br>800 mg L-asparagine<br>100 mg casamino acids<br>20 g sorbitol<br>1.4 g L-proline<br>100 mg myo-inositol<br>Gelgro |
| 201 | N6 | 2% | 5.8 | N6 vitamins<br>2 mg L-glycine<br>1 mg 2,4-D |

TABLE 7-continued

Tissue Culture Media Which are Used for Type II Callus Development, Development of Suspension Cultures and Regeneration of Plant Cells (Particularly Maize Cells)

| MEDIA NO. | BASAL MEDIUM | SUCROSE | pH | OTHER COMPONENTS** (Amount/L) |
|---|---|---|---|---|
| 205 | N6 | 2% | 5.8 | 100 mg casein hydrolysate<br>2.9 g L-proline<br>Gelgro<br>N6 vitamins<br>2 mg L-glycine<br>.5 mg 2,4-D<br>100 mg casein hydrolysate<br>2.9 g L-proline<br>Gelgro |
| 209 | N6 | 6% | 5.8 | N6 vitamins<br>2 mg L-glycine<br>100 mg casein hydrolysate<br>0.69 g L-proline<br>Bactoagar |
| 210 | N6 | 3% | 5.5 | N6 vitamins<br>2 mg 2,4-D<br>250 mg Ca pantothenate<br>100 mg myo-inositol<br>790 mg L-asparagine<br>100 mg casein hydrolysate<br>1.4 g L-proline<br>Hazelton agar**** <br>2 mg L-glycine |
| 211 | N6 | 2% | 5.8 | 1 mg 2,4-D<br>0.5 mg niacin<br>1.0 mg thiamine<br>0.91 g L-asparagine<br>100 mg myo-inositol<br>0.5 g MES<br>100 mg/L casein hydrolysate<br>1.6 g MgCl$_2$-6H$_2$O<br>0.69 g L-proline<br>2 g Gelgro |
| 212 | N6 | 3% | 5.5 | N6 vitamins<br>2 mg L-glycine<br>2 mg 2,4-D<br>250 mg Ca pantothenate<br>100 mg myo-inositol<br>100 mg casein hydrolysate<br>1.4 g L-proline<br>Hazelton agar**** |
| 227 | N6 | 2% | 5.8 | N6 vitamins<br>2 mg L-glycine<br>13.2 mg dicamba<br>100 mg casein hydrolysate<br>2.9 g L-proline<br>Gelgro |
| 273 (also, 201V, 236S, 201D, 2071, 2366, 201SV, 2377, and 201BV) | N6 | 2% | 5.8 | N6 vitamins<br>2 mg L-glycine<br>1 mg 2,4-D<br>16.9 mg AgNO$_3$<br>100 mg casein hydrolysate<br>2.9 g L-proline |
| 279 | N6 | 2% | 5.8 | 3.3 mg dicamba<br>1 mg thiamine<br>.5 mg niacin<br>800 mg L-asparagine<br>100 mg casein hydrolysate<br>100 mg myoinositol<br>1.4 g L-proline |
| 288 | N6 | 3% | | Gelgro****<br>3.3 mg dicamba<br>1 mg thiamine<br>.5 mg niacin<br>.8 g L-asparagine<br>100 mg myo-inositol<br>1.4 g L-proline<br>100 mg casein hydrolysate<br>16.9 mg AgNO$_3$<br>Gelgro |
| 401 | MS | 3% | 6.0 | 3.73 mg Na$_2$EDTA<br>.25 mg thiamine<br>1 mg 2,4-D<br>2 mg NAA<br>200 mg casein hydrolysate<br>500 mg K$_2$SO$_4$<br>400 mg KH$_2$PO$_4$<br>100 mg myo-inositol |
| 402 | MS | 3% | 6.0 | 3.73 mg Na$_2$EDTA<br>.25 mg thiamine<br>1 mg 2,4-D<br>200 mg casein hydrolysate<br>2.9 g L-proline<br>500 mg K$_2$SO$_4$<br>400 mg KH$_2$PO$_4$<br>100 mg myo-inositol |
| 409 | MS | 3% | 6.0 | 3.73 mg Na$_2$EDTA<br>.25 mg thiamine<br>9.9 mg dicamba<br>200 mg casein hydrolysate<br>2.9 g L-proline<br>500 mg K$_2$SO$_4$<br>400 mg KH$_2$PO$_4$<br>100 mg myo-inositol |
| 501 | Clark's Medium*** | 2% | 5.7 | |
| 607 | 1/2 × MS | 3% | 5.8 | 1 mg thiamine<br>1 mg niacin<br>Gelrite |
| 615 | MS | 3% | 6.0 | MS vitamins<br>6 mg BAP<br>100 mg myo-inositol<br>Bactoagar |
| 617 | 1/2 × MS | 1.5% | 6.0 | MS vitamins<br>50 mg myo-inositol<br>Bactoagar |
| 708 | N6 | 2% | 5.8 | N6 vitamins<br>2 mg L-glycine<br>1.5 mg 2,4-D<br>200 mg casein hydrolysate<br>0.69 g L-proline<br>Gelrite |
| 721 | N6 | 2% | 5.8 | 3.3 mg dicamba<br>1 mg thiamine<br>.5 mg niacin<br>800 mg L-asparagine<br>100 mg myo-inositol<br>100 mg casein hydrolysate<br>1.4 g L-proline<br>54.65 g mannitol<br>Gelgro |
| 726 | N6 | 3% | 5.8 | 3.3 mg dicamba<br>.5 mg niacin<br>1 mg thiamine<br>800 mg L-asparagine |

TABLE 7-continued

Tissue Culture Media Which are Used for Type II Callus Development, Development of Suspension Cultures and Regeneration of Plant Cells (Particularly Maize Cells)

| MEDIA NO. | BASAL MEDIUM | SUCROSE | pH | OTHER COMPONENTS** (Amount/L) |
|---|---|---|---|---|
| 727 | N6 | 3% | 5.8 | 100 mg myo-inositol<br>100 mg casein hydrolysate<br>1.4 g L-proline<br>N6 vitamins<br>2 mg L-glycine<br>9.9 mg dicamba<br>100 mg casein hydrolysate<br>2.9 g L-proline<br>Gelgro |
| 728 | N6 | 3% | 5.8 | N6 vitamins<br>2 mg L-glycine<br>9.9 mg dicamba<br>16.9 mg AgNO$_3$<br>100 mg casein hydrolysate<br>2.9 g L-proline<br>Gelgro |
| 734 | N6 | 2% | 5.8 | N6 vitamins<br>2 mg L-glycine<br>1.5 mg 2,4-D<br>14 g Fe sequestreene (replaces Fe-EDTA)<br>200 mg casein hydrolyste<br>0.69 g L-proline<br>Gelrite |
| 735 | N6 | 2% | 5.8 | 1 mg 2,4-D<br>.5 mg niacin<br>.91 g L-asparagine<br>100 mg myo-inositol<br>1 mg thiamine<br>.5 g MES<br>.75 g MgCl$_2$<br>100 mg casein hydrolysate<br>0.69 g L-proline<br>Gelgro |
| 2004 | N6 | 3% | 5.8 | 1 mg thiamine<br>0.5 mg niacin<br>3.3 mg dicamba<br>17 mg AgNO$_3$<br>1.4 g L-proline<br>0.8 g L-asparagine<br>100 mg casein hydrolysate<br>100 mg myo-inositol<br>Gelrite |
| 2008 | N6 | 3% | 5.8 | 1 mg thiamine<br>0.5 mg niacin<br>3.3 mg dicamba<br>1.4 g L-proline<br>0.8 g L-asparagine<br>Gelrite |

*Basic MS medium discribed in Murashige and Skoog (1962). This medium is typically modified by decreasing the NH$_4$NO$_3$ from 1.64 g/l to 1.55 g/l, and omitting the pyridoxine HCl, nicotinic acid, myo-inositol and glycine.
**NAA = Napthol Acetic Acid
IAA = Indole Acetic Acid
2-IP = 2, isopentyl adenine
2,4-D = 2,4-Dichlorophenoxyacetic Acid
BAP = 6-Benzyl aminopurine
ABA = abscisic acid
***Basic medium described in Clark (1982)
****These media may be made with or without solidifying agent.

A number of exemplary maize cultures which may be used for transformation have been developed and are disclosed in U.S. patent appl. Ser. No. 08/113,561, filed Aug. 25, 1993, which is specifically incorporated herein by reference.

(ii) Media

In certain embodiments of the current invention, recipient cells may be selected following growth in culture. Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the invention will have some similar components (see Table 7), but may differ in the composition and proportions of their ingredients depending on the particular application envisioned. For example, various cell types usually grow in more than one type of media, but will exhibit different growth rates and different morphologies, depending on the growth media. In some media, cells survive but do not divide.

Various types of media suitable for culture of plant cells previously have been described. Examples of these media include, but are not limited to, the N6 medium described by Chu et al. (1975) and MS media (Murashige and Skoog, 1962). It has been discovered that media such as MS which have a high ammonia/nitrate ratio are counterproductive to the generation of recipient cells in that they promote loss of morphogenic capacity. N6 media, on the other hand, has a somewhat lower ammonia/nitrate ratio, and is contemplated to promote the generation of recipient cells by maintaining cells in a proembryonic state capable of sustained divisions.

(iii) Maintenance

The method of maintenance of cell cultures may contribute to their utility as sources of recipient cells for transformation. Manual selection of cells for transfer to fresh culture medium, frequency of transfer to fresh culture medium, composition of culture medium, and environmental factors including, but not limited to, light quality and quantity and temperature are all important factors in maintaining callus and/or suspension cultures that are useful as sources of recipient cells. It is contemplated that alternating callus between different culture conditions may be beneficial in enriching for recipient cells within a culture. For example, it is proposed that cells may be cultured in suspension culture, but transferred to solid medium at regular intervals. After a period of growth on solid medium cells can be manually selected for return to liquid culture medium. It is proposed that by repeating this sequence of transfers to fresh culture medium it is possible to enrich for recipient cells. It also is contemplated that passing cell cultures through a 1.9 mm sieve is useful in maintaining the friability of a callus or suspension culture and may be beneficial in enriching for transformable cells.

(iv) Cryopreservation Methods

Cryopreservation is important because it allows one to maintain and preserve a known transformable cell culture for future use, while eliminating the cumulative detrimental effects associated with extended culture periods.

Cell suspensions and callus were cryopreserved using modifications of methods previously reported (Finkle, 1985; Withers & King, 1979). The cryopreservation protocol comprised adding a pre-cooled (0° C.) concentrated cryoprotectant mixture stepwise over a period of one to two hours to pre-cooled (0° C.) cells. The mixture was maintained at 0° C. throughout this period. The volume of added cryoprotectant was equal to the initial volume of the cell suspension (1:1 addition), and the final concentration of cryoprotectant additives was 10% dimethyl sulfoxide, 10% polyethylene glycol (6000 MW), 0.23M proline and 0.23M glucose. The mixture was allowed to equilibrate at 0° C. for 30 minutes, during which time the cell suspension/ cryoprotectant mixture was divided into 1.5 ml aliquot (0.5 ml packed cell volume) in 2 ml polyethylene cryo-vials. The tubes were cooled at 0.5° C./minute to −8° C. and held at this temperature for ice nucleation.

Once extracellular ice formation had been visually confirmed, the tubes were cooled at 0.5° C./minute from −8° C. to −35° C. They were held at this temperature for 45 minutes (to insure uniform freeze-induced dehydration throughout the cell clusters). At this point, the cells had lost the majority of their osmotic volume (i.e., there is little free water left in the cells), and they could be safely plunged into liquid nitrogen for storage. The paucity of free water remaining in the cells in conjunction with the rapid cooling rates from −35° C. to −196° C. prevented large organized ice crystals from forming in the cells. The cells are stored in liquid nitrogen, which effectively immobilizes the cells and slows metabolic processes to the point where long-term storage should not be detrimental.

Thawing of the extracellular solution was accomplished by removing the cryo-tube from liquid nitrogen and swirling it in sterile 42° C. water for approximately 2 minutes. The tube was removed from the heat immediately after the last ice crystals had melted to prevent heating the tissue. The cell suspension (still in the cryoprotectant mixture) was pipetted onto a filter, resting on a layer of BMS cells (the feeder layer which provided a nurse effect during recovery). The cryoprotectant solution is removed by pipetting. Culture medium comprised a callus proliferation medium with increased osmotic strength. Dilution of the cryoprotectant occurred slowly as the solutes diffused away through the filter and nutrients diffused upward to the recovering cells. Once subsequent growth of the thawed cells was noted, the growing tissue was transferred to fresh culture medium. If initiation of a suspension culture was desired, the cell clusters were transferred back into liquid suspension medium as soon as sufficient cell mass had been regained (usually within 1 to 2 weeks). Alternatively, cells were cultured on solid callus proliferation medium. After the culture was reestablished in liquid (within 1 to 2 additional weeks), it was used for transformation experiments. When desired, previously cryopreserved cultures may be frozen again for storage.

VIII. Production and Characterization of Stably Transformed Plants

After effecting delivery of exogenous DNA to recipient cells, the next steps generally concern identifying the transformed cells for further culturing and plant regeneration. As mentioned herein, in order to improve the ability to identify transformants, one may desire to employ a selectable or screenable marker gene as, or in addition to, the expressible gene of interest. In this case, one would then generally assay the potentially transformed cell population by exposing the cells to a selective agent or agents, or one would screen the cells for the desired marker gene trait.

(i) Selection

It is believed that DNA is introduced into only a small percentage of target cells in any one experiment. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by arninoglycoside phosphostransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA. Using the techniques disclosed herein, greater than 40% of bombarded embryos may yield transformants.

One herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus Streptomyces also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*. In the bacterial source organism, this enzyme acetylates the free amino group of PPT preventing auto-toxicity (Thompson et al., 1987). The bar gene has been cloned (Murakami et al., 1986; Thompson et al., 1987) and expressed in transgenic tobacco, tomato, potato (De Block et al., 1987) Brassica (De Block et al., 1989) and maize (U.S. Pat. No. 5,550,318). In previous reports, some transgenic plants which expressed the resistance gene were completely resistant to commercial formulations of PPT and bialaphos in greenhouses.

Another example of a herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103. The best characterized mutant EPSPS gene conferring glyphosate resistance comprises amino acid changes at residues 102 and 106, although it is anticipated that other mutations will also be useful (PCT/WO97/4103).

To use the bar-bialaphos or the EPSPS-glyphosate selective system, bombarded tissue is cultured for 0–28 days on nonselective medium and subsequently transferred to medium containing from 1–3 mg/l bialaphos or 1–3 mM glyphosate as appropriate. While ranges of 1–3 mg/l bialaphos or 1–3 mM glyphosate will typically be preferred, it is proposed that ranges of 0.1–50 mg/l bialaphos or 0.1–50 mM glyphosate will find utility in the practice of the invention. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

It further is contemplated that the herbicide DALAPON, 2,2-dichloropropionic acid, may be useful for identification of transformed cells. The enzyme 2,2-dichloropropionic acid dehalogenase (deh) inactivates the herbicidal activity of 2,2-dichloropropionic acid and therefore confers herbicidal resistance on cells or plants expressing a gene encoding the dehalogenase enzyme (Buchanan-Wollaston et al., 1992; U.S. patent appl. Ser. No. 08/113,561, filed Aug. 25, 1993; U.S. Pat. No. 5,508,468; and U.S. Pat. No. 5,508,468; each of the disclosures of which is specifically incorporated herein by reference in its entirety).

Alternatively, a gene encoding anthranilate synthase, which confers resistance to certain amino acid analogs, e.g., 5-methyltryptophan or 6-methyl anthranilate, may be useful as a selectable marker gene. The use of an anthranilate synthase gene as a selectable marker was described in U.S. Pat. No. 5,508,468; and U.S. patent application Ser. No. 08/604,789.

An example of a screenable marker trait is the red pigment produced under the control of the R-locus in maize. This pigment may be detected by culturing cells on a solid support containing nutrient media capable of supporting growth at this stage and selecting cells from colonies (visible aggregates of cells) that are pigmented. These cells may be cultured further, either in suspension or on solid media. The R-locus is useful for selection of transformants from bombarded immature embryos. In a similar fashion, the introduction of the C1 and B genes will result in pigmented cells and/or tissues.

The enzyme luciferase may be used as a screenable marker in the context of the present invention. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time. Another screenable marker which may be used in a similar fashion is the gene coding for green fluorescent protein.

It further is contemplated that combinations of screenable and selectable markers will be useful for identification of transformed cells. In some cell or tissue types a selection agent, such as bialaphos or glyphosate, may either not provide enough killing activity to clearly recognize transformed cells or may cause substantial nonselective inhibition of transformants and nontransformants alike, thus causing the selection technique to not be effective. It is proposed that selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. It is proposed that combinations of selection and screening may enable one to identify transformants in a wider variety of cell and tissue types. This may be efficiently achieved using a gene fusion between a selectable marker gene and a screenable marker gene, for example, between an NPTII gene and a GFP gene.

(ii) Regeneration and Seed Production

Cells that survive the exposure to the selective agent, or cells that have been scored positive in a screening assay, may be cultured in media that supports regeneration of plants. In an exemplary embodiment, MS and N6 media may be modified (see Table 7) by including further substances such as growth regulators. A preferred growth regulator for such purposes is dicamba or 2,4-D. However, other growth regulators may be employed, including NAA, NAA+ 2,4-D or perhaps even picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soiless plant growth mix, and hardened, e.g., in an environmentally controlled chamber at about 85% relative humidity, 600 ppm $CO_2$, and 25–250 microeinsteins $m^{-2} s^{-1}$ of light. Plants are preferably matured either in a growth chamber or greenhouse. Plants are regenerated from about 6 wk to 10 months after a transformant is identified, depending on the initial tissue. During regeneration, cells are grown on solid media in tissue culture vessels. Illustrative embodiments of such vessels are petri dishes and Plant Cons. Regenerating plants are preferably grown at about 19 to 28° C. After the regenerating plants have reached the stage of shoot and root development, they may be transferred to a greenhouse for further growth and testing.

Note, however, that seeds on transformed plants may occasionally require embryo rescue due to cessation of seed development and premature senescence of plants. To rescue developing embryos, they are excised from surface-disinfected seeds 10–20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with $10^{-5}$M abscisic acid and then transferred to growth regulator-free medium for germination.

Progeny may be recovered from transformed plants and tested for expression of the exogenous expressible gene by localized application of an appropriate substrate to plant parts such as leaves. In the case of bar transformed plants, it was found that transformed parental plants ($R_0$) and their progeny of any generation tested exhibited no bialaphos-related necrosis after localized application of the herbicide Basta to leaves, if there was functional PAT activity in the plants as assessed by an in vitro enzymatic assay. All PAT positive progeny tested contained bar, confirming that the presence of the enzyme and the resistance to bialaphos were associated with the transmission through the germline of the marker gene.

(iii) Characterization

To confirm the presence of the exogenous DNA or "transgene(s)" in the regenerating plants, a variety of assays may be performed. Such assays include, for example, "molecular biological" assays, such as Southern and Northern blotting and PCRT; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

1. DNA Integration, RNA Expression and Inheritance

Genomic DNA may be isolated from callus cell lines or any plant parts to determine the presence of the exogenous gene through the use of techniques well known to those skilled in the art. Note, that intact sequences will not always be present, presumably due to rearrangement or deletion of sequences in the cell.

The presence of DNA elements introduced through the methods of this invention may be determined by polymerase chain reaction (PCR™). Using this technique discreet fragments of DNA are amplified and detected by gel electrophoresis. This type of analysis permits one to determine whether a gene is present in a stable transformant, but does not prove integration of the introduced gene into the host cell genome It is the experience of the inventor, however, that DNA has been integrated into the genome of all transformants that demonstrate the presence of the gene through PCR™ analysis. In addition, it is not possible using PCR™ techniques to determine whether transformants have exogenous genes introduced into different sites in the genome, i.e., whether transformants are of independent origin. It is contemplated that using PCR™ techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, ie., confirm that the introduced gene has been integrated into the host cell genome. The technique of Southern hybridization provides information that is obtained using PCR™, e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR™, e.g., the presence of a gene.

Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot Northern hybridizations. These techniques are modifications of Northern blotting and will only demonstrate the presence or absence of an RNA species.

2. Gene Expression

While Southern blotting and PCR™ may be used to detect the gene(s) in question, they do not provide information as to whether the gene is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}$C-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

IX. Site Specific Integration or Excision of Transgenes

It is specifically contemplated by the inventors that one could employ techniques for the site-specific integration or excision of transformation constructs prepared in accordance with the instant invention. An advantage of site-specific integration or excision is that it can be used to overcome problems associated with conventional transformation techniques, in which transformation constructs typically randomly integrate into a host genome in multiple copies. This random insertion of introduced DNA into the genome of host cells can be lethal if the foreign DNA inserts into an essential gene. In addition, the expression of a transgene may be influenced by "position effects" caused by the surrounding genomic DNA. Further, because of difficulties associated with plants possessing multiple transgene copies, including gene silencing, recombination and unpredictable inheritance, it is typically desirable to control the copy number of the inserted DNA, often only desiring the insertion of a single copy of the DNA sequence.

Site-specific integration or excision of transgenes or parts of transgenes can be achieved in plants by means of homologous recombination (see, for example, U.S. Pat. No. 5,527, 695, specifically incorporated herein by reference in its entirety). Homologous recombination is a reaction between any pair of DNA sequences having a similar sequence of nucleotides, where the two sequences interact (recombine) to form a new recombinant DNA species. The frequency of homologous recombination increases as the length of the shared nucleotide DNA sequences increases, and is higher with linearized plasmid molecules than with circularized plasmid molecules. Homologous recombination can occur between two DNA sequences that are less than identical, but the recombination frequency declines as the divergence between the two sequences increases.

Introduced DNA sequences can be targeted via homologous recombination by linking a DNA molecule of interest to sequences sharing homology with endogenous sequences of the host cell. Once the DNA enters the cell, the two homologous sequences can interact to insert the introduced DNA at the site where the homologous genomic DNA sequences were located. Therefore, the choice of homologous sequences contained on the introduced DNA will determine the site where the introduced DNA is integrated via homologous recombination. For example, if the DNA sequence of interest is linked to DNA sequences sharing homology to a single copy gene of a host plant cell, the DNA sequence of interest will be inserted via homologous recombination at only that single specific site. However, if the DNA sequence of interest is linked to DNA sequences sharing homology to a multicopy gene of the host eukaryotic cell, then the DNA sequence of interest can be inserted via homologous recombination at each of the specific sites where a copy of the gene is located.

DNA can be inserted into the host genome by a homologous recombination reaction involving either a single reciprocal recombination (resulting in the insertion of the entire length of the introduced DNA) or through a double reciprocal recombination (resulting in the insertion of only the DNA located between the two recombination events). For example, if one wishes to insert a foreign gene into the genomic site where a selected gene is located, the introduced DNA should contain sequences homologous to the selected gene. A single homologous recombination event would then result in the entire introduced DNA sequence being inserted into the selected gene. Alternatively, a double recombination event can be achieved by flanking each end of the DNA sequence of interest (the sequence intended to be inserted into the genome) with DNA sequences homologous to the selected gene. A homologous recombination event involving each of the homologous flanking regions will result in the insertion of the foreign DNA. Thus only those DNA sequences located between the two regions sharing genomic homology become integrated into the genome.

Although introduced sequences can be targeted for insertion into a specific genomic site via homologous recombination, in higher eukaryotes homologous recombination is a relatively rare event compared to random insertion events. In plant cells, foreign DNA molecules find homologous sequences in the cell's genome and recombine at a frequency of approximately $0.5-4.2 \times 10^{-4}$. Thus any transformed cell that contains an introduced DNA sequence integrated via homologous recombination will also likely contain numerous copies of randomly integrated introduced DNA sequences. Therefore, to maintain control over the copy number and the location of the inserted DNA, these randomly inserted DNA sequences can be removed. One manner of removing these random insertions is to utilize a site-specific recombinase system. In general, a site specific recombinase system consists of three elements: two pairs of DNA sequence (the site-specific recombination sequences) and a specific enzyme (the site-specific recombinase). The site-specific recombinase will catalyze a recombination reaction only between two site-specific recombination sequences.

A number of different site specific recombinase systems could be employed in accordance with the instant invention, including, but not limited to, the Cre/lox system of bacteriophage P1 (U.S. Pat. No. 5,658,772, specifically incorporated herein by reference in its entirety), the FLP/FRT system of yeast (Golic and Lindquist, 1989), the Gin recombinase of phage Mu (Maeser et al., 1991), the Pin recombinase of E. coli (Enomoto et al., 1983), and the R/RS system of the pSR1 plasmid (Araki et al., 1992). The bacteriophage P1 Cre/lox and the yeast FLP/FRT systems constitute two particularly useful systems for site specific integration or excision of transgenes. In these systems a recombinase (Cre or FLP) will interact specifically with its respective site-specific recombination sequence (lox or FRT, respectively) to invert or excise the intervening sequences. The sequence for each of these two systems is relatively short (34 bp for lox and 47 bp for FRT) and therefore, convenient for use with transformation vectors.

The FLP/FRT recombinase system has been demonstrated to function efficiently in plant cells. Experiments on the performance of the FLP/FRT system in both maize and rice protoplasts indicate that FRT site structure, and amount of the FLP protein present, affects excision activity. In general, short incomplete FRT sites leads to higher accumulation of excision products than the complete full-length FRT sites. The systems can catalyze both intra- and intermolecular reactions in maize protoplasts, indicating its utility for DNA excision as well as integration reactions. The recombination reaction is reversible and this reversibility can compromise the efficiency of the reaction in each direction. Altering the structure of the site-specific recombination sequences is one approach to remedying this situation. The site-specific recombination sequence can be mutated in a manner that the product of the recombination reaction is no longer recognized as a substrate for the reverse reaction, thereby stabilizing the integration or excision event.

In the Cre-lox system, discovered in bacteriophage P1, recombination between loxP sites occurs in the presence of the Cre recombinase (see, e.g., U.S. Pat. No. 5,658,772, specifically incorporated herein by reference in its entirety). This system has been utilized to excise a gene located between two lox sites which had been introduced into a yeast genome (Sauer, 1987). Cre was expressed from an inducible yeast GAL1 promoter and this Cre gene was located on an autonomously replicating yeast vector.

Since the lox site is an asymmetrical nucleotide sequence, lox sites on the same DNA molecule can have the same or opposite orientation with respect to each other. Recombination between lox sites in the same orientation results in a deletion of the DNA Segment located between the two lox sites and a connection between the resulting ends of the original DNA molecule. The deleted DNA segment forms a circular molecule of DNA. The original DNA molecule and the resulting circular molecule each contain a single lox site. Recombination between lox sites in opposite orientations on the same DNA molecule result in an inversion of the nucleotide sequence of the DNA segment located between the two lox sites. In addition, reciprocal exchange of DNA segments proximate to lox sites located on two different DNA molecules can occur. All of these recombination events are catalyzed by the product of the Cre coding region.

X. Breeding Plants of the Invention

In addition to direct transformation of a particular genotype with a construct prepared according to the current invention, transgenic plants may be made by crossing a plant having a construct of the invention to a second plant lacking the construct. For example, a selected coding region operably linked to an RS81 promoter can be introduced into a particular plant variety by crossing, without the need for ever directly transforming a plant of that given variety. Therefore, the current invention not only encompasses a plant directly regenerated from cells which have been transformed in accordance with the current invention, but also the progeny of such plants. As used herein the term "progeny" denotes the offspring of any generation of a parent plant prepared in accordance with the instant invention, wherein the progeny comprises a construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:

(a) plant seeds of the first (starting line) and second (donor plant line that comprises a transgene of the invention) parent plants;

(b) grow the seeds of the first and second parent plants into plants that bear flowers;

(c) pollinate the female flower of the first parent plant with the pollen of the second parent plant; and (d) harvest seeds produced on the parent plant bearing the female flower.

Backcrossing is herein defined as the process including the steps of:

(a) crossing a plant of a first genotype containing a desired gene, DNA sequence or element to a plant of a second genotype lacking said desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring said desired gene, DNA sequence or element from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking said desired DNA sequence may be referred to as an unconverted genotype, line, inbred, or hybrid.

XI. Definitions

Genetic Transformation: A process of introducing a DNA sequence or construct (e.g., a vector or expression cassette) into a cell or protoplast in which that exogenous DNA is incorporated into a chromosome or is capable of autonomous replication.

Exogenous gene: A gene which is not normally present in a given host genome in the exogenous gene's present form In this respect, the gene itself may be native to the host genome, however, the exogenous gene will comprise the native gene altered by the addition or deletion of one or more different regulatory elements.

Expression: The combination of intracellular processes, including transcription and translation undergone by a coding DNA molecule such as a structural gene to produce a polypeptide.

Expression cassette: A chimeric DNA molecule which is designed for introduction into a host genome by genetic transformation. Preferred expression cassettes will comprise all of the genetic elements necessary to direct the expression of a selected gene. Expression cassettes prepared in accordance with the instant invention will include an RS81 promoter.

Expression vector: A vector comprising at least one expression cassette.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant.

Progeny: Any subsequent generation, including the seeds and plants therefrom, which is derived from a particular parental plant or set of parental plants.

Promoter: A recognition site on a DNA sequence or group of DNA sequences that provide an expression control element for a structural gene and to which RNA polymerase specifically binds and initiates RNA synthesis (transcription) of that gene.

$R_0$ Transgenic Plant: A plant which has been directly transformed with a selected DNA or has been regenerated from a cell or cell cluster which has been transformed with a selected DNA.

Regeneration: The process of growing a plant from a plant cell (e.g., plant protoplast, callus or explant).

Selected DNA: A DNA segment which one desires to introduce into a plant genome by genetic transformation.

Selected Gene: A gene which one desires to have expressed in a transgenic plant, plant cell or plant part. A selected gene may be native or foreign to a host genome, but where the selected gene is present in the host genome, will include one or more regulatory or functional elements which differ from native copies of the gene.

Transformation construct: A chimeric DNA molecule which is designed for introduction into a host genome by genetic transformation. Preferred transformation constructs will comprise all of the genetic elements necessary to direct the expression of one or more exogenous genes. Transformation constructs prepared in accordance with the instant invention will include an actin 2 intron and/or an actin 2 promoter. In particular embodiments of the instant invention, it may be desirable to introduce a transformation construct into a host cell in the form of an expression cassette.

Transformed cell: A cell the DNA complement of which has been altered by the introduction of an exogenous DNA molecule into that cell.

Transgene: A segment of DNA which has been incorporated into a host genome or is capable of autonomous replication in a host cell and is capable of causing the expression of one or more cellular products. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not originally present in a non-transgenic plant of the same strain. The transgenic plant may additionally contain sequences which are native to the plant being transformed, but wherein the "exogenous" gene has been altered in order to alter the level or pattern of expression of the gene.

Transit peptide: A polypeptide sequence which is capable of directing a polypeptide to a particular organelle or other location within a cell.

Vector: A DNA molecule capable of replication in a host cell and/or to which another DNA segment can be operatively linked so as to bring about replication of the attached segment. A plasmid is an exemplary vector.

XII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Useful expression of transgenes in maize is dependent on the promoter used. The number of effective promoters available for use with transgenes in maize is not abundant. New promoters, especially promoters that will express differentially in maize tissues, are spatially and/or temporally expressed or are induced to express by different environmental signals, would be useful. Such expression specific promoters could be useful in minimizing yield drag and other potential adverse physiological effects on maize growth and development that might be encountered by constitutive expression of a transgenic protein in a plant. For example, a corn rootworm resistance coding region under the control of a root-specific promoter and disease resistance coding regions under the control of a promoter induced by pathogen attack, would be especially useful. A wider range of effective promoters would also make it possible to introduce multiple transgenes into a plant, each fused to a different promoter, minimizing the risk of DNA sequence homology dependent transgene activation (co-suppression).

It is known that, often, expression of a transgene, fused to a plant promoter, does not achieve high levels of expression unless used in conjunction with an intron. Furthermore, not all promoter intron combinations are effective (Simpson and Flipowicz, 1996).

The inventors have demonstrated the functionality of a novel isolated promoter, preferably in conjunction with an intron in transgenic maize. Designated RS81, this promoter was isolated from a maize B73 genomic library and fused to the gus reporter gene, with and without a modified (internal deletion) rice Actin 2 intron 1. The RS81 promoter is the promoter of genes expressed in maize root tissue but not in kernel tissue and, in molecular analysis, was shown to have a root-specific expression profile. Transient expression assays in microparticle bombarded maize suspension cells and in excised maize root and leaf tissue, were carried out to determine the functionality of the promoter. The promoter was functionally active, when used in conjunction with a modified (internal deletion) rice Actin 2 intron 1. Furthermore, the RS81 promoter-intron combination achieved transient expression levels that are at least 56% the expression level of the strong Actin 1 promoter-Actin 1 intron combination (Zhang et al., 1991).

cDNAs that are expressed in maize line B73 root tissue, but not in kernel tissue, were isolated by differential Southern hybridization. Individual bacterial clones from a B73 root cDNA library, were bound to duplicate nitrocellulose membranes. One membrane was hybridized with 32P-labeled reverse transcribed B73 poly(A+)RNA from root tissue, and the second membrane hybridized with $^{32}$P-labeled reverse transcribed B73 poly(A+)RNA from kernel tissue. A cDNA that hybridized to root probe, but not to kernel probe were considered for further analysis.

Example 1

Cloning of the RS81 Promoter

The root positive, kernel negative cDNAs were further analyzed by Southern and Northern analysis. cDNA that remained of interest, was partially sequenced, and the sequence used the search Genbank for similar sequences. Promoter isolation was initiated for a cDNA that was considered proprietary, giving rise to RS81. The RS81 was fully sequenced and used to search Genbank. RS81 cDNA sequence (98.8% complete cDNA sequence) had 81% identity to a *Orysa saliva* root EST (dbj(D23748), 68% nucleotide identity to a *Hordeum vulgare* mRNA for y-TIP-like protein (emb(X80266) and 72% amino acid identity to a *Nicotiana tabacum* root specific tonoplast protein (sp (P30571).

A patent has been issued for the promoter of the RS81-like gene in tobacco (U.S. Pat. No. 5,459,252). The RS81 promoter from maize (2584 bp) has no significant identity to the tobacco promoter, however.

The root positive, kernel negative cDNAs were used to probe a lambda B73 genomic library. Putative clones were isolated through multiple rounds of screening until single clone purity was achieved. DNA from each of the lambda clones was characterize by restriction digest analysis and Southern blot comparison to the banding fingerprint of B73 genomic DNA. A lambda clone matching the genomic pattern was use for isolation of the sequence 5' of the cDNA start codon. An approximately 4000 bp SalI fragment was cloned into pUC 19. The structure of the RS81 5' region obtained is given in FIG. 1 and the corresponding nucleotide sequence is given in SEQ ID NO: 1.

translation start codon (Rac2=1435 bp). In order to determine the structure of the Act2 5' region, a search was carried out of the Rice Genome Project's EST database with Act2 5' sequences. This sequence similarity search identified a partial cDNA sequence from rice callus tissue (D15626) that contains sequences identical to the two transcribed but untranslated exons, exon 1 and exon 2, in the 5' region of the Act2 genomic clone. An alignment between the sequence of the Act2 5' region and the rice EST was used to determine the structure of the Act2 5' sequence. The 2635 bp sequence of the Act2 5' region was found to be composed of a promoter region of at least 740 bp, a 5' transcribed but untranslated first exon of at least 130 bp, a 5' intron of 1755 bp and the 14 bp transcribed but untranslated part of the second exon adjacent to the Act2 protein's translation initiation site (FIG. 3, SEQ ID NO:3). The 5' intron contains a ~300 bp mini transposable element (MITE) of the Tourist (C) type. The Act2 sequence in pUC-RAc2 contains 1.45 kb of Act2 5' sequence and starts just upstream of the potential Tourist element within the Act2 5' intron. The wild type, modified and maize consensus sequences are as given below, and in SEQ ID NO:6–SEQ ID NO: 11.

```
Wild-type Act2 5' intron splice junctions and start codon region
CTGCAGCCGCCATCCCCGGTTCTCTCCTCTTCTTTAG/gtgagcaa
PstI Modified Act 5' intron splice junction and start codon region:
CTGCAGCTGCCATCCCCGGTTCTCTCCTCTTCTTTAG/gtaaccaa
PstI PvuII                                BstEII Zea mays consensus intron splice junction:
                          AG/gtaagtnn Wild-type Act2 3' intron splice junctions and start codon region:
tttgtgttatgcag/ATCAGTTAAAATAAATGG Modified Act 3' intron splice junction and start codon region:
ttttttttttgcag/GTCGACTAGGTACCATGG
                SalI    KpnI  NcoI Zea mays consensus 3' intron splice junction and start codon region:
ttttttttttgcag/GT             ACAATGG
```

Example 2

Cloning of the Rice Actin 2 Intron

Two plasmid clones (pUC-RAc2 and pUC-RAc4) containing genomic DNA sequences of the rice actin 2 gene (Act2) were isolated as described in Reece et al., 1990. Restriction maps were generated for each clone, which consisted of an EcoRI restriction fragment from rice genomic DNA cloned in pUC13. The location of the region 5' of the translation start codon for in each of these clones was determined by comparing their restriction maps with those determined by sequence analysis of the pUC-Rac2 coding region (Reece et al., 1990). Restriction mapping and preliminary sequence analysis indicated that the pUC-Rac4 genomic clone was identical to, but 1.2 kb longer than, that of the pUC-Rac2 clone.

Sequence characterization was carried out to determine the length and structure of the 5' region in pUC-RAc2 and pUC-RAc4 by the dideoxy chain termination method using a Perkin-Elmer ABI377 automated sequencing machine. The sequence analysis of pUC-RAc4 revealed that the genomic clone contained a 2635 bp sequence 5' of the Act2

Sequence analysis of the cloned actin 2 intron sequence revealed a Tourist-like transposable element within the intron. In order to evaluate the effect of this repetitive element on the function of the actin 2 intron, a modified deletion derivative of the Act2 intron (ΔAct2int), that lacks the inverted repeat sequence associated with the Tourist-like transposable element was prepared (SEQ ID NO:5). A 4.3 kB EcoRI-XbaI restriction fragment, containing the Act2 promoter, exon 1, intron 1 and exon 2, was isolated from pUC-RAc4 and cloned into pBSII-SK(−) (Strategene) to create the vector pBS-5'RAc2. A 4.3 kB SalI-SacII restriction fragment, containing the Act2 promoter, exon 1, intron 1 and exon 2, was isolated from pBS-5'RAc2 and cloned into pGEM5Zf(+) (Promega) to create the vector pGEM-5'RAc2. PCR-mediated sequence mutagenesis was used to introduce KpnI and NcoI restriction sites around the gus translation initiation codon creating pGEM-PrAct2. pGEM-PrLAct2 was digested with BglII and BclI the intervening intron sequence, containing the Tourist mini-transposon-like inverted repeat, was excised, and the remaining sequence self-ligated to create pGEM-PrAct2Δi.

Example 3

Construction of RS81 Promoter-gus-nos, RS81 Promoter-Intron-gus-nos and RS81 Promoter-Intron-gus-nos Fusion Vectors Restriction enzyme analysis and Southern blot analysis of the lambda clone indicated that the RS81 promoter region was located on an approximately 4000 bp SalI gDNA fragment. The SalI fragment was cloned into pUC19. The bases around the ATG start of the coding region were PCR™ modified to an NcoI restriction site to accommodate fusing the promoter to the gus gene. The PCR™ fragment contains a HindIII site 5' of the NcoI site. The promoter was then fused to the gus gene in plasmid vector pUC19 in three steps. First, the PCR™ generated NcoI-HindIII 3' end of the promoter was ligated to the NcoI-HindIII site of the gus-nos terminator containing plasmid vector, pGN73. Second, the promoter region-gus-nos fragment was isolated as a HindIII-EcoRI fragment and ligated with the HindIII-PstI fragment (the mid promoter region) into the PstI-EcoRI site of plasmid vector pUC19. Lastly, the PstI—PstI 5' fragment of the promoter region was ligated into the PstI site of the construct and the correct orientation determined. To construct the RS81 promoter-intron-gus-nos fusion vector, the NcoI to NruI region (19 bp from the ATG start site) at the promoter 3' end was replaced with the Act2 Δ intron, as a NcoI-PvuII fragment. A RS81 promoter-Act2 Δ intron-gus-rbcS fusion vector also was constructed by cloning the RS81 promoter-Act2 Δ intron fragment into the gus-rbcS plasmid vector, pGR73. These constructs were then analyzed for expression profiles against constructs employing the actin 1 promoter in transient assays as described in Example 4 and Tables 8 and 9.

Example 4

Expression Analysis of Transformation Constructs in Transgenic Cells

Transient expression assays were performed as described by Jefferson (1987). Histochemical staining and fluorometric analysis for expression of the GUS reporter gene (*E coli* β-glucuronidase), fused to the RS81 promoter, was performed using 1×6 (716) callus suspension cells and excised maize root and leaf tissue. Equal molar concentrations of plasmid DNA were precipitated onto 0.6 micron gold particles and introduced into the tissues by microprojectile bombardment. For the histochemical staining, bombarded tissues were incubated for approximately 40 h at 24° C., followed by incubation in buffered solution containing 5-bromo-4-chloro-3-indolyl β-D-glucuronide (X-GLUC), overnight at 37° C. Comparison of expression levels from the RS81 promoter-reporter gene constructs, to levels from the Actin 1 promoter-Actin 1 intron-reporter gene construct, were visually assessed. For the fluorometric analysis, bombarded suspension callus cells were incubated for approximately 40 h at 24° C., then scraped off the filter paper supports and either stored at −70° C. or lysed immediately. 50 microliters of cell lysate was incubated in a total volume of 500 microliters reaction solution containing 4-methyl-umbelliferyl-b-D-glucuronide (MUG). The rate of the enzymatic conversion of MUG (substrate) to 4-methylumbelliferone 4-MU (product), was monitored at 20 min intervals for at least 1.5 h. Fifty microliter aliquots of the reaction mix were removed from the mix at the appropriate interval and the reaction stopped by addition to 0.95 milliliters of 0.2M $Na_2CO_3$. Fluorescence emitted from the samples was measured at emission 365 nm and excitation 455 nm. The readings were normalized for protein content using the Bradford assay and converted into nanomoles of 4-MU produced/μg protein/hour. The results of the assays are given in Tables 8 and 9.

TABLE 8

Promoter activity in transient assays of microparticle bombarded maize cells: in situ histochemical staining of gus reporter gene expression

| Pr. | Intron | Reporter Gene | 3' Term. | Relative GUS Activity in Suspension Culture Cells | Relative GUS Activity in Leaf Tissue | Relative GUS Activity in Root Tissue |
|---|---|---|---|---|---|---|
| — | — | gus | — | − | NA | NA |
| — | — | gus | nos | − | NA | NA |
| — | — | gus | rbcS | − | NA | NA |
| Act1 | Act1 | gus | — | + | NA | NA |
| Act1 | Act1 | gus | nos | +++ | +++ | +++ |
| Act1 | Act1 | gus | rbcS | ++ | NA | NA |
| RS81 | — | gus | nos | + | − | − |
| RS81 | Act2Δi | gus | nos | +++ | ++++ | +++ |
| RS81 | Act2Δi | gus | rbcS | ++++ | ++++ | ++++ |

NA = Not Assayed

TABLE 9

Promoter activity in transient assays of microparticle bombarded maize cells: quantitative fluorometric analysis of GUS specific activity

| Pr. | Intron | Reporter Gene | 3' Term. | Mean Gus Specific Activity (nM MUG/h/μg protein) | S.E. (n=2) |
|---|---|---|---|---|---|
| — | — | gus | — | 0.00 | 9.53 |
| — | — | gus | nos | 13.44 | 1.28 |
| — | — | gus | rbcS | 0.34 | 2.79 |
| Act1 | Act1 | gus | — | 115.05 | 5.79 |
| Act1 | Act1 | gus | nos | 843.77 | 1.97 |
| Act1 | Act1 | gus | rbcS | 304.63 | 8.34 |
| RS81 | — | gus | nos | 10.99 | 2.34 |
| RS81 | Act2Δi | gus | nos | 475.95 | 9.53 |
| RS81 | Act2Δi | gus | rbcS | 310.56 | 9.65 |

Example 5

Preparation of Microprojectiles

Microprojectiles were prepared by adding 60 mg of 0.6 μm gold particles (BioRad, cat. no. 165-2262) to 1000 μl absolute ethanol and incubating for at least 3 hours at room temperature followed by storage at −20° C. Twenty to thirty five μl of the sterile gold particles or more preferably 30 to 35 μl of gold particles (30 μl contains 1.8 mg of particles) were centrifuged in a microcentrifuge for up to 1 min. The supernatant was removed and one ml sterile water was added to the tube, followed by centrifugation at 1800–2000 rpm for 2–5 minutes. Microprojectile particles were resuspended in 30 μl of DNA solution containing about 500 ng of vector DNA.

Two hundred twenty microliters sterile water, 250 μl 2.5M $CaCl_2$ and 50 μl stock spermidine (14 μl spermidine in 986 μl water) were then added to the particle containing solution. The solution was then thoroughly mixed and placed on ice, followed by vortexing at 4° C. for 10 minutes and centrifugation at 500 rpm for 5 minutes The supernatant was removed and the pellet resuspended in 600 μl absolute ethanol. Following centrifugation at 500 rpm for 5 minutes, the pellet was resuspended in 36–38 μl of absolute ethanol, vortexed for approximately 20 seconds, and sonicated for 20–30 seconds. At this stage the particles were typically allowed to sit for 2–5 minutes, after which 5–10 µl of the supernatant was removed and dispensed on the surface of a flyer disk and the ethanol was allowed to dry completely. Alternatively, particles may be removed directly after resuspension and vortexing 20 to 30 seconds in 36 µl–38 µl of ethanol, placed on the flyer disk and allowed to dry as done for the settled treatment. The bombardment chamber was then evacuated to approximately 28 in. Hg prior to bombardment. The particles were then used for bombardment by a helium blast of approximately 1100 psi using the DuPont Biolistics PDS1000He particle bombardment device.

Example 6

Bombardment of Hi-II Immature Embryos

Immature embryos (1.2–3.0 mm in length) of the corn genotype Hi-II were excised from surface-sterilized, greenhouse-grown ears of Hi-II 10–12 days post-pollination. The Hi-II genotype was developed from an A188×B73 cross (Armstrong et al., 1991). Approximately 30 embryos per petri dish were plated axis side down on a modified N6 medium containing 1 mg/l 2,4-D, 100 mg/l casein hydrolysate, 2.9 g/L L-proline, 16.9 mg/L silver nitrate, 2 mg/L L-glycine, and 2% sucrose solidified with 2 g/l Gelgro, pH 5.8 (#201V medium). Embryos were cultured in the dark for two to six days at 24° C.

Approximately 3–4 hours prior to bombardment, embryos were transferred to the above culture medium with the sucrose concentration increased from 3% to 12%. When embryos were transferred to the high osmoticum medium they were arranged in concentric circles on the plate, starting 1 cm from the center of the dish, positioned such that their coleorhizal end was orientated toward the center of the dish. Usually two concentric circles were formed with 25–35 embryos per plate.

The plates containing embryos were placed on the third shelf from the bottom, 5 cm below the stopping screen. The 1100 psi rupture discs were used for bombardment. Each plate of embryos was bombarded once with the DuPont Biolistics PDS1000He particle gun. Following bombardment, embryos were allowed to recover on high osmoticum medium (#201SV, 12% sucrose) overnight (16–24 hours) and were then transferred to selection medium containing 1 mg/l bialaphos (plus I mg/l bialaphos). Embryos were maintained in the dark at 24° C. After three to four weeks on the initial selection plates about 90% of the embryos typically formed Type II callus and were transferred to selective medium containing 3 mg/l bialaphos (#201D). Southern or PCR analysis can then be used for analysis of transformants and assays of gene expression may be carried out.

Transformed callus is maintained on medium #204D. Regeneration of plants is initiated by transfer of callus to MS medium containing 0.04 mg/L NAA and 3 mg/L BAP (medium #105). Tissue is cultured in the dark for two weeks, followed by two weeks of culture on fresh medium #105 in low light. Tissue is subsequently transferred to MS medium with 6% sucrose without growth regulators (medium #110) and cultured in low light. Tissue is subcultured once in Petri dishes, followed by two subcultures on #110 medium in PHYTATRAYS. Regenerated plants are transferred from PHYTATRAYS to soil and grown further in a growth chamber or greenhouse. Tissue in PHYTATRAYS is grown under high light in a growth chamber.

Example 7

Transformation of H99 Immature Embryos or Callus and Selection with Paromomycin

Maize immature embryos (1.2–3.0 mm, 10–14 days post pollination) are isolated from greenhouse grown H99 plants that have been self or sib pollinated and are cultured on 735 medium in the dark at approximately 27° C. The immature embryos are either bombarded 1–6 days after isolation or cultured to produce embryogenic callus that is used for bombardment. Embryogenic callus is expanded and maintained by subculturing at 2–3 week intervals to fresh 735 medium. Prior to bombardment, cultured embryos or embryogenic callus (subdivided in approximately 2–4 mm clumps) are transferred to 735 medium containing 12% sucrose for 3–6 hours. Following bombardment, carried out as described in Example 6, tissue cultures are incubated overnight and transferred to 735 medium containing 500 mg/L paromomycin. After 2–3 weeks, callus is subdivided into small pieces (approximately 2–4 mm in diameter) and transferred to fresh selection medium. This subculture step is repeated at 2–3 week intervals for up to about 15 week post-bombardment, with subdivision and visual selection for healthy, growing callus.

Paromomycin tolerant callus is transferred to 735 medium without 2,4-D but containing 3.52 mg/L BAP for 3–9 days in the dark at approximately 27° C. and is subsequently transferred to 110 medium (½X MS salts, 0.5 mg/L thiamine, 0.5 mg/L nicotinic acid, 3% sucrose, 3.6 g/L Gelgro, pH 5.8) containing 100 mg/L paromomycin in Phytatrays (Sigma) and cultured at about 27° C. in the light. Plantlets that develop in Phytatrays after 3–6 weeks are then transferred to soil. Plantlets are acclimated in a growth chamber and grown to maturity in the greenhouse.

Example 8

Methods for Microprojectile Bombardment

Many variations in techniques for microprojectile bombardment are well known in the art and therefore deemed useful with the current invention. Exemplary procedures for bombardment are discussed in, for example, U.S. patent appl. Ser. No. 08/113,561, filed Aug. 25, 1993, specifically incorporated herein by reference in its entirety. Examples of target tissues which may be used with the current invention include immature embryos, Type I callus, Type II callus, Type III callus, suspension cultures and meristematic tissue (PCT Publication WO 96/04392). Some genotypes which are especially useful for maize transformation are specifically disclosed herein above, as well as in, for example, U.S. patent appl. Ser. No. 08/113,561, filed Aug. 25, 1993. Preferred genotypes will be those which are readily transformable and which also may be regenerated to yield a fertile transgenic plant.

Any method for acceleration of microprojectiles may potentially be used to transform a plant cell with the current invention. A preferred method will be a gas-driven particle gun such as the DuPont Biolistics PDS1000He particle bombardment device. Exemplary particles for bombardment include those comprised of tungsten, gold, platinum, and the like. Gold particles are deemed particularly useful in the current invention, with 0.6 µm or 0.7 µm gold particles being preferred and 0.6 µm particles most preferred. The most preferred particles will be DNA coated and have a mean size between 0.6 µm and 1.0 µm. Alternatively, particles may be allowed to settle for 2–5 minutes following precipitation of DNA onto particles. Particles are then removed from the supernatant and used for microprojectile bombardment. It is believed that the settling step enriches for a population of particles coated with DNA in which fewer aggregates of particles are present.

As disclosed herein, any DNA sequence may potentially be used for transformation. The DNA segments used for transformation will preferably include one or more selectable, secretable or screenable markers. Many examples of such are well known in the art and are specifically disclosed herein. In the case of selectable markers, selection may be in solid or liquid media. The DNA segments used will preferably also include one or more genes which confer, either individually or in combination with other sequences, a desired phenotype on the transformed plant. Exemplary genes for transformation and the corresponding phenotypes these sequences may confer on the transformed plant are disclosed herein.

Example 9

Expression Profile Analysis of the RS81 Promoter in Stably Transformed Plants

Expression cassettes comprising the RS81 promoter-Act2Δintron-GUS-nos (plasmid vector pDPG894) and RS81 promoter-Act2Δintron-GUS-rbcS (pDPG895) were introduced separately into HiII immature embryos as described in Examples 5 and 6. Each plasmid was bombarded into HiII immature embryos in conjunction with pDPG16, comprising a 35S promoter-bar-Tr7 expression cassette. Transformants were selected as described in Example 6. Expression of the GUS gene was assayed as described in Example 4 and Jefferson (1987).

Three of twenty-one transformants that were tested, comprising the RS81 promoter-Act2Δintron-GUS-rbcS expression cassette, expressed the GUS gene in callus. Plants were regenerated from each of the RS81 promoter- Act2Δintron-GUS-rbcS transformants. Root and leaf material were collected from plantlets grown in vitro at two times during regeneration. Plantlets were first assayed during the second month of plant regeneration. Plantlets from nine of the fifteen transformants expressed the GUS gene in roots, and five transformants that expressed GUS in roots also expressed GUS in the regenerating stem and leaf material. Plantlets also were assayed during the third month of plant regeneration, close to the time of transfer of plantlets to soil. GUS expressed in roots of twelve of eighteen transformants that were assayed. Furthermore, eight of the twelve plantlets that expressed GUS in roots also expressed GUS in stem and leaf material. An additional two plantlets expressed GUS in stem and leaf material, but did not express GUS in roots. GUS expression was observed in roots or $R_0$ plants growing in soil in the greenhouse that were regenerated from fourteen transformants. GUS expression was further assayed in seed harvested from $R_0$ plants derived from four transformants. In three transformants, GUS expression was observed in the seed.

One transformant, of eighteen assayed, that comprised the RS8 1 promoter- Act2Δintron-GUS-nos expression cassette, expressed the GUS gene in callus. Plants were regenerated from thirteen transformants. Root and leaf material were collected from regenerating plantlets grown in vitro and two times during regeneration. Plantlets, assayed during the second month of plant regeneration, from ten of the fourteen transformants, expressed GUS in roots. Only two transformants comprising the RS8 1 promoter and the nos terminator expressed GUS in roots and in regenerating shoot and leaf material. This observation suggests that the terminator sequence, e.g., rbcS, may influence the tissue specificity of gene expression. Plantlets assayed during the third month of regeneration, close to the time of transfer of plantlets to soil, expressed GUS in roots of five or six transformants assayed. Three of the five root expressing transformants also expressed GUS in stem and leaf material. Plants from fifteen transformants were transferred to soil in the greenhouse.

Example 10

Histological Analysis of the RS81 Promoter in Stably Transformed Plants

Immature embryos of the Hill genotype were bombarded and plants regenerated as described in Example 6 with a vector comprising the bar gene (pDPG165) and a second vector comprising the RS81 promoter operably linked to exon 1 of the rice actin 2 gene, the intron 1 of the rice actin 2 gene, the uidA gene encoding beta-glucuronidase and the 3' region derived from the *Agrobacterium tumefaciens* nopaline synthase gene (pDPG894). Root tissue was harvested from a greenhouse grown $R_0$ plant regenerated from a transformant designated II072SZ51202. Expression of the GUS gene was assayed as described in Example 4 and Jefferson (1987). Tissue samples were incubated in the GUS assay mix overnight at 37° C. Tissue was then transferred to FAA fixative (4% formalin, 5% acetic acid, 50% ethanol) at 0° C. The FAA was removed and replaced with fresh cold FAA, followed by incubation of the tissues at 4° C. overnight. FAA was replaced by 50% ethanol followed by dehydration by sequential transfer to 70%, 85%, 90% and twice in 100% ethanol. Tissue samples were infiltrated with Histoclear (National Diagnostics) by incubation in 1:1 ethanol:Histoclear followed by 3:1 Histoclear:ethanol, and twice in Histoclear. Molten Paraplast X-Tra (Oxford Labware) embedding wax was added. After two wax changes, tissue was embedded, trimmed and mounted for sectioning. Forty micron sections were cut on a Reichert-Jung rotary microtome and fixed to ProbeOn plus slides (Fisher Scientific). Sections were deparafinized in Histoclear and mounted directly or counterstained with Safranin O (in 70% ethanol) for 15 minutes, followed by Histoclear. Slides were sealed with HistoResin (Fisher Scientific) and visualized using 50× bright field optics on a Zeiss Axiophot (Germany) model EL-Einsatz 451888 microscope. Images were captured on Kodak Ektachrome 160 Tungsten film. The results of this study, as seen in FIG. 4, revealed expression of GUS directed by the RS81 promoter in the root endodermis surrounding the vascular bundles. This pattern of expression is consistent with RS81 being a promoter of a gene involved in water movement. Also, the coding sequence of the RS81 gene has homology to *Hordeum vulgare* and *N. tabacum* genes for tonoplast intrinsic proteins, which are aquaporin-like proteins involved in water movement within the plant.

Example 11

Introgression of Transgenes Into Elite Inbreds and Hybrids

Backcrossing can be used to improve a starting plant. Backcrossing transfers a specific desirable trait from one source to an inbred or other plant that lacks that trait. This can be accomplished, for example, by first crossing a superior inbred (A) (recurrent parent) to a donor inbred (non-recurrent parent), which carries the appropriate gene(s) for the trait in question, for example, a construct prepared in accordance with the current invention. The progeny of this cross first are selected in the resultant progeny for the desired trait to be transferred from the non-recurrent parent, then the selected progeny are mated back to the superior recurrent parent (A). After five or more backcross generations with selection for the desired trait, the progeny are hemizygous for loci controlling the characteristic being transferred, but are like the superior parent for most or almost all other genes. The last backcross generation would be selfed to give progeny which are pure breeding for the gene(s) being transferred, i.e. one or more transformation events.

Therefore, through a series a breeding manipulations, a selected transgene may be moved from one line into an entirely different line without the need for further recombinant manipulation. Transgenes are valuable in that they typically behave genetically as any other gene and can be manipulated by breeding techniques in a manner identical to any other corn gene. Therefore, one may produce inbred plants which are true breeding for one or more transgenes. By crossing different inbred plants, one may produce a large number of different hybrids with different combinations of transgenes. In this way, plants may be produced which have the desirable agronomic properties frequently associated with hybrids ("hybrid vigor"), as well as the desirable characteristics imparted by one or more transgene(s).

Example 12

Marker Assisted Selection

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

In the process of marker assisted breeding, DNA sequences are used to follow desirable agronomic traits (Tanksley et al., 1989) in the process of plant breeding. Marker assisted breeding may be undertaken as follows. Seed of plants with the desired trait are planted in soil in the greenhouse or in the field. Leaf tissue is harvested from the plant for preparation of DNA at any point in growth at which approximately one gram of leaf tissue can be removed from the plant without compromising the viability of the plant. Genomic DNA is isolated using a procedure modified from Shure et al. (1983). Approximately one gram of leaf tissue from a seedling is lypholyzed overnight in 15 ml polypropylene tubes. Freeze-dried tissue is ground to a powder in the tube using a glass rod. Powdered tissue is mixed thoroughly with 3 ml extraction buffer (7.0 urea, 0.35M NaCl, 0.05M Tris-HCl pH 8.0, 0.01M EDTA, 1% sarcosine). Tissue/buffer homogenate is extracted with 3 ml phenol/chloroform. The aqueous phase is separated by centrifugation, and precipitated twice using $\frac{1}{10}$ volume of 4.4M ammonium acetate pH 5.2, and an equal volume of isopropanol. The precipitate is washed with 75% ethanol and resuspended in 100–500 µl TE (0.01M Tris-HCl, 0.001M EDTA, pH 8.0).

Genomic DNA is then digested with a 3-fold excess of restriction enzymes, electrophoresed through 0.8% agarose (FMC), and transferred (Southern, 1975) to Nytran (Schleicher and Schuell) using 10×SCP (20 SCP: 2M NaCl, 0.6M disodium phosphate, 0.02M disodium EDTA). The filters are prehybridized in 6×SCP, 10% dextran sulfate, 2% sarcosine, and 500 µg/ml denatured salmon sperm DNA and $^{32}$P-labeled probe generated by random priming (Feinberg & Vogelstein, 1983). Hybridized filters are washed in 2×SCP, 1% SDS at 65° C. for 30 minutes and visualized by autoradiography using Kodak XAR5 film. Genetic polymorphisms which are genetically linked to traits of interest are thereby used to predict the presence or absence of the traits of interest.

Those of skill in the art will recognize that there are many different ways to isolate DNA from plant tissues and that there are many different protocols for Southern hybridization that will produce identical results. Those of skill in the art will recognize that a Southern blot can be stripped of radioactive probe following autoradiography and re-probed with a different probe. In this manner one may identify each of the various transgenes that are present in the plant. Further, one of skill in the art will recognize that any type of genetic marker which is polymorphic at the region(s) of interest may be used for the purpose of identifying the relative presence or absence of a trait, and that such information may be used for marker assisted breeding.

Each lane of a Southern blot represents DNA isolated from one plant. Through the use of multiplicity of gene integration events as probes on the same genomic DNA blot, the integration event composition of each plant may be determined. Correlations may be established between the contributions of particular integration events to the phenotype of the plant. Only those plants that contain a desired combination of integration events may be advanced to maturity and used for pollination. DNA probes corresponding to particular transgene integration events are useful markers during the course of plant breeding to identify and combine particular integration events without having to grow the plants and assay the plants for agronomic performance.

It is expected that one or more restriction enzymes will be used to digest genomic DNA, either singly or in combinations. One of skill in the art will recognize that many different restriction enzymes will be useful and the choice of restriction enzyme will depend on the DNA sequence of the transgene integration event that is used as a probe and the DNA sequences in the genome surrounding the transgene. For a probe, one will want to use DNA or RNA sequences which will hybridize to the DNA used for transformation. One will select a restriction enzyme that produces a DNA fragment following hybridization that is identifiable as the transgene integration event. Thus, particularly useful restriction enzymes will be those which reveal polymorphisms that are genetically linked to specific transgenes or traits of interest.

Example 13

General Methods for Assays

DNA analysis of transformed plants is performed as follows. Genomic DNA is isolated using a procedure modified from Shure et al., 1983. Approximately 1 gm callus or leaf tissue is ground to a fine powder in liquid nitrogen using a mortar and pestle. Powdered tissue is mixed thoroughly with 4 ml extraction buffer (7.0M urea, 0.35M NaCl, 0.05M Tris-HCl pH 8.0, 0.01M EDTA, 1% sarcosine). Tissue/buffer homogenate is extracted with 4 ml phenol/ chloroform. The aqueous phase is separated by centrifugation, passed through Miracloth, and precipitated twice using 1/10 volume of 4.4M ammonium acetate, pH 5.2 and an equal volume of isopropanol. The precipitate is washed with 70% ethanol and resuspended in 200–500 μl TE (0.01M Tris-HCl, 0.001M EDTA, pH 8.0).

The presence of a DNA sequence in a transformed cell may be detected through the use of polymerase chain reaction (PCR). Using this technique specific fragments of DNA can be amplified and detected following agarose gel electrophoresis. For example, two hundred to 1000 ng genomic DNA is added to a reaction mix containing 10 mM Tris-HCl pH 8.3, 1.5 mM $MgCl_2$, 50 mM KCl, 0.1 mg/ml gelatin, 200 μM each dATP, dCTP, dGTP, dTTP, 0.5 μM each forward and reverse DNA primers, 20% glycerol, and 2.5 units Taq DNA polymerase. The reaction is run in a thermal cycling machine as follows: 3 minutes at 94° C., 39 repeats of the cycle 1 minute at 94° C., 1 minute at 50° C., 30 seconds at 72° C., followed by 5 minutes at 72° C. Twenty μl of each reaction mix is run on a 3.5% NuSieve gel in TBE buffer (90 mM Tris-borate, 2 mM EDTA) at 50V for two to four hours. Using this procedure, for example, one may detect the presence of the bar gene, using the forward primer CATCGAGACAAGCACGGTCAACTTC (SEQ ID NO:12) and the reverse primer AAGTCCCTGGAGGCA-CAGGGCTTCAAGA (SEQ ID NO: 13). Primers for the Act2 intron or RS81 promoter can be readily prepared by one of skill in the art in light of the sequences given in SEQ ID NO:3 and SEQ ID NO: 1, respectively.

A method to detect the presence of phosphinothricin acetyl transferase (PAT) involves the use of an in vitro enzyme reaction followed by thin layer chromatography, as described in U.S. patent appl. Ser. No. 08/113,561, filed Aug. 25, 1993 (specifically incorporated herein by reference in its entirety). The procedure is conducted by preparing various protein extracts from homogenates of potentially transformed cells, and from control cells that have neither been transformed nor exposed to bialaphos selection, and then assaying by incubation with PPT and $^{14}$C-Acetyl Coenzyme A followed by thin layer chromatography. The results of this assay provide confirmation of the expression of the bar gene which codes for phosphinothricin acetyl transferase (PAT).

For Southern blot analysis genomic DNA is digested with a 3-fold excess of restriction enzymes, electrophoresed through 0.8% agarose (FMC), and transferred (Southern, 1975) to Nytran (Schleicher and Schuell) using 10×SCP (20×SCP: 2M NaCl, 0.6M disodium phosphate, 0.02M disodium EDTA). Probes are labeled with $^{32}$P using the random priming method (Boehringer Mannheim) and purified using Quik-Sep® spin columns (Isolab Inc., Akron, Ohio). Filters are prehybridized at 65° C. in 6×SCP, 10% dextran sulfate, 2% sarcosine, and 500 μg/ml heparin (Chomet et al., 1987) for 15 min. Filters then are hybridized overnight at 65° C. in 6×SCP containing 100 μg/ml denatured salmon sperm DNA and $^{32}$P-labeled probe. Filters are washed in 2×SCP, 1% SDS at 65° C. for 30 min. and visualized by autoradiography using Kodak XAR5 film. For rehybridization, the filters are boiled for 10 min. in distilled $H_2O$ to remove the first probe and then prehybridized as described above.

Example 14

Utilization of Transgenic Crops

The ultimate goal in plant transformation is to produce plants which are useful to man. In this respect, transgenic plants created in accordance with the current invention may be used for virtually any purpose deemed of value to the grower or to the consumer. For example, one may wish to harvest seed from transgenic plants. This seed may in turn be used for a wide variety of purposes. The seed may be sold to farmers for planting in the field or may be directly used as food, either for animals or humans. Alternatively, products may be made from the seed itself. Examples of products which may be made from the seed include, oil, starch, animal or human food, pharmaceuticals, and various industrial products. The food uses of maize, in addition to human consumption of maize kernels, include both products of dry- and wet-milling industries. The principal products of maize dry milling are grits, meal and flour. The maize wet-milling industry can provide maize starch, maize syrups, and dextrose for food use. Maize oil is recovered from maize germ, which is a by-product of both dry- and wet-milling industries.

Maize, including both grain and non-grain portions of the plant, also is used extensively as livestock feed, primarily for beef cattle, dairy cattle, hogs, and poultry. Industrial uses of maize include production of ethanol, maize starch in the wet-milling industry and maize flour in the dry-milling industry. The industrial applications of maize starch and flour are based on functional properties, such as viscosity, film formation, adhesive properties, and ability to suspend particles. The maize starch and flour have application in the paper and textile industries. Other industrial uses include applications in adhesives, building materials, foundry binders, laundry starches, explosives, oil-well muds, and other mining applications. Plant parts other than the grain of maize also are used in industry, for example, stalks and husks are made into paper and wallboard and cobs are used for fuel and to make charcoal. Other means for utilizing plants, such as those that may be made with the current invention, have been well known since the dawn of agriculture and will be known to those of skill in the art in light of the instant disclosure. Specific methods for crop utilization may be found in, for example, Sprague and Dudley (1988), and Watson and Ramstad (1987).

REFERENCES

The references listed below are incorporated herein by reference to the extent that they supplement, explain, provide a background for, or teach methodology, techniques, and/or compositions employed herein.

Abdullah et al., *Biotechnology*, 4:1087, 1986.
Abel et al., *Science*, 232:738–743, 1986.
Araki et al., *J. Mol Biol.* 225(1):25–37, 1992.
Armaleo et al., *Curr. Genet.* 17(2):97–103, 1990.
Armstrong et al., *Maize Genetics Coop Newsletter*, 65:92–93, 1991.
Bansal et al., *Proc. Nat'l Acad. Sci. USA*, 89:3654–3658, 1992.
Barkai-Golan et al., *Arch. Microbiol.*, 116:119–124, 1978.
Bates, *Mol. Biotechnol.*, 2(2):135–145, 1994.
Battraw and Hall, *Theor. App. Genet.*, 82(2):161–168, 1991.
Belanger and Kriz, *Genet.*, 129:863–872, 1991.
Bellus, *J. Macromol. Sci. Pure Appl. Chem.*, 1(l):1355–1376, 1994.
Bernal-Lugo and Leopold, *Plant Physiol.*, 98:1207–1210, 1992.
Berzal-Herranz el al., *Genes and Devel.*, 6:129–134, 1992.
Bevan et al., *Nucleic Acids Research*, 11(2):369–385, 1983.
Bhattacharjee; An; Gupta, *J. Plant Bioch. and Biotech.* 6,(2):69–73. 1997.
Blackman et al., *Plant Physiol.*, 100:225–230, 1992.

Bol et al., *Annu. Rev. Phytopath.,* 28:113–138, 1990.
Bouchez et al., *EMBO Journal,* 8(13):4197–4204, 1989.
Bower et al., *The Plant Journal,* 2:409–416. 1992.
Bowler et al., *Ann Rev. Plant Physiol.,* 43:83–116, 1992.
Branson and Guss, *Proceedings North Central Branch Entomological Society of America,* 27:91–95, 1972.
Broakaert et al., *Science,* 245:1100–1102, 1989.
Buchanan-Wollaston et al., *Plant Cell Reports* 1 1:627–631. 1992
Buising and Benbow, *Mol Gen Genet,* 243(1):71–81. 1994.
Callis, Fromm, Walbot, *Genes Dev.,* 1 :1183–1200, 1987.
Campbell (ed.), In: *Avermectin and Abamectin,* 1989.
Capaldi et al., *Biochem. Biophys. Res. Comm.,* 76:425, 1977.
Casa et al., *Proc. Nat'l Acad. Sci. USA,* 90(23):11212–11216, 1993.
Cashmore et al., *Gen. Eng. of Plants,* Plenum Press, New York, 29–38, 1983.
Cech et al., *Cell,* 27:487–496, 1981.
Chandler et al., *The Plant Cell,* 1:1175–1183, 1989.
Chau et al., *Science,* 244:174–181, 1989.
Chomet et al., *EMBO J.,* 6:295–302, 1987.
Chowrira et al., *J. Biol Chem.,* 269:25856–25864, 1994.
Christou; Murphy; Swain, *Proc. Nat'l Acad Sci. USA,* 84(12):3962–3966, 1987.
Chu et al., *Scientia Sinica,* 18:659–668, 1975.
Coe et al., In: *Corn and Corn Improvement,* 81–258, 1988.
Conkling et al., *Plant Physiol.,* 93:1203–1211, 1990.
Cordero, Raventos, San Segundo, *Plant J.,* 6(2)141–150, 1994.
Coxson et al., *Biotropica,* 24:121–133, 1992.
Cretin and Puigdomenech, *Plant Mol Biol.* 15(5):783–785, 1990
Cuozzo et al., *Bio/Technology,* 6:549–553, 1988.
Cutler et al., *J. Plant Physiol.,* 135:351–354, 1989.
Czapla and Lang, *J. Econ. Entomol.,* 83:2480–2485, 1990.
Davies et al., *Plant Physiol.,* 93:588–595, 1990.
De Block et al., *The EMBO Journal,* 6(9):2513–2518, 1987.
De Block, De Brouwer, Tenning, *Plant Physiol.,* 91:694–701, 1989.
Dellaporta et al., In: *Chromosome Structure and Function: Impact of New Concepts, 18th Stadler Genetics Symposium,* 11:263–282, 1988.
Dennis et al., *Nucl. Acids Res.,* 12(9):3983–4000, 1984.
Depicker et al., *Plant Cell Reports,* 7:63–66, 1988.
D'Halluin et al., *Plant Cell,* 4(12):1495–1505, 1992.
Didierjean et al., *Plant Mol Biol* 18(4):847–849, 1992.
Dure et al., *Plant Molecular Biology,* 12:475–486, 1989.
Ebert et al., 84:5745–5749, *Proc. Nat'l Acad. Sci. USA,* 1987
Ellis et al., *EMBO Journal,* 6(11):3203–3208, 1987.
Enomoto, et al., *J. Bacteriol.,* 6(2):663–668, 1983.
Erdmann et al., *Mol. Jour. Gen. Micro.,* 138:363–368, 1992.
Feinberg and Vogelstein, *Anal. Biochem.,* 132:6–13, 1983.
Finkle et al., *Plant Sci.,* 42:133–140, 1985.
Fitzpatrick, *Gen. Engineering News,* 22:7, 1993.
Forster and Symons, *Cell,* 49:211–220, 1987.
Fraley et al., *Bio/Technology,* 3:629–635, 1985.
Franken etal., *EMBO J.,* 10(9):2605–2612, 1991.
Fransz, de Ruijter, Schel, *Plant Cell Reports,* 8:67–70, 1989.
Fromm et al., *Nature,* 312:791–793, 1986.
Gallie et al., *The Plant Cell,* 1:301–311, 1989.
Gatehouse et al., *J. Sci. Food. Agric.,* 35:373–380, 1984.
Gelvin et al., In: *Plant Molecular Biology Manual.,* 1990.
Gerlach et al., *Nature* 328:802–805, 1987.
Ghosh-Biswas, Iglesias, Datta, Potrykus, *J. Biotechnol.,* 32(1):1–10, 1994.
Golic and Lindquist, *Cell,* 59:3, 499–509. 1989.
Gomez et al., *Nature,* 334:262–263, 1988.

Goring et al., *Proc. Nat'l Acad. Sci. USA,* 88:1770–1774, 1991.
Guerrero et al., *Plant Molecular Biology,* 15:11–26, 1990.
Gupta et al., *Proc. Nat'l Acad Sci. USA,* 90:1629–1633, 1993.
Hagio, Blowers, Earle, *Plant Cell Rep.,* 10(5):260–264, 1991.
Hamilton et al., *Proc. Nat'l Acad. Sci. USA,* 93(18):9975–9979, 1996.
Hammock et al., *Nature,* 344:458–461, 1990.
Haseloff and Gerlach, *Nature,* 334:585–591, 1988.
Haseloff et al., *Proc. Nat'l Acad. Sci. USA* 94(6):2122–2127, 1997.
He et al., *Plant Cell Reports,* 14 (2–3):192–196, 1994.
Hemenway et al., *The EMBO J.,* 7:1273–1280, 1988.
Hensgens et al., *Plant Mol. Biol.,* 22(6):1101–1127, 1993.
Hiei et al., *Plant. Mol. Biol.,* 35(1–2):205–218, 1997.
Hilder et al., *Nature,* 330:160–163, 1987.
Hinchee et al., *Bio/technol.,* 6:915–922, 1988.
Hou and Lin, *Plant Physiology,* 111:166, 1996.
Hudspeth and Grula, *Plant Mol. Biol.,* 12:579–589, 1989.
Ishida et al., *Nat. Biotechnol.,* 14(6):745–750, 1996.
Ikeda et al., *J. Bacteriol.,* 169:5615–5621, 1987.
Ikuta et al., *Bio/technol.,* 8:241–242, 1990.
Jefferson R. A., *Plant Mol. Biol. Rep.,* 5:387–405, 1987.
Johnson et al., *Proc. Nat'l Acad. Sci. USA,* 86:9871–9875, 1989.
Joshi, *Nucleic Acids Res.,* 15:6643–6653, 1987.
Joyce, *Nature,* 338:217–244, 1989.
Kaasen et al., *J. Bacteriology,* 174:889–898, 1992.
Kaeppler et al., *Plant Cell Reports* 9: 415–418, 1990.
Kaeppler, Somers, Rines, Cockburn, *Theor. Appl. Genet.,* 84(5–6):560–566, 1992.
Karsten et al., *Botanica Marina,* 35:11 –19, 1992.
Katz et al., *J. Gen. Microbiol.,* 129:2703–2714, 1983.
Keller et al., *EMBO J.,* 8(5):1309–1314, 1989.
Kim and Cech, *Proc. Nat'l Acad. Sci. USA,* 84:8788–8792, 1987.
Klee, Yanofsky, Nester, *Bio-Technology,* 3(7):637–642, 1985.
Knittel, Gruber; Hahne; Lenee, *Plant Cell Reports,* 14(2–3):81–86, 1994.
Kohler et al., *Plant Mol. Biol.,* 29(6): 1293–1298, 1995.
Koster and Leopold, *Plant Physiol.,* 88:829–832, 1988.
Kriz, Boston, Larkins, *Mol. Gen. Genet.,* 207(1):90–98, 1987.
Kunkel et al., *Methods Enzymol,* 154:367–382, 1987.
Langridge and Feix, *Cell,* 34:1015–1022, 1983.
Langridge et al., *Proc. Nat'l Acad. Sci. USA,* 86:3219–3223, 1989.
Laufs et al., *Proc. Nat'l Acad. Sci.,* 7752–7756, 1990.
Lawton et al., *Plant Mol. Biol.* 9:315–324, 1987.
Lazzeri, *Methods Mol. Biol.,* 49:95–106, 1995.
Lee; Suh; Lee, *Korean J. Genet.,* 11(2):65–72, 1989.
Lee and Saier, *J. of Bacteriol.,* 153–685, 1983.
Levings, *Science,* 250:942–947, 1990.
Lieber and Strauss, *Mol. Cell. Biol.,* 15: 540–551, 1995.
Lindstrom et al., *Developmental Genetics,* 11:160, 1990.
Loomis et al., *J. Expt. Zoology,* 252:9–15, 1989.
Lorz et al., *Mol Gen Genet,* 199:178–182, 1985.
Ma et al., *Nature,* 334:631–633, 1988.
Maeser et al., *Mol. Gen. Genet.,* 230(1–2):170–176, 1991.
Marcotte et al., *Nature,* 335:454, 1988.
Mariani et al., *Nature,* 347:737–741, 1990.
Martinez, Martin, Cerff, *J. Mol. Biol.,* 208(4):551–565, 1989.
McCabe, Martinell, *Bio-Technology,* 11(5):596–598, 1993.

McCormac et al., *Euphytica*, v. 99 (1) p. 17–25:.1998.
McElroy et al., *Mol Gen. Genet.*, 231:150–160, 1991.
McElroy, Zhang, Cao, Wu, *Plant Cell*, 2:163–171, 1990.
Meagher, *Int. Rev. Cytol.*, 125:139–163, 1991.
Michel and Westhof, *J. Mol. Biol.*, 216:585–610, 1990.
Mundy and Chua, *The EMBO J.*, 7:2279–2286, 1988.
Murakami et al., *Mol. Gen. Genet.*, 205:42–50, 1986.
Murashige and Skoog, *Physiol. Plant.*, 15:473–497, 1962.
Murdock et al., *Phytochemistry*, 29:85–89, 1990.
Murray et al., *Nucleic Acids Research*, 17:(2)477–498, 1989.
Nagatani, Honda, Shimada, Kobayashi, *Biotech. Tech.*, 11 (7):471–473, 1997.
Napoli, Lemieux, Jorgensen, *Plant Cell*, 2:279–289, 1990.
Odell et al., *Nature*, 313:810–812, 1985.
Ogawa et al., *Sci. Rep.*, 13:42–48, 1973.
Omirulleh et al., *Plant Mol. Biol.*, 21(3):415–428, 1993.
Ow et al., *Science*, 234:856–859, 1986.
Palukaitis et al., *Virology*, 99:145–151, 1979.
Perlak et al., *Proc. Nat'l Acad. Sci. USA*, 88:3324–3328, 1991.
Perriman et al., *Gene*, 113:157–163, 1992.
Phi-Van et al., *Mol. Cell. Biol*, 10:2302–2307, 1990.
Piatkowski et al., *Plant Physiol*, 94:1682–1688, 1990.
Pignon et al., *Hum. Mutat.*, 3:126–132, 1994.
Poszkowski et al., *EMBO J.*, 3:2719, 1989.
Potrykus etal., *Mol. Gen. Genet.*, 199:183–188, 1985.
Poulsen et al., *Mol. Gen. Genet.*, 205(2): 193–200, 1986.
Prasher et al., *Biochem. Biophys. Res. Commun.*, 126(3):1259–1268, 1985.
Prody et al., *Science*, 231:1577–1580, 1986.
Quigley, Brinkman, Martin, Cerff, *J. Mol. Evol.*, 29(5):412–421, 1989.
Ralston, English, Dooner, *Genet.*, 119(1):185–197, 1988.
Reece, "The actin gene family of rice (*Oryza sativa* L)," Ph.D. thesis, Cornell University, Ithaca, N.Y., 1988.
Reece, McElroy, Wu, *Plant Mol. Biol.*, 14:621–624, 1990.
Reed et al., *J. Gen. Microbiology*, 130:1–4, 1984.
Reichel et al., *Proc. Nat'l Acad. Sci. USA*, 93(12) p.5888–5893. 1996
Reina et al., *Nucl. Acids Res.*, 18(21):6426, 1990.
Reinhold-Hurek and Shub, *Nature*, 357:173–176, 1992.
Rensburg et al., *J. Plant Physiol.*, 141:188–194, 1993.
Rhodes et al., *Methods Mol. Biol.*, 55:121–131, 1995.
Ritala et al., *Plant Mol. Biol.*, 24(2):3 17–325, 1994.
Rochester, Winer, Shah, *EMBO J.*, 5:451–458, 1986.
Rogers et al., *Methods Enzymol.*, 153:253–277, 1987.
Sambrook, Fritsch, and Maniatis, *In Molecular Cloning: A Laboratory Manual*, Second edition, Cold Spring Harbor Laboratory, Cold Spring Harbor, N.Y., 1989.
Sauer, *Mol. and Cell. Biol.*, 7: 2087–2096. 1987.
Schwob et al., *Plant J* 4(3):423–432, 1993.
Shagan and Bar-Zvi, *Plant Physiol.*, 101:1397–1398, 1993.
Shapiro, In: *Mobile Genetic Elements*, 1983.
Sheen et al., *Plant Journal*, 8(5):777–784, 1995.
Shure et al., *Cell*, 35:225–233, 1983.
Simpson, *Science*, 233:34, 1986.
Simpson, Filipowicz, *Plant Mol. Bio.*, 32:1–41, 1996.
Singsit et al., *Transgenic Res.*, 6(2):169–176, 1997.
Skriver and Mundy, *Plant Cell*, 2:503–512, 1990.
Smith, Watson, Bird. Ray. Schuch, Grierson, *Mol. Gen. Genet.*, 224:447–481, 1990.
Southern, *J. Mol. Biol.*, 98:503–517, 1975.
Spencer et al., *Plant Molecular Biology*, 18:201–210, 1992.
Sprague and Dudley, eds., *Corn and Improvement*, 3rd ed, 1988.
Stalker et al., *Science*, 242:419–422, 1988.
Stief et al., *Nature* 341:343 1989.
Sullivan, Christensen, Quail, *Mol. Gen. Genet.*, 215(3):431–440, 1989.
Sutcliffe, *Proc. Nat'l Acad. Sci. USA*, 75:3737–3741, 1978.
Symons, *Annu. Rev. Biochem.*, 61:641–671, 1992.
Tanksley et al., *Bio/Technology*, 7:257–264, 1989.
Tarczynski et al., *Proc. Nat'l Acad. Sci. USA*, 89:1–5, 1992.
Tarczynski et al., *Science*, 259:508–510, 1993.
Thillet et al., *J. Biol. Chem.*, 263:12500–12508, 1988.
Thompson et al., *The EMBO Journal*, 6(9):25 19–2523, 1987.
Thompson, Drayton, Frame, Wang, Dunwell, *Euphytica*, 85(1–3):75–80, 1995.
Tian, Sequin, Charest, *Plant Cell Rep.*, 16:267–271, 1997.
Tingay et al., *The Plant Journal* v. 11 (6) p. 1369–1376. 1997.
Tomes et al., *Plant. Mol. Biol.* 14(2):261–268, 1990.
Tomic et al., *Nucl. Acids Res.*, 12:1656, 1990.
Torbet, Rines, Somers, *Crop Science*, 38(1):226–231, 1998.
Torbet, Rines, Somers, *Plant Cell Reports*, 14(10):635–640, 1995.
Toriyama et al., *Theor Appl. Genet.*, 73:16, 1986.
Tsukada; Kusano; Kitagawa, *Plant Cell Physiol.*, 30(4) 599–604, 1989.
Twell et al., Plant Physiol 91:1270–1274, 1989.
Uchimiya et al., *Mol. Gen. Genet.*, 204:204, 1986.
Ugaki et al., *Nucl. Acid Res.*, 19:371–377, 1991.
Upender, Raj, Weir, *Biotechniques* 18(1):29–30, 1995.
Van der Krol, Mur, Beld, Mol, Stuitje, *Plant Cell*, 2:291–99, 1990.
Van Eck; Blowers; Earle, *Plant Cell Reports*, 14(5):299–304, 1995.
Van Tunen et al., *EMBO J.*, 7:1257, 1988.
Vasil et al., *Plant Physiol.*, 91:1575–1579, 1989.
Vernon and Bohnert, *The EMBO J.*, 11:2077–2085, 1992.
Vodkin et al., *Cell*, 34:1023, 1983.
Vogel, Dawe, Freeling, *J. Cell. Biochem.*, (Suppl. 0) 13:Part D, 1989.
Walker et al., *Proc. Nat'l Acad. Sci. USA*, 84:6624–6628, 1987.
Wandelt and Feix, *Nucl. Acids Res.*, 17(6):2354, 1989.
Wang et al., *Molecular and Cellular Biology*, 12(8):3399–3406, 1992.
Watrud et al., In: *Engineered Organisms and the Environment*, 1985.
Watson and Ramstad, eds., *Corn: Chemistry and Technology*, 1987.
Wenzler etal., *Plant Mol. Biol.*, 12:41–50, 1989.
Withers and King, *Plant Physiol.*, 64:675–678, 1979.
Wolter et al., *The EMBO J.*, 4685–4692, 1992.
Xiang and Guerra, *Plant Physiol.*, 102:287–293, 1993.
Xu et al., *Plant Physiol.*, 110:249–257, 1996.
Yamada et al., *Plant Cell Rep.*, 4:85, 1986.
Yamaguchi-Shinozaki et al., *Plant Cell Physiol.*, 33:217–224, 1992.
Yang and Russell, *Proc. Nat'l Acad. Sci. USA*, 87:4144–4148, 1990.
Yuan and Altman, *Science*, 263:1269–1273, 1994.
Yuan etal., *Proc. Nat'l Acad Sci. USA*, 89:8006–8010, 1992.
Zhang, McElroy, Wu, *The Plant Cell*, 3:1155–1165, 1991.
Zheng and Edwards, *J. Gen. Virol.*, 71:1865–1868, 1990.
Zhou; Stiff; Konzak, *Plant Cell Reports*, 12(11).612–616, 1993.
Zukowsky et al., *Proc. Nat'l Acad. Sci. USA*, 80:1101–1105, 1983.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An isolated nucleic acid comprising a maize RS81 promoter.

2. An isolated maize RS81 promoter isolatable from the nucleic acid sequence of SEQ ID NO:1.

3. The isolated nucleic acid of claim 1, wherein said maize RS81 promoter comprises from about 50 to about 2584 contiguous nucleotides of the nucleic acid sequence of SEQ ID NO:1.

4. The isolated nucleic acid of claim 1, wherein said maize RS81 promoter comprises from about 150 to about 2584 contiguous nucleotides of the nucleic acid sequence of SEQ ID NO:1.

5. The isolated nucleic acid of claim 1, wherein said maize RS81 promoter comprises from about 250 to about 2584 contiguous nucleotides of the nucleic acid sequence of SEQ ID NO:1.

6. The isolated nucleic acid of claim 1, wherein said maize RS81 promoter comprises from about 400 to about 2584 contiguous nucleotides of the nucleic acid sequence of SEQ ID NO:1.

7. The isolated nucleic acid of claim 1, wherein said maize RS81 promoter comprises from about 750 to about 2584 contiguous nucleotides of the nucleic acid sequence of SEQ ID NO:1.

8. The isolated nucleic acid of claim 1, wherein said maize RS81 promoter comprises from about 1000 to about 2584 contiguous nucleotides of the nucleic acid sequence of SEQ ID NO:1.

9. The isolated nucleic acid of claim 1, wherein said maize RS81 promoter comprises the nucleic acid sequence of SEQ ID NO:1.

10. An expression cassette comprising a maize RS81 promoter operably linked to a selected coding region.

11. The expression cassette of claim 10, wherein said selected coding region encodes an insect resistance protein, a bacterial disease resistance protein, a fungal disease resistance protein, a viral disease resistance protein, a nematode disease resistance protein, a herbicide resistance protein, a protein affecting grain composition or quality, a nutrient utilization protein, a mycotoxin reduction protein, a male sterility protein, a selectable marker protein, a screenable marker protein, a negative selectable marker protein, an environment or stress resistance gene, or a protein affecting plant agronomic characteristics.

12. The expression cassette of claim 11, wherein said selected protein is a selectable marker protein selected from the group consisting of phosphinothricin acetyltransferase, glyphosate resistant EPSPS, aminoglycoside phosphotransferase, hygromycin phosphotransferase, dalapon dehalogenase, bromoxynil resistant nitrilase, anthranilate synthase and glyphosate oxidoreductase.

13. An expression vector comprising the expression cassette of claim 10.

14. The expression vector of claim 13, further defined as a plasmid vector.

15. The expression vector of claim 14, wherein said plasmid vector is located within a bacterial cell.

16. A transgenic plant stably transformed with a selected DNA comprising a maize RS81 promoter.

17. The transgenic plant of claim 16, wherein said maize RS81 promoter is isolatable from the nucleic acid sequence of SEQ ID NO:1.

18. The transgenic plant of claim 16, wherein said maize RS81 promoter comprises from about 50 to about 2584 contiguous nucleotides of the nucleic acid sequence of SEQ ID NO:1.

19. The transgenic plant of claim 16, wherein said maize RS81 promoter comprises from about 100 to about 2584 contiguous nucleotides of the nucleic acid sequence of SEQ ID NO:1.

20. The transgenic plant of claim 16, wherein said maize RS81 promoter comprises from about 200 to about 2584 contiguous nucleotides of the nucleic acid sequence of SEQ ID NO:1.

21. The transgenic plant of claim 16, wherein said maize RS81 promoter comprises from about 400 to about 2584 contiguous nucleotides of the nucleic acid sequence of SEQ ID NO:1.

22. The transgenic plant of claim 16, wherein said maize RS81 promoter comprises from about 750 to about 2584 contiguous nucleotides of the nucleic acid sequence of SEQ ID NO:1.

23. The transgenic plant of claim 16, wherein said maize RS81 promoter comprises from about 1000 to about 2584 contiguous nucleotides of the nucleic acid sequence of SEQ ID NO:1.

24. The transgenic plant of claim 16, wherein said maize RS81 promoter comprises from about 1500 to about 2584 contiguous nucleotides of the nucleic acid sequence of SEQ ID NO:1.

25. The transgenic plant of claim 16, wherein said maize RS81 promoter comprises from about 2000 to about 2584 contiguous nucleotides of the nucleic acid sequence of SEQ ID NO:1.

26. The transgenic plant of claim 16, wherein said maize RS81 promoter comprises the nucleic acid sequence of SEQ ID NO:1.

27. The transgenic plant of claim 16, wherein said s elected DNA further comprises a selected coding region operably linked to said maize RS81 promoter.

28. The transgenic plant of claim 27, wherein said s elected coding region encodes an insect resistance protein, a bacterial disease resistance protein, a fungal disease resistance protein, a viral disease resistance protein, a nematode disease resistance protein, a herbicide resistance protein, a protein affecting grain composition or quality, a nutrient utilization protein, an environment or stress resistance protein, a mycotoxin reduction protein, a male sterility protein, a selectable marker protein, a screenable marker protein, a negative selectable marker protein, or a protein affecting plant agronomic characteristics.

29. The transgenic plant of claim 28, wherein said selected protein is a selectable marker protein selected from the group consisting of phosphinothricin acetyltransferase, glyphosate resistant EPSPS, aminoglycoside phosphotransferase, hygromycin phosphotransferase, neomycin phosphotransferase, dalapon dehalogenase, bromoxynil resistant nitrilase, anthranilate synthase and glyophosate oxidoreductase.

30. The transgenic plant of claim 16, wherein said selected DNA comprises plasmid DNA.

31. The transgenic plant of claim 16, further defined as a monocotyledonous plant.

32. The transgenic plant of claim 31, wherein said monocotyledonous plant is selected from the group consisting of wheat, maize, rye, rice, oat, barley, turfgrass, sorghum, millet and sugarcane.

33. The transgenic plant of claim 16, further defined as a dicotyledonous plant.

34. The transgenic plant of claim 33, wherein said dicotyledonous plant is selected from the group consisting of tobacco, tomato, potato, soybean, cotton, canola, alfalfa and sunflower.

35. The transgenic plant of claim 34, wherein said dicotyledonous plant is a soybean plant.

36. The transgenic plant of claim 16, further defined as a fertile $R_0$ transgenic plant.

37. A method of expressing a selected protein in a transgenic plant comprising the steps of:
(i) obtaining a construct comprising a selected coding region operably linked to a maize RS81 promoter;
(ii) transforming a recipient plant cell with said construct; and
(iii) regenerating a transgenic plant expressing said selected protein from said recipient plant cell.

38. The method of claim 37, wherein said step of transforming comprises a method selected from the group consisting of microprojectile bombardment, PEG mediated transformation of protoplasts, electroporation, silicon carbide fiber mediated transformation, or Agrobacterium-mediated transformation.

39. The method of claim 38, wherein said step of transforming comprises microprojectile bombardment.

40. The method of claim 37, wherein said recipient plant cell is from a monocotyledonous plant.

41. The method of claim 40, wherein said monocotyledonous plant is selected from the group consisting of wheat, maize, rye, rice, turfgrass, oat, barley, sorghum, millet, and sugarcane.

42. The method of claim 41, wherein the monocotyledonous plant is a maize plant.

43. The method of claim 37, wherein said recipient plant cell is from a dicotyledonous plant.

44. The method of claim 43, wherein said dicotyledonous plant is selected from the group consisting of tobacco, tomato, potato, soybean, canola, sunflower, alfalfa and cotton.

45. The method of claim 37, wherein said selected protein is selected from the group consisting of an insect resistance protein, a bacterial disease resistance protein, a fungal disease resistance protein, a viral disease resistance protein, a nematode disease resistance protein, a herbicide resistance protein, a protein affecting grain composition or quality, a nutrient utilization protein, a mycotoxin reduction protein, a male sterility protein, a selectable marker protein, a screenable marker protein, a negative selectable marker protein, a protein affecting plant agronomic characteristics, and an environment or stress resistance protein.

46. A transgenic plant cell stably transformed with a selected DNA comprising a maize RS81 promoter.

47. The transgenic plant cell of claim 46, wherein said maize RS81 promoter is isolatable from the nucleic acid sequence of SEQ ID NO:1.

48. The transgenic plant cell of claim 46, wherein said maize RS81 promoter comprises from about 50 to about 2584 contiguous nucleotides of the nucleic acid sequence of SEQ ID NO:1.

49. The transgenic plant cell of claim 46, wherein said maize RS81 promoter comprises from about 100 to about 2584 contiguous nucleotide s of the nucleic acid sequence of SEQ ID NO:1.

50. The transgenic plant cell of claim 46, wherein said maize RS81 promoter comprises from about 200 to about 2584 contiguous nucleotides of the nucleic acid sequence of SEQ ID NO:1.

51. The transgenic plant cell of claim 46, wherein said maize RS81 promoter comprises from about 400 to about 2584 contiguous nucleotides of the nucleic acid sequence of SEQ ID NO:1.

52. The transgenic plant cell of claim 46, wherein said maize RS81 promoter comprises from about 750 to about 2584 contiguous nucleotides of the nucleic acid sequence of SEQ ID NO:1.

53. The transgenic plant cell of claim 46, wherein said maize RS81 promoter comprises from about 1000 to about 2584 contiguous nucleotides of the nucleic acid sequence of SEQ ID NO:1.

54. The transgenic plant cell of claim 46, wherein said maize RS81 promoter comprises from about 1500 to about 2584 contiguous nucleotides of the nucleic acid sequence of SEQ ID NO:1.

55. The transgenic plant cell of claim 46, wherein said maize RS81 promoter comprises from about 2000 to about 2584 contiguous nucleotides of the nucleic acid sequence of SEQ ID NO:1.

56. The transgenic plant cell of claim 46, wherein said maize RS81 promoter comprises the nucleic acid sequence of SEQ ID NO:1.

57. The transgenic plant cell of claim 46, wherein said selected DNA further comprises a selected coding region operably linked to said maize RS81 promoter.

58. The transgenic plant cell of claim 57, wherein said selected coding region encodes an insect resistance protein, a bacterial disease resistance protein, a fungal disease resistance protein, a viral disease resistance protein, a nematode disease resistance protein, a herbicide resistance protein, a protein affecting grain composition or quality, a nutrient utilization protein, an environment or stress resistance protein, a mycotoxin reduction protein, a male sterility protein, a selectable marker protein, a screenable marker protein, a negative selectable marker protein, or a protein affecting plant agronomic characteristics.

59. The transgenic plant cell of claim 58, wherein said selected protein is a selectable marker protein selected from the group consisting of phosphinothricin acetyltransferase, glyphosate resistant EPSPS, aminoglycoside phosphotransferase, hygromycin phosphotransferase, neomycin phosphotransferase, dalapon dehalogenase, bromoxynil resistant nitrilase, anthranilate synthase and glyphosate oxidoreductase.

60. The transgenic plant cell of claim 46, wherein said selected DNA comprises plasmid DNA.

61. The transgenic plant cell of claim 46, further defined as from a monocotyledonous plant.

62. The transgenic plant cell of claim 61, wherein said monocotyledonous plant is selected from the group consisting of wheat, maize, rye, rice, oat, barley, turfgrass, sorghum, millet and sugarcane.

63. The transgenic plant cell of claim 46, further defined as from a dicotyledonous plant.

64. The transgenic plant cell of claim 63, wherein said dicotyledonous plant is selected from the group consisting of tobacco, tomato, potato, soybean, cotton, canola, alfalfa and sunflower.

65. The transgenic plant cell of claim 64, wherein said dicotyledonous plant is a soybean plant.

66. The method of claim 37, wherein said transgenic plant is fertile.

\* \* \* \* \*

UNITED STATES PATENT AND TRADEMARK OFFICE
CERTIFICATE OF CORRECTION

PATENT NO. : 6,207,879 B1
DATED : March 27, 2001
INVENTOR(S) : McElroy, et al.

It is certified that error appears in the above-identified patent and that said Letters Patent is hereby corrected as shown below:

Column 75,
Line 67, please replace "RS8 1" with -- RS81 --.

Column 76,
Line 15, please replace "Hill" with -- HiII --.

Column 97,
Line 32, please move "s" to line 33 immediately before "elected".
Line 35, please move "s" to line 36 immediately before "elected".

Signed and Sealed this

Sixth Day of November, 2001

Attest:

NICHOLAS P. GODICI
*Attesting Officer*     *Acting Director of the United States Patent and Trademark Office*

SEQUENCE LISTING

<160> NUMBER OF SEQ ID NOS: 13

<210> SEQ ID NO 1
<211> LENGTH: 2584
<212> TYPE: DNA
<213> ORGANISM: Zea mays
<220> FEATURE:
<221> NAME/KEY: modified_base
<222> LOCATION: (321)..(2162)
<223> OTHER INFORMATION: N = A or C or G or T

<400> SEQUENCE: 1

| gtcaacggat | cacatagcta | gcgtctgatt | ccatgtgaaa | tactttttt | cccgaacaca | 60 |
| tgatatcccc | attttcattc | atttcggatc | atttgaattg | aattacattc | taataattat | 120 |
| aatttagaca | catattaatt | aagctaatat | gattctatgc | ggaatatatt | tgtaaatgct | 180 |
| cgtaatatat | tttaagcact | gttttagatt | taaaagttct | ctttcgacct | tcagcgttct | 240 |
| gtcattttgt | taaggctaag | gtggatctaa | agttttgcag | ggagctagtg | tcaaggaaga | 300 |
| cctaatactt | ccactcacga | ngagcaacta | ggcaagccac | acccttataa | aaaaaaggca | 360 |
| aaccagacag | tcananagac | aggggctctt | ccgccaactg | gaccttgatg | ttgccagtca | 420 |
| tgcgctgaaa | gattccaaat | cctcaatcgc | anactgcctt | gtcaatcatt | ttttgcatta | 480 |
| aggntaaagc | gataaggtaa | acaaccattg | gartnktkgt | taacancanc | ctggcacggc | 540 |
| cggatgcntn | ntntgaataa | tantnnggg | ncaagacagg | aanncntaat | ntttggaaat | 600 |
| tttagtggnt | aggagtcact | gatcatggac | ntaagagtgc | taacccactg | cattancaaa | 660 |
| aancgtgtgg | gtgttgcggn | ttccaanttg | tccgttgtca | cggnatggta | tgaatatgcc | 720 |
| aaagattctc | gctgttttgt | gaaatttaga | tgagctgagc | atgacaaaag | cgcaaacctt | 780 |
| aattgcattg | cctactccat | atatggcaag | atggcttgca | tgacaaaatt | agatgttaac | 840 |
| aaaaagaaaa | caaggagaag | gtatagaggt | gctcgaaaga | ctcgttgaca | ctttaaactc | 900 |
| gggtgtgcgt | gtgttatgtg | tttatctgct | gtattcagaa | cggctcgtca | taatagcgta | 960 |
| catatatata | tatatatgat | ccaattttga | aagtactaga | taaatataag | atactatgca | 1020 |
| tttaaactat | attatagtct | tatactctta | tcttagaacc | ggaaccgtcc | tatacattat | 1080 |
| ctcttaatag | cctctccctc | aatcttaatc | ttctctaggt | ttagattatg | gttagatcga | 1140 |
| attctctact | aatcttacga | ataaagcttt | agtaaatcag | ccaaccacnt | cattctttng | 1200 |
| aataaacaaa | atcaatctca | agcattctta | taaaaactct | ttctcgaaca | aattgataac | 1260 |
| caaattctat | atgctttatt | atnggcdtgg | aacaaacgaa | ttagatnaca | aatatnttt | 1320 |
| gcatatcatg | cgcgcgchag | tgatgtttta | cttttactcn | tcggtcacag | ggttthgcct | 1380 |
| ccttgaawtc | gaaagggaa | tactgamtgg | ccaaattgct | tatggagttg | ttaaagaata | 1440 |
| caaaaatagg | tgccgaaagg | gtttgctcta | atgatttgat | gaagtcgttg | ccmccgatgg | 1500 |
| ttaccatgca | gtactactac | tatcatagtg | tcatggtttt | tttatttca | attgctgtac | 1560 |
| tgatgcagac | gtgacgcatg | cgtttactat | ccttgcagcc | accgactcca | aaatgaagag | 1620 |

-continued

```
agctagcgct caattcattg gtccacgtca ccatcaacgt tccgaactgt ctcgcatgca    1680
tcgtgccgag aaaaagagca ccgatgacna tggatgcgat cgadttccca ccatttgaga    1740
gcaatatgcg ttttacactt tacaacaagg tacaagtgaa acaataaacc atgctaaata    1800
aaagcgctaa gggctgattt ggtggcccag aatcacggga ggattggagg ggattgagag    1860
agaaattagt tcatttcctc ctcaatcatc tacaattctc tcgtgattct acttatcacc    1920
aaatcaatct aaaacttacg tctctcctgc tgcgctctcg caccacactg caggaacgta    1980
cgcccggccg aggctgcaac tgaaatggaa gtatgaaacc cttcggcttt tgtttcctga    2040
ttgaccaact gtgacaaatc ccctagcatt ttgcaagaac aactacatag acgttgagat    2100
aacatatata tcctccaaac gagacagccc atctgacaac acttgcagcc gttcgaacgt    2160
tnccattacc aaaatattta agcgttacac aagagatagc gtacctccaa tgattagcgg    2220
ctttgccgtt tattattgtc attggcgcat tgctttggtg tacctcacat ggacacgcca    2280
tgaaaagatg acaatagcgc aaacagacat ccgaacaaag cttggtgcgc ctgctctcgg    2340
ccgggctagc tagtaccaat catggaataa taagctagta tatatatacc gccccattta    2400
taaaaatgta aataaaatgt tctgtggcga ttatgcacac cgtccataat actctagtcg    2460
tcggcaagct gaggccgccc attaagcctt gagcgtgtat aaaaggggca tagactccca    2520
gcatcagcga agcagcaaca tatcaagctc agagcctcag agcgccagcc aagtcttgcg    2580
gtcg                                                                 2584
```

<210> SEQ ID NO 2
<211> LENGTH: 329
<212> TYPE: DNA
<213> ORGANISM: RICE

<400> SEQUENCE: 2

```
gggctgcgag gagtctggtg gcacctaagc cgtcatcgtc atatatgcct cgtttaattg     60
ttcatctctg attcgatgat gtctcccacc ttgtttcgtg tgttcccagt ttgttcatcg    120
tcttttgatt ttaccggccg tgctctgctt ttgtttttgt ttcacctgat ctctctctga    180
cttgatgtaa gagtggtatc tgctacgact atatgttgtt gggtgaggca tatgtgaatg    240
aaatmtatgr aagctccggc tatatatatt tatacaaagg gtatgagatg gatgtgaatc    300
tagagcatat gtgtccaaca atcaattcg                                     329
```

<210> SEQ ID NO 3
<211> LENGTH: 2640
<212> TYPE: DNA
<213> ORGANISM: RICE
<220> FEATURE:
<221> NAME/KEY: modified_base
<222> LOCATION: (1094)..(2167)
<223> OTHER INFORMATION: N = A or C or G or T

<400> SEQUENCE: 3

```
gaattcccgg acctccatgc ctacatcaac taatttgatt ccttgagttt acgtttagtg     60
atatgtctat ttttagagct tgttggggct tcggcctcag ctctagccag ccaaacatgt    120
tctaccaagt accctatgtt ggcatgatat agtgatgcat tataacaata aatgagcgag    180
ggattgctgg ctgaaaaagc tatactagct gcatttggtt atagttaacc gaactattaa    240
ttgcgtgtac aacaaaataa aaaaaatgca tgttgcacat tctttcatta acattatgtt    300
ttggtagtgt gaattagaaa tttgattgac agtagatcga caaacatagt ttcaatatgc    360
```

-continued

```
ttaagttagt tatgacttta acatatcagt ctccttgata ttttcgtttt agattcgtct      420
ctctactagt gtgtatgtcc accttccata gcagtgaagg gttccattcc atccctggta      480
aaaaaaaatc aaccactact atttatttcc taaaaagcaa aatgataaaa tatcattttt      540
ttaataaaaa taaaaaaatt ttggggtaca taattgatgt tgcccttgg gattaacctt      600 aaaaagggc gaattttcta gggttttggcc aagttttgca atgcaccaaa ttattcccct      660
tgggccggcc gccacccaa aaaaaacccc aaccccaac tttccattga aggccgggcc      720
cccttaaatc ctcatccccc caatttccac caccatcgcc attgccacca cctctcctat      780
atctcgccct ccccctcctc cctcccacgc cattcgcctc cttcttgctg cagccgccat      840
ccccggttcg gttctctcct cttctttagg tgagcaactg cctctccatg tccaggccct      900 cccggcccy gsktgswtty tgktttaawg skkgakgttt ytkgcaaats ggarrkgttt      960
tmkwtttctg ttarrwgggk ggaaawackg aackgarttg ctgaaaktag gkgttggctg     1020
ggtkgctttt ggctkgtawg ttgtcaaakg ttggawccgt tggamtgtag gragttcagg     1080 grakssccsta aacnggtgtt gtttctgggg gatgctgatc cgatccgatg gcttttagtn     1140
gatggaagta tccgatcttg tttgtgctga ggtgacgagt attcttgcag tagatctttt     1200
tcgtgtttat gttgtgttgt gctaaggtct tgtagttccc aaaatttttt ccccaaaaat     1260
gtcaacatgg tatctttaga cacatgaata gagcattaaa tatagattaa aaaaaactaa     1320
ttgcacaatt tgcatggaaa atcgtgagac caatcttta agcctaatta gtccatgatt     1380
agacataagt gctacagtaa cccacgtgtg ctaatgatgg attaattagg cttaataaat     1440
tcgtctctca gttttctagg cgagctatga aattaatttt ttttattcgt gtccgaaaat     1500 ccttccgac atccggttaa acgtcggatg tgacaagaaa aattttcttt tcgcgaacta     1560
aacaaggcct aaggcgtgaa gttgggggta tgtttacttt gaattgtaga tcaactgaca     1620
gacttttgca tgctcatagc cggtttgttt gcggtactca agaaactgtc ttgattggtc     1680
attccgtagg gtggggactk gkgaaaaagc tgattccttt cttttcattt ccacggttgc     1740
tttcttggtt ggcgtgggaa aaaaacagtt ttcagtactg taccgatcga cttctttttg     1800
agactttttt ctccttcaac aaaacatttc atagttcaca caaaaacaca agcataccaa     1860
cgatttcatt atgtgacatg gcttctaaaa tctgaattaa agaagcaagt tgcttaactg     1920
aaaactgcct agtttcagaa atcatggagt ttaaattttc caagagaag ggtaacatat      1980 tatggagaac tagaattttg ttactaaaaa atgtatgctt atgggaccac tattctaaga     2040
tgcttcacat cttgatgacg gctgtctgat cagaaaaaaa ataatgcttc agatcaacca     2100
atcagacaat ccaggatatg agcagatcat gttgcattca ttycatccac tgaagcangt     2160
cccnannttc ttcccctgaa gattggtcta aatcgattca taaaacacat tgcatgtatg     2220
cttcttagga gagagcacca ttcccttttgg agggttggtg attcagacca gcctcggttg     2280
attgatttga atttcttaac tacaagtcac ttgatctagt tataatttac gcatcatgga     2340
ccattcattt tgggagtttc ctatatacaa ctaaagtgtt atacttcttc ctatctgcgc     2400
cttccttttt gtttgaataa tcctccctct ttcacaattt gcaatactag ttagtcaatt     2460
aatagctttg aatgtgatat cttaaagaca tgtattttgt cattcatgtt tgatgaagac     2520
tcgtgttttt gtaggatgaa tgtttagttc aagttacatt tttctgtatt aatctatagt     2580
ctttgtaaac actgttttga atgatttatt ttgtgttatg cagatcagtt aggtaccatg     2640
```

<210> SEQ ID NO 4
<211> LENGTH: 1763

<212> TYPE: DNA
<213> ORGANISM: RICE
<220> FEATURE:
<221> NAME/KEY: modified_base
<222> LOCATION: (234)..(1307)
<223> OTHER INFORMATION: N = A or C or G or T

<400> SEQUENCE: 4

```
cttctttagg tgagcaactg cctctccatg tccaggccct cccggccccy gsktgswtty       60
tgktttaawg skkgakgttt ytkgcaaats ggarrkgttt tmkwtttctg ttarrwgggk      120
ggaaawackg aackgarttg ctgaaaktag gkgttggctg ggtkgctttt ggctkgtawg      180
ttgtcaaakg ttggawccgt tggamtgtag gragttcagg graksscsta aacnggtgtt      240
gtttctgggg gatgctgatc cgatccgatg gcttttagtn gatggaagta tccgatcttg      300
tttgtgctga ggtgacgagt attcttgcag tagatctttt tcgtgtttat gttgtgttgt      360
gctaaggtct tgtagttccc aaaattttt ccccaaaaat gtcaacatgg tatctttaga      420
cacatgaata gagcattaaa tatagattaa aaaaaactaa ttgcacaatt tgcatggaaa      480
atcgtgagac caatctttta agcctaatta gtccatgatt agacataagt gctacagtaa      540
cccacgtgtg ctaatgatgg attaattagg cttaataaat tcgtctctca gttttctagg      600
cgagctatga aattaatttt ttttattcgt gtccgaaaat cccttccgac atccggttaa      660
acgtcggatg tgacaagaaa aattttcttt tcgcgaacta acaaggcct aaggcgtgaa      720
gttgggggta tgtttacttt gaattgtaga tcaactgaca gacttttgca tgctcatagc      780
cggtttgttt gcggtactca agaaactgtc ttgattggtc attccgtagg gtggggactk      840
gkgaaaaagc tgattccttt cttttcattt ccacggttgc tttcttggtt ggcgtgggaa      900
aaaaacagtt ttcagtactg taccgatcga cttttcttttg agactttttt ctccttcaac      960
aaaacatttc atagttcaca caaaaacaca agcataccaa cgatttcatt atgtgacatg     1020
gcttctaaaa tctgaattaa agaagcaagt tgcttaactg aaaactgcct agtttcagaa     1080
atcatggagt ttaaattttc caagagaag ggtaacatat tatggagaac tagaattttg     1140
ttactaaaaa atgtatgctt atgggaccac tattctaaga tgcttcacat cttgatgacg     1200
gctgtctgat cagaaaaaaa ataatgcttc agatcaacca atcagacaat ccaggatatg     1260
agcagatcat gttgcattca ttycatccac tgaagcangt cccnannttc ttcccctgaa     1320
gattggtcta aatcgattca taaaacacat tgcatgtatg cttcttagga gagagcacca     1380
ttcccttttgg agggttggtg attcagacca gcctcggttg attgatttga atttcttaac     1440
tacaagtcac ttgatctagt tataatttac gcatcatgga ccattcattt tgggagtttc     1500
ctatatacaa ctaaagtgtt atacttcttc ctatctgcgc cttccttttt gtttgaataa     1560
tcctccctct ttcacaattt gcaatactag ttagtcaatt aatagctttg aatgtgatat     1620
cttaaagaca tgtattttgt cattcatgtt tgatgaagac tcgtgttttt gtaggatgaa     1680
tgtttagttc aagttacatt tttctgtatt aatctatagt ctttgtaaac actgttttga     1740
atgatttatt ttgtgttatg cag                                             1763
```

<210> SEQ ID NO 5
<211> LENGTH: 889
<212> TYPE: DNA
<213> ORGANISM: RICE
<220> FEATURE:
<221> NAME/KEY: modified_base
<222> LOCATION: (225)..(423)
<223> OTHER INFORMATION: N = A or C or G or T -continued

```
<400> SEQUENCE: 5
gtaaccaact gcctctccat gtccaggccc tcccggcccc ygsktgswtt ytgktttaaw      60
gskkgakgtt tytkgcaaat sggarrkgtt ttmkwtttct gttarrwggg kggaaawack     120
gaackgartt gctgaaakta ggkgttggct gggtkgcttt tggctkgtaw gttgtcaaak     180
gttggawccg ttggamtgta ggragttcag ggraksscst aaacnggtgt tgtttctggg     240
ggatgctgat ccgatccgat ggcttttagt ngatggaagt atccgatctt gtttgtgctg     300
aggtgacgag tattcttgca gtagatcaga aaaaaaataa tgcttcagat caaccaatca     360
gacaatccag gatatgagca gatcatgttg cattcattyc atccactgaa gcangtcccn     420
annttcttcc cctgaagatt ggtctaaatc gattcataaa acacattgca tgtatgcttc     480
ttaggagaga gcaccattcc ctttggaggg ttggtgattc agaccagcct cggttgattg     540
atttgaattt cttaactaca agtcacttga tctagttata atttacgcat catggaccat     600
tcattttggg agtttcctat atacaactaa agtgttatac ttcttcctat ctgcgccttc     660
cttttttgttt gaataatcct ccctctttca caatttgcaa tactagttag tcaattaata     720
gctttgaatg tgatatctta aagacatgta ttttgtcatt catgtttgat gaagactcgt     780
gttttttgtag gatgaatgtt tagttcaagt tacattttc tgtattaatc tatagtcttt     840
gtaaacactg ttttgaatga tttatttttt tttttgcagg tcgactagg                 889

<210> SEQ ID NO 6
<211> LENGTH: 45
<212> TYPE: DNA
<213> ORGANISM: Zea mays

<400> SEQUENCE: 6
ctgcagccgc catccccggt tctctcctct tctttaggtg agcaa                       45

<210> SEQ ID NO 7
<211> LENGTH: 45
<212> TYPE: DNA
<213> ORGANISM: Zea mays

<400> SEQUENCE: 7
ctgcagctgc catccccggt tctctcctct tctttaggta accaa                       45

<210> SEQ ID NO 8
<211> LENGTH: 10
<212> TYPE: DNA
<213> ORGANISM: Zea mays
<220> FEATURE:
<221> NAME/KEY: modified_base
<222> LOCATION: (9)..(10)
<223> OTHER INFORMATION: N = A or C or G or T

<400> SEQUENCE: 8 aggtaagtnn                                                              10

<210> SEQ ID NO 9
<211> LENGTH: 32
<212> TYPE: DNA
<213> ORGANISM: Zea mays

<400> SEQUENCE: 9
tttgtgttat gcagatcagt taaaataaat gg                                     32

<210> SEQ ID NO 10
<211> LENGTH: 32
```

```
-continued

<212> TYPE: DNA
<213> ORGANISM: Zea mays

<400> SEQUENCE: 10
tttttttttt gcaggtcgac taggtaccat gg                                    32

<210> SEQ ID NO 11
<211> LENGTH: 23
<212> TYPE: DNA
<213> ORGANISM: Zea mays

<400> SEQUENCE: 11
tttttttttt gcaggtacaa tgg                                              23

<210> SEQ ID NO 12
<211> LENGTH: 25
<212> TYPE: DNA
<213> ORGANISM: Streptomyces hygroscopicus

<400> SEQUENCE: 12
catcgagaca agcacggtca acttc                                            25

<210> SEQ ID NO 13
<211> LENGTH: 28
<212> TYPE: DNA
<213> ORGANISM: Streptomyces hygroscopicus

<400> SEQUENCE: 13
aagtccctgg aggcacaggg cttcaaga                                         28
```